US012715938B2

(12) United States Patent
Colhoun et al.

(10) Patent No.: US 12,715,938 B2
(45) **Date of Patent: *Aug. 25, 2026**

(54) CELLULOSE ESTER COMPOSITIONS DERIVED FROM RECYCLED CELLULOSE ESTER CONTENT SYNGAS

(71) Applicant: Eastman Chemical Company, Kingsport, TN (US)

(72) Inventors: Frederick Leslie Colhoun, Kingsport, TN (US); Ronald Buford Sheppard, Kingsport, TN (US); William Lewis Trapp, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 1158 days.

This patent is subject to a terminal disclaimer.

(21) Appl. No.: 17/754,151

(22) PCT Filed: Sep. 24, 2020

(86) PCT No.: PCT/US2020/052401

§ 371 (c)(1),
(2) Date: Mar. 25, 2022

(87) PCT Pub. No.: WO2021/061918

PCT Pub. Date: Apr. 1, 2021

(65) Prior Publication Data

US 2022/0289868 A1 Sep. 15, 2022

Related U.S. Application Data

(60) Provisional application No. 62/907,139, filed on Sep. 27, 2019.

(51) Int. Cl.

| | |
|---|---|
| ***C08B 3/06*** | (2006.01) |
| ***C07C 29/151*** | (2006.01) |
| ***C07C 51/09*** | (2006.01) |
| ***C07C 51/16*** | (2006.01) |
| ***C07C 67/08*** | (2006.01) |
| ***C10J 3/46*** | (2006.01) |

(52) U.S. Cl.

CPC ............ *C08B 3/06* (2013.01); *C07C 29/1518* (2013.01); *C07C 51/09* (2013.01); *C07C 51/16* (2013.01); *C07C 67/08* (2013.01); *C10J 3/46* (2013.01); *C10J 2300/093* (2013.01); *C10J 2300/0946* (2013.01); *C10J 2300/0959* (2013.01); *C10J 2300/1665* (2013.01)

(58) Field of Classification Search

CPC ..... C08L 1/12; C08L 1/14; C08B 1/02; C08B 3/00; C08B 3/06; C08B 3/16; C08B 3/18

USPC .................................................. 536/25.4, 71

See application file for complete search history.

(56) References Cited

U.S. PATENT DOCUMENTS

| | | | |
|---|---|---|---|
| 1,683,347 | A | 9/1928 | Gray et al. |
| 1,698,049 | A | 1/1929 | Clarke et al. |
| 1,880,560 | A | 10/1932 | Webber et al. |
| 1,880,808 | A | 10/1932 | Clark et al. |
| 1,984,147 | A | 12/1934 | Malm |
| 2,129,052 | A | 9/1938 | Fordyce |
| 2,904,050 | A | 9/1959 | Kiefer |
| 3,544,291 | A | 12/1970 | Schlinger et al. |
| 3,617,201 | A | 11/1971 | Berni et al. |
| 3,817,725 | A | 6/1974 | Sieg et al. |
| 3,841,851 | A | 10/1974 | Kaiser |
| 3,909,364 | A | 9/1975 | Singh |
| 3,991,557 | A | 11/1976 | Donath |
| 4,052,173 | A | 10/1977 | Schulz |
| 4,081,253 | A | 3/1978 | Marion |
| 4,147,603 | A | 4/1979 | Pacifici et al. |
| 4,152,119 | A | 5/1979 | Schulz |
| 4,199,327 | A | 4/1980 | Hempill et al. |
| 4,225,457 | A | 9/1980 | Schulz |
| 4,377,394 | A | 3/1983 | Muenger |
| 4,502,633 | A | 3/1985 | Saxon |
| 4,758,645 | A | 7/1988 | Miyazono et al. |
| 4,839,230 | A | 6/1989 | Cook |
| 4,861,629 | A | 8/1989 | Nahm |
| 4,886,000 | A | 12/1989 | Hölter et al. |
| 5,082,914 | A | 1/1992 | Cook et al. |
| 5,182,379 | A | 1/1993 | Cook et al. |
| 5,292,877 | A | 3/1994 | Edgar et al. |
| 5,323,714 | A | 6/1994 | Cox |

(Continued)

FOREIGN PATENT DOCUMENTS

| | | | |
|---|---|---|---|
| CA | 2 937 445 | A1 | 1/2018 |
| CN | 1102605 | C | 3/2003 |

(Continued)

OTHER PUBLICATIONS

Wibowo et al, Composites: Part A, 2006, 1428-1433.*

(Continued)

*Primary Examiner* — Ganapathy Krishnan

(74) *Attorney, Agent, or Firm* — Robert C. Morriss

(57) ABSTRACT

A process for preparing a recycle cellulose ester and a recycle cellulose ester composition and articles made with such recycle cellulose esters comprising at least one cellulose ester having at least one substituent on an anhydroglucose unit (AU) derived from recycled cellulose ester content syngas are provided. The recycled cellulose ester content syngas can be obtained by gasifying feedstocks containing a solid fossil fuel such as coal, a cellulose ester, and water. The cellulose ester can be post-consumer or post-industrial cellulose ester.

17 Claims, 4 Drawing Sheets

(56) References Cited

U.S. PATENT DOCUMENTS

| | | | |
|---|---|---|---|
| 5,384,163 | A | 1/1995 | Budde et al. |
| 5,445,659 | A | 8/1995 | Khan et al. |
| 5,457,250 | A | 10/1995 | Gerhardus et al. |
| 5,498,827 | A | 3/1996 | Khan et al. |
| 5,534,040 | A | 7/1996 | Khan et al. |
| 5,656,042 | A | 8/1997 | Khan et al. |
| 5,723,151 | A | 3/1998 | Cook et al. |
| 5,741,901 | A | 4/1998 | Cook et al. |
| 5,750,677 | A | 5/1998 | Edgar et al. |
| 5,821,111 | A | 10/1998 | Grady et al. |
| 5,871,573 | A | 2/1999 | Cook et al. |
| 5,904,879 | A | 5/1999 | Winter et al. |
| 5,922,090 | A | 7/1999 | Fujimura et al. |
| 5,970,988 | A | 10/1999 | Buchanan et al. |
| 5,981,738 | A | 11/1999 | Cook et al. |
| 5,984,985 | A | 11/1999 | Malone |
| 6,063,355 | A | 5/2000 | Fujimura et al. |
| 6,269,286 | B1 | 7/2001 | Tse et al. |
| 6,321,666 | B1 | 11/2001 | Tigonen |
| 6,369,214 | B1 | 4/2002 | Tye et al. |
| 6,401,635 | B1 | 6/2002 | Nieminen et al. |
| 6,436,168 | B1 | 8/2002 | Uematsu et al. |
| 6,439,135 | B1 | 8/2002 | Pope |
| 6,571,802 | B1 | 6/2003 | Yamashita |
| 6,676,716 | B2 | 1/2004 | Fujimura et al. |
| 6,892,654 | B2 | 5/2005 | Whittaker et al. |
| 7,425,315 | B2 | 9/2008 | Kruesi |
| 7,453,393 | B2 | 11/2008 | Duivenvoorden |
| 7,500,997 | B2 | 3/2009 | Norbeck et al. |
| 7,531,618 | B2 | 5/2009 | DeBruin |
| 8,083,818 | B2 | 12/2011 | Ploeg et al. |
| 8,202,913 | B2 | 6/2012 | Robinson et al. |
| 8,246,700 | B1 | 8/2012 | Kutsin |
| 8,303,676 | B1 | 11/2012 | Weaver et al. |
| 8,349,034 | B2 | 1/2013 | Calabrese et al. |
| 8,349,039 | B2 | 1/2013 | Robinson |
| 8,361,428 | B2 | 1/2013 | Raman et al. |
| 8,580,152 | B2 | 11/2013 | Sutradhar et al. |
| 8,585,789 | B2 | 11/2013 | Sutradhar et al. |
| 8,722,958 | B2 | 5/2014 | Kashimoto |
| 8,734,547 | B2 | 5/2014 | Rappas et al. |
| 8,759,596 | B2 | 6/2014 | Yie et al. |
| 8,828,105 | B2 | 9/2014 | Calabrese et al. |
| 8,863,518 | B2 | 10/2014 | Koseoglu |
| 8,915,199 | B2 | 12/2014 | Bohlig et al. |
| 8,957,275 | B2 | 2/2015 | Stein et al. |
| 8,999,021 | B2 | 4/2015 | Sutradhar et al. |
| 9,023,124 | B2 | 5/2015 | Weaver et al. |
| 9,034,061 | B2 | 5/2015 | Robinson et al. |
| 9,133,405 | B2 | 9/2015 | Abughazaleh |
| 9,139,785 | B2 | 9/2015 | Tsantrizos |
| 9,200,207 | B2 | 12/2015 | Huang et al. |
| 9,416,077 | B2 | 8/2016 | Kelfkens et al. |
| 9,698,439 | B2 | 7/2017 | Weaver et al. |
| 9,834,728 | B2 | 12/2017 | Fleckner et al. |
| 9,982,205 | B2 | 5/2018 | Pichach |
| 10,329,501 | B2 | 6/2019 | Bai et al. |
| 11,312,914 | B2 | 4/2022 | Trapp et al. |
| 11,370,983 | B2 | 6/2022 | Trapp et al. |
| 11,447,576 | B2 * | 9/2022 | Sheppard .................. C08B 3/18 |
| 2001/0006036 | A1 | 7/2001 | Kleiss |
| 2002/0113228 | A1 | 8/2002 | Kim et al. |
| 2003/0131582 | A1 | 7/2003 | Anderson et al. |
| 2004/0031424 | A1 | 2/2004 | Pope |
| 2004/0103831 | A1 | 6/2004 | Pope |
| 2004/0244289 | A1 | 12/2004 | Morozumi et al. |
| 2005/0000162 | A1 | 1/2005 | Bishop et al. |
| 2006/0165582 | A1 | 7/2006 | Brooker et al. |
| 2006/0219139 | A1 | 10/2006 | Pope et al. |
| 2006/0251547 | A1 | 11/2006 | Windes et al. |
| 2006/0265954 | A1 | 11/2006 | Dogru et al. |
| 2007/0051043 | A1 | 3/2007 | Schingnitz et al. |
| 2007/0204512 | A1 | 9/2007 | Self et al. |
| 2008/0081844 | A1 | 4/2008 | Shires et al. |
| 2008/0110090 | A1 | 5/2008 | Zawadzki |
| 2008/0147241 | A1 | 6/2008 | Tsangaris et al. |
| 2009/0093600 | A1 | 4/2009 | Moore et al. |
| 2009/0107046 | A1 | 4/2009 | Leininger |
| 2009/0151251 | A1 | 6/2009 | Manzer et al. |
| 2009/0217587 | A1 | 9/2009 | Raman et al. |
| 2009/0217588 | A1 | 9/2009 | Hippo et al. |
| 2009/0320368 | A1 | 12/2009 | Castaldi |
| 2009/0321317 | A1 | 12/2009 | Widmer et al. |
| 2010/0038594 | A1 | 2/2010 | Bohlig et al. |
| 2010/0042557 | A1 | 2/2010 | Block et al. |
| 2010/0083575 | A1 | 4/2010 | Varadaraj |
| 2010/0139534 | A1 | 6/2010 | Tsantrizos |
| 2010/0186291 | A1 | 7/2010 | Yie et al. |
| 2010/0298449 | A1 | 11/2010 | Rojey |
| 2011/0185624 | A1 | 8/2011 | Hall |
| 2011/0282049 | A1 | 11/2011 | Shelton et al. |
| 2011/0290637 | A1 | 12/2011 | Kumar |
| 2012/0032452 | A1 | 2/2012 | Kuku |
| 2012/0238741 | A1 | 9/2012 | Buchanan et al. |
| 2013/0082210 | A1 | 4/2013 | Gautam et al. |
| 2013/0143973 | A1 * | 6/2013 | Townsend .............. B01J 23/626 518/703 |
| 2013/0269252 | A1 | 10/2013 | Tsangaris et al. |
| 2014/0091258 | A1 | 4/2014 | Robinson |
| 2014/0290593 | A1 | 10/2014 | Krammer |
| 2015/0005398 | A1 | 1/2015 | Chakravarti et al. |
| 2015/0096222 | A1 | 4/2015 | Calabrese et al. |
| 2015/0211736 | A1 | 7/2015 | Bohlig et al. |
| 2015/0232771 | A1 | 8/2015 | Bell et al. |
| 2015/0337206 | A1 | 11/2015 | Iwasa |
| 2016/0122672 | A1 | 5/2016 | White |
| 2016/0160138 | A1 | 6/2016 | Kowoll et al. |
| 2017/0088783 | A1 | 3/2017 | Nawrocki |
| 2017/0218284 | A1 | 8/2017 | Liss |
| 2017/0312718 | A1 | 11/2017 | Tawfik |
| 2018/0215914 | A1 | 8/2018 | Orts |
| 2019/0010050 | A1 | 1/2019 | Chandran et al. |
| 2020/0247910 | A1 | 8/2020 | Sheppard et al. |
| 2020/0248082 | A1 | 8/2020 | Trapp et al. |
| 2020/0248085 | A1 | 8/2020 | Trapp et al. |
| 2020/0248086 | A1 | 8/2020 | Trapp et al. |
| 2022/0213397 | A1 | 7/2022 | Trapp et al. |

FOREIGN PATENT DOCUMENTS

| | | | |
|---|---|---|---|
| CN | 101735011 | A | 6/2010 |
| CN | 201626935 | U | 11/2010 |
| CN | 101805636 | B | 7/2013 |
| CN | 203582812 | U | 5/2014 |
| CN | 203923112 | U | 11/2014 |
| CN | 104212471 | A | 12/2014 |
| CN | 104629806 | A | 5/2015 |
| CN | 103205279 | B | 7/2015 |
| CN | 105219437 | A | 1/2016 |
| CN | 105299712 | A | 2/2016 |
| CN | 103979491 | B | 7/2016 |
| CN | 106381181 | A | 2/2017 |
| CN | 106947509 | A | 7/2017 |
| CN | 104789268 | B | 12/2017 |
| CN | 107497467 | A | 12/2017 |
| CN | 105462615 | B | 4/2018 |
| CN | 105779017 | B | 7/2018 |
| CN | 108557760 | A | 9/2018 |
| CN | 110848697 | A | 2/2020 |
| CN | 112226255 | A | 9/2020 |
| DE | 42 00 341 | A1 | 5/1993 |
| DE | 44 36 226 | A1 | 4/1996 |
| DE | 44 46 803 | A1 | 6/1996 |
| DE | 10 2016 002 029 | B4 | 10/2018 |
| EP | 0 148 542 | A1 | 1/1984 |
| EP | 0 257 019 | A2 | 2/1988 |
| EP | 0 380 848 | B1 | 8/1989 |
| EP | 648828 | B1 | 9/1994 |
| EP | 682590 | B1 | 11/1995 |
| EP | 1 462 505 | A1 | 9/2004 |
| EP | 3 390 585 | A1 | 10/2018 |
| EP | 3 392 563 | A1 | 10/2018 |
| EP | 3 397 733 | A1 | 11/2018 |
| GB | 2556665 | A | 6/2018 |

(56) References Cited

FOREIGN PATENT DOCUMENTS

| | | | |
|---|---|---|---|
| JP | 05-208183 | A | 8/1993 |
| JP | 07-062353 | A | 3/1995 |
| JP | 07-308922 | A | 11/1995 |
| JP | 10-236801 | A | 9/1998 |
| JP | 10-310783 | A | 11/1998 |
| JP | 11-080746 | A | 3/1999 |
| JP | 2000-303084 | A | 10/2000 |
| JP | 2000-328070 | A | 11/2000 |
| JP | 2002-038172 | A | 2/2002 |
| JP | 2003-238966 | A | 8/2003 |
| JP | 2003-246989 | A | 9/2003 |
| JP | 2004-315639 | A | 11/2004 |
| JP | 2005-120205 | A | 5/2005 |
| JP | 2006-328328 | A | 12/2006 |
| JP | 3980426 | B2 | 7/2007 |
| JP | 2008-063185 | A | 3/2008 |
| JP | 2008-249212 | A | 10/2008 |
| JP | 2009-235189 | A | 10/2009 |
| JP | 2009-300006 | A | 12/2009 |
| JP | 2011-006619 | A | 1/2011 |
| JP | 2017-180922 | A | 10/2017 |
| JP | 2017-193676 | A | 10/2017 |
| JP | 2017-195742 | A | 10/2017 |
| JP | 6280484 | B2 | 2/2018 |
| JP | 2018-043224 | A | 3/2018 |
| JP | 2018-053012 | A | 4/2018 |
| JP | 2018-123184 | A | 8/2018 |
| JP | 2018-123689 | A | 8/2018 |
| KR | 10-1195417 | B1 | 10/2012 |
| KR | 10-1721823 | B1 | 4/2017 |
| WO | WO 94/17161 | A1 | 8/1994 |
| WO | WO 2009/158486 | A1 | 12/2009 |
| WO | WO 2017/080933 | A1 | 5/2017 |
| WO | WO 2017/103527 | A1 | 6/2017 |
| WO | WO 2017/115019 | A1 | 7/2017 |
| WO | WO 2018/052337 | A1 | 3/2018 |
| WO | WO 2018/160588 | A1 | 9/2018 |

OTHER PUBLICATIONS

Lopez et al, Renewable and Sustainable Energy Reviews, 2018, 82, p. 576-596.*

ASTMD6400; "Standard Specification for Labeling of Plastics Designed to be Aerobically Composted in Municipal or Industrial Facilities"; Dec. 2021.

ASTMD6474; "Standard Test Method for Determining Molecular Weight Distribution and Molecular Weight Averages of Polyolefins by High Temperature Gel Permeation Chromatography"; Apr. 1, 2020.

ASTMF876; Standard Specification for Crosslinked Polyethylene (PEX) Tubing; Apr. 2022.

Agrawal; "Compositional Analysis of Solid Waste and Refuse Derived Fuels by Thermogravimetry;" Compositional Analysis by Thermogravimetry; ASTM STP 997; C.M. Earnest, Ed.; American Society for Testing and Materials; Philadelphia; 1988; pp. 259-271.

Alter; "The Origins of Municipal Solid Waste: The Relations Between Residues from Packaging Materials and Food;" Waste Management & Research; Jul. 1989; pp. 103-114.

Ashida et al.; "Co-pyrolysis of hydrothermally upgraded brown coal and waste plastics;" The Japan Institute of Energy; pp. 97-98.

Barton; "Processing of Urban Waste to Provide Feedstock for Fuel/Energy Recovery;" CEC International Conference, Pyrolysis and Gasification; Luxembourg; Warren Spring Lab Report No. W89026; May 1989; pp. 57-71.

Behzadi et al.; "Liquid Fuel from Plastic Wastes Using Extrusion—Rotary Kiln Reactors;" Chapter 19; Feedstock Recycling and Pyrolysis of Waste Plastics: Converting Waste Plastics into Diesel and Other Fuels; 2006; pp. 531-548.

Bhaskar et al.; "Pyrolysis studies of PP/PE/PS/PVC/HIPS-Br plastics mixed with PET and dehalogenation (Br, Cl) of the liquid products;" J. Anal. Appl. Pyrolysis; 72; 2004; pp. 27-33.

Blazsó; "Recent trends in analytical and applied pyrolysis of polymers;" Journal of Analytical and Applied Pyrolysis; 39; 1997; pp. 1-25.

Brems, Anke, et al.; "Gasification of plastic waste as waste-to-energy or wate-to-syngas recovery route"; Natural Science, 2013, vol. 5, No. 6, pp. 695-704.

Campbell et al.; "The potential for adding plastic waste fuel at a coal gasification power plant;" Waste Manage Res; 2001; 19; ; pp. 526-532.

De Marco et al.; "Recycling polymeric wastes by means of pyrolysis;" J Chem Technol Biotechnol; 77; online: 2002; pp. 817-824.

Elam et al.; "An Integrated Approach to the Recovery of Fuels and Chemicals from Mixed Waste Carpets Through Thermocatalytic Processing;" American Chemical Society, Division of Fuel Chemistry; 1997; 42(4); pp. 993-997.

Encyclopedia of Polymer Science and Technology; Copyright John Wiley & Sons, Inc.; vol. 7; pp. 657-678.

Feng et al.; "Pyrolysis Characteristics and Kinetics of Waste Plastics and Coal Powder;" Journal of Iron and Steel Research; vol. 18; No. 11; Nov. 2006; pp. 11-14, 26.

Fernandez; "La Recuperacion de Los Residuos Plasticos;" Ingenieria Quimica; Octubre 1997; pp. 153-157.

Fernandez; "Reciclado Quimico de Plasticos;" Revista de Plasticos Modernos; No. 477; Marzo 96; pp. 290-301.

García et al.; "Comparison between product yields in the pyrolysis and combustion of different refuse;" J. Anal. Appl. Pyrolysis; 68-69; 2003; pp. 577-598.

Helt et al.; "Liquids from Municipal Solid Waste;" Chapter 8; Soltes and Milne; Pyrolysis Oils from Biomass; ACS Symposium Series; American Chemical Society; Washington, DC; 1988; pp. 79-91.

Huczko et al.; "Plasma Gasification of Surrogate and Real Waste Plastics;" Thermal Solid Waste Utilisation in Regular and Industrial Facilities; 2000; pp. 155-165.

Hujuri et al.; "Modeling pyrolysis kinetics of plastic mixtures;" Polymer Degradation and Stability; 93; 2008; pp. 1832-1837.

Jung; "Pyrolysis and Gasification of Industrial Waste Towards Substitution Fuels Valorisation;" High Temperature Materials and Process Special Issue; vol. 27; No. 5; 2008; pp. 299-304.

Kaminsky; "Chemical Recycling of Mixed Plastics by Pyrolysis;" Advances in Polymer Technology; vol. 14; No. 4; 1995; pp. 337-344.

Kaminsky et al.; "Olefins from polyolefins and mixed plastics by pyrolysis;" Journal of Analytical and Applied Pyrolysis; 32; 1995; pp. 19-27.

Kaminsky et al.; "Pyrolysis of Plastic Waste and Scrap Tires Using a Fluidized-Bed Process;" Chapter 31; Jones and Radding; Thermal Conversion of Solid Wastes and Biomass; ACS Symposium Series; American Chemical Society; Washington, DC; 1995; pp. 423-439.

Kelly et al.; "A Low Cost and High Quality Solid Fuel From Biomass and Coal Fines;" Final Report; DOE Contract No. DE-AC26-99FT40157; Mar. 1, 1999 to May 31, 2000; Altex Technologies Corporation; Jul. 2001; pp. 1-122.

Kim et al.; "Pyrolysis of a fraction of mixed plastic wastes depleted in PVC;" Journal of Analytical and Applied Pyrolysis; 40-41; 1997; pp. 365-372.

Lin; "Recycling Technology of Poly(ethylene Terephthalate) Materials;" Macromol. Symp.; 135; 1998; pp. 129-135.

Lopez et al.; "Recent advances in the gasification of waste plastics. A critical overview;" Renewable and Sustainable Energy Reviews, 82, (2018), pp. 576-596.

Luska et al.; "Piroliza jako jedna z metod recyklingu odpadow polimerowych;" Elastomery; Nr 5; pp. 30-36.

Mackey; "A Review of Advanced Recycling Technology;" Chapter 14; Rader et al.; Plastics, Rubber, and Paper Recycling; ACS Symposium Series; American Chemical Society; Washington, DC; 1995; pp. 161-169.

Mallya et al.; "Effects of Feedstock Components on Municipal Solid Waste Pyrolysis;" A.V. Bridgwater et al. (eds.), Research in Thermochemical Biomass Conversion; 1988; pp. 111-126.

Notification of Transmittal of The International Search Report and The Written Opinion of the International Searching Authority, or the

(56) References Cited

OTHER PUBLICATIONS

Declaration with Date of Mailing May 29, 2020 received in International Application No. PCT/US2020/016483 with a filing date of Feb. 4, 2020.
Notification of Transmittal of The International Search Report and The Written Opinion of the International Searching Authority, or the Declaration with Date of Mailing Jun. 12, 2020 received in International Application No. PCT/US2020/016479 with a filing date of Feb. 4, 2020.
Notification of Transmittal of The International Search Report and The Written Opinion of the International Searching Authority, or the Declaration with Date of Mailing Aug. 14, 2020 received in International Application No. PCT/US2020/016477 with a filing date of Feb. 4, 2020.
Okuwaki; "Feedstock recycling of plastics in Japan;" Polymer Degradation and Stability; 85; 2004; pp. 981-988.
Parra et al.; "Textural characterization of activated carbons obtained from poly(ethylene terephthalate) by carbon dioxide activation;" Studies in Surface Science and Catalysis; 144; pp. 537-543.
Parra et al.; "Textural development and hydrogen adsorption of carbon materials from PET waste;" Journal of Alloys and Compounds; 379; 2004; pp. 280-289.
Piao et al.; "Research and Development on Gasification Technology of Organic Waste Material (OWM) by using Entrained-Flow;" Journal of the Japan Institute of Energy; 82; 2003; pp. 671-678.
Pober et al.; "The Nature of Pyrolytic Oil from Municipal Solid Waste;" Chapter V; Fuels Waste; 1977; pp. 73-85.
Probert et al.; "Harnessing Energy from Domestic, Municipal and Industrial Refuse;" Applied Energy; 27; 1987; pp. 89-168.
Ra et al.; "Entrained-Flow Coal Water Slurry Gasification;" Korean Chem. Eng. Res.; vol. 48; No. 2; Apr. 2010; pp. 129-139.
Rago et al.; "Torrefaction of textile waste for production of energy-dense biochar using mass loss as a synthetic indicator;" Journal of Environmental Chemical Engineering; Jun. 2018; pp. 811-822.
Roy et al.; "Preliminary Feasibility Study of the Biomass Vacuum Pyrolysis Process;" A.V. Bridgwater et al. (eds.); Research in Thermochemical Biomass Conversion; pp. 585-596.
Saha et al.; "Model-free method for isothermal and non-isothermal decomposition kinetics analysis of PET sample;" Thermochimica Acta; 444; 2006; pp. 46-52.
San José et al.; "Fluidodinamica de Los Lechos de Borbor Conicos (Spouted Beds) Para el Tratamiento de REsiduos de Materiales Plasticos;" Informacion Tecnologica; vol. 13; No. 5; 2002; pp. 21-24.
Savage et al.; "Screening Shredded Municipal Solid Waste;" Compost Science Journal of Waste Recycling; Jan./Feb. 1976; pp. 7-11.
Senneca et al.; "Oxidative pyrolysis of solid fuels;" J. Anal. Appl. Pyrolysis; 71; 2004; pp. 959-970.
Shah et al.; "Conversion of Waste Plastic to Oil: Direct Liquefaction versus Pyrolysis and Hydroprocessing;" Energy & Fuels; 13; 1999; pp. 832-838.
Shoji et al.; "Thermal weight analysis of the jet floor gasification process of wasteTen;" Journal of Chemical Engineering; pp. 27-34 (machine translation).
Shoji et al.; "Waste plastics recycling by an entrained-flow gasifier;" J Mater Cycles Waste Manag; Mar. 2001; pp. 75-81.
Straka et al.; "Co-pyrolysis of Waste Polymers with Coal;" Macromol. Symp.; 135; 1998; pp. 19-23.
Vasile et al.; "Thermal and catalytic decomposition of mixed plastics;" Journal of Analytical and Applied Pyrolysis; 57; 2001; pp. 287-303.
Vivero et al.; "Effects of plastic wastes on coal pyrolysis behavior and the structure of semicokes;" J. Anal. Appl. Pyrolysis; 74; 2005; pp. 327-336.
Wilkins et al.; "Review of pyrolysis and combustion products of municipal and industrial wastes;" Journal of Environmental Science & Health Part A; 18:6; 1983; pp. 747-772.
Williams et al.; "Interaction of Plastics in Mixed-Plastics Pyrolysis;" Energy & Fuels; 13; 1999; pp. 188-196.
Williams et al.; "The Pyrolysis of Individual Plastics and a Plastic Mixture in a Fixed Bed Reactor;" J. Chem. Tech. Biotechnol.; 70; 1997; pp. 9-20.
Williams et al.; "The pyrolysis of municipal solid waste;" Journal of the Institute of Energy; Dec. 1992; 65; pp. 192-200.
Williams et al.; "Recycling plastic waste by pyrolysis;" Journal of the Institute of Energy; Jun. 1998; 71; pp. 81-93.
Zhiyuan et al.; "The release law of benzene, radon and fife in the process of pyrococosatic and plastic pyrolytic process;" Environmental Chemistry; vol. 27; No. 6; Nov. 2008; pp. 766-769 (machine translation).
Co-pending U.S. Appl. No. 16/780,005, filed Feb. 3, 2020; Trapp et al.
Co-pending U.S. Appl. No. 16/780,012, filed Feb. 3, 2020; Trapp et al.
USPTO Office Action dated Jun. 30, 2021 in co-pending U.S. Appl. No. 16/780,012.
USPTO Office Action dated Oct. 20, 2021 in co-pending U.S. Appl. No. 16/780,012.
Co-pending U.S. Appl. No. 16/779,999, filed Feb. 3, 2020; Trapp et al.
USPTO Office Action dated May 3, 2021 in co-pending U.S. Appl. No. 16/779,999.
Notice of Allowance received from USPTO on Mar. 21, 2022 in U.S. Co-pending U.S. Appl. No. 16/779,999.
Co-pending U.S. Appl. No. 16/779,977, filed Feb. 3, 2020; Trapp et al.
USPTO Office Action dated Sep. 28, 2021 in co-pending U.S. Appl. No. 16/779,977.
USPTO Notice of Allowance dated May 11, 2022 received in co-pending U.S. Appl. No. 16/779,977.
ASTMD5399; "Standard Test Method for Boiling Point Distribution of Hydrocarbon Solvents by Gas Chromatography"; Published Dec. 2017.
Notification of Transmittal of The International Search Report and The Written Opinion of the International Searching Authority, or the Declaration with Date of Mailing Jul. 30, 2021 received in International Application No. PCT/US2021/027001.
Notification of Transmittal of The International Search Report and The Written Opinion of the International Searching Authority, or the Declaration with Date of Mailing Jul. 30, 2021 received in International Application No. PCT/US2021/026987.
Notification of Transmittal of The International Search Report and The Written Opinion of the International Searching Authority, or the Declaration with Date of Mailing Aug. 4, 2021 received in International Application No. PCT/US2021/027009.
Notification of Transmittal of The International Search Report and The Written Opinion of the International Searching Authority, or the Declaration with Date of Mailing Jul. 30, 2021 received in International Application No. PCT/US2021/026994.
Notification of Transmittal of The International Search Report and The Written Opinion of the International Searching Authority, or the Declaration with Date of Mailing Jan. 4, 2021 received in International Application No. PCT/US2020/052401.
USPTO Office Action dated Sep. 21, 2021 in co-pending U.S. Appl. No. 16/780,005.
Cheng, H.N., et al.; "Conversion of cotton byproducts to mixed cellulose esters"; Carbohydrate Polymers 86 (2011), pp. 1130-1136.
Notice of Allowance received from USPTO on Feb. 25, 2022 in U.S. Co-pending U.S. Appl. No. 16/780,005.
Shelton, Michael C.; Cellulose Esters, Inorganic Esters; Kirk-Othmer Encyclopedia of Chemical Technology; vol. 5, (2004), pp. 394-444.
USPTO Office Action dated Nov. 22, 2022 in co-pending U.S. Appl. No. 17/651,185.
USPTO Office Action dated Dec. 13, 2022 in co-pending U.S. Appl. No. 17/656,044.
Co-pending U.S. Appl. No. 17/819,963, filed Aug. 16, 2022.
Co-pending U.S. Appl. No. 17/663,684, filed May 17, 2022; Trapp et al. Publication No. 2022-0275298.
Co-pending U.S. Appl. No. 17/656,044, filed Mar. 23, 2022; Trapp et al.

(56) References Cited

OTHER PUBLICATIONS

Wang, Yun-Qi, et al.; Enhancement of acetate productivity in a thermophilic (55○C) hollow-fiber membrane biofilm reactor with mixed culture syngas (H2/CO2) fermentation; Appl Microbiol Biotechnol; (2017), 101, pp. 2619-2627.
European Search Report—Application No. 20868744.2 with a date of Sep. 11, 2023.
USPTO Office Action dated Dec. 12, 2023 in co-pending U.S. Appl. No. 17/656,044.

* cited by examiner

CELLULOSE ESTER COMPOSITIONS DERIVED FROM RECYCLED CELLULOSE ESTER CONTENT SYNGAS

CROSS-REFERENCE TO RELATED APPLICATION(S)

This application is a national stage filing under 35 USC § 371 of International Application Number PCT/US2020/052401, filed on, Sep. 24, 2020 which claims the benefit of the filing date to U.S. Provisional Application No. 62/907,139, filed on Sep. 27, 2019, the entire disclosures of which are incorporated by reference herein.

BACKGROUND OF THE INVENTION

There is a well-known global issue with waste disposal, particularly of large volume consumer products such as plastics, plastics, textiles and other polymers that are not considered biodegradable within acceptable temporal limits. There is a public desire to incorporate these types of wastes into renewed products through recycling, reuse, or otherwise reducing the amount of waste in circulation or in landfills.

There is a market need for consumer products in general to contain significant amounts of renewable, recycled, re-used, biodegradable or other materials that will reduce carbon emissions, waste disposal and other environmental sustainability issues.

It would be beneficial to provide products having significant content of renewable, recycled, re-used and biodegradable material.

SUMMARY OF THE INVENTION

Cellulose ester ("CE") is a renewable material in that the back bone of the molecule is cellulose. However, the organic acid groups attached to the cellulose backbone that make it an ester and affect the properties of the material are generally made from fossil fuels (e.g., oil, natural gas, coal). The present invention offers a way to include both renewable and recycled content in cellulose esters by providing cellulose esters that are made from cellulose and organic compounds, e.g., acids, derived from recycled, reused or other environmentally favored raw material. In an aspect, the recycled content in the cellulose ester is at least partially derived from recycled cellulose ester, providing a closed loop recycling solution.

In one aspect, the invention is directed to a process for preparing a cellulose ester comprising: (1) preparing a recycled CE content syngas in a synthesis gas operation by gasifying a feedstock containing a solid fossil fuel source, at least some content of recycled cellulose ester, and optionally other recycled plastics; (2) using the recycled CE content syngas as a feedstock in a reaction scheme to produce at least one cellulose reactant for preparing a cellulose ester; and (3) reacting said at least one cellulose reactant to prepare at least one cellulose ester.

In another aspect, the invention is directed to use of recycled CE content syngas to produce at least one cellulose reactant. In embodiments, the invention is directed to use of recycled CE content syngas to produce at least one cellulose ester.

In another aspect, a cellulose ester composition is provided comprising at least one cellulose ester having at least one substituent on an anhydroglucose unit (AU) derived at least in part from recycled CE content syngas.

In an aspect, there is provided cellulose ester, cellulose ester composition, fibers (whether filament, staple, tow, bundles, yarn, etc.), articles containing or made with or from cellulose esters (whether textiles or fabrics, filter elements or filaments used in smoking devices, tool handles, ophthalmic product (e.g., eyeglass frames), particles, pellets, sheets, films, coatings, etc.), in each case derived at least in part from recycled CE content syngas (collectively or individually the "Recycle CE"). In embodiments, the Recycle CE comprises a cellulose ester or cellulose ester composition. In embodiments, the Recycle CE is a textile fabric, filament, fiber, tow band, yarn, tool handle, ophthalmic product (e.g. eyeglass frames), filter or tow used in a smoking devices, sheet, film, or coating. In embodiments, the Recycle CE is biodegradable and/or compostable. In embodiments, the Recycle CE is a molded article comprising the cellulose ester. In an embodiment, the molded article is made from a thermoplastic composition comprising the cellulose ester. In an embodiment, the cellulose ester is in the form of a moldable thermoplastic resin.

In embodiments, a staple fiber is provided comprising the cellulose ester composition, wherein the cellulose ester composition comprises cellulose acetate.

In another aspect, the invention is directed to an integrated process for preparing a Recycle CE which comprises the processing steps of: (1) preparing a recycled CE content syngas in a synthesis gas operation utilizing a feedstock that contains a solid fossil fuel source, at least some content of recycled cellulose ester, and optionally other recycled plastics; (2) preparing at least one chemical intermediate from said syngas; (3) reacting said chemical intermediate in a reaction scheme to prepare at least one cellulose reactant for preparing a Recycle CE, and/or selecting said chemical intermediate to be at least one cellulose reactant for preparing a Recycle CE; and (4) reacting said at least one cellulose reactant to prepare said Recycle CE; wherein said Recycle CE comprises at least one substituent on an anhydroglucose unit (AGU) derived from recycled CE content syngas.

In embodiments, the processing steps (1) to (4) are carried out in a system that is in fluid and/or gaseous communication.

In embodiments, the recycled CE content syngas can be provided by a process for the production of syngas comprising:

a. charging an oxidant and a feedstock composition to a gasification zone within a gasifier, said feedstock composition comprising a solid fossil fuel and up to 25 wt. %, or up to 20 wt. %, or up 15 wt. %, or up to 12 wt. %, or up to 10 wt. %, or up to 7 wt. %, or up to 5 wt. %, or less than 5 wt. % recycle total CE and other (optional) plastics based on the weights of solids in the feedstock composition;
b. gasifying the feedstock composition together with the oxidant in a gasification zone to produce a syngas composition; and
c. discharging at least a portion of the syngas composition from the gasifier;

wherein the gasifier is an entrained flow gasifier.

In embodiments, the recycled CE content syngas can be provided by a process for the production of syngas comprising:

a. charging an oxidant and a feedstock composition to a gasification zone within a gasifier, said feedstock composition comprising a solid fossil fuel and 90 wt. % of the CE and plastics having a particle size in the largest dimension of not more than 2 mm;

b. gasifying the feedstock composition together with the oxidant in a gasification zone to produce a syngas composition; and c. discharging at least a portion of the syngas composition from the gasifier;

wherein the gasifier is an entrained flow gasifier.

In embodiments, it is desirable that the feedstock is a slurry. In embodiments, the recycled CE content syngas can be provided by a process for the production of syngas comprising:

a. charging an oxidant and a feedstock slurry composition to a gasification zone within a gasifier, said feedstock slurry composition comprising CE (optionally other plastics), a solid fossil fuel, and water, wherein either (i) the amount of CE and plastics are up to 25 wt. %, or up to 20 wt. %, or up 15 wt. %, or up to 12 wt. %, or up to 10 wt. %, or up to 7 wt. %, or up to 5 wt. %, or less than 5 wt. % based on the weight of the solids in the feedstock slurry or (ii) 90 wt. % of the CE and plastics have a particle size in the largest dimension of not more than 2 mm;

b. gasifying the feedstock composition together with the oxidant in a gasification zone to produce a syngas composition; and c. discharging at least a portion of the syngas composition from the gasifier, wherein at least one of the following conditions is present:

(i) gasification within the gasification zone is conducted at a temperature of at least 1000° C., or (ii) the pressure within the gasification zone greater than 2.7 MPa, or (iii) the feedstock composition is a slurry, or (iv) no steam is introduced to the gasifier that flows into the gasification zone, or (v) the recycled CE/plastics are pre-ground such that at least 90% of the particles have a particle size of less than 2 mm, or (vi) the tar yield is less than 4 wt. %, or (vii) the gasifier contains no membrane wall in the gasification zone, or (viii) a combination of two or more of the above conditions.

In embodiments, the recycled CE content syngas can be produced from a feedstock slurry composition comprising CE (optional other plastics), a solid fossil fuel, and water, wherein the CE and plastics have a particle size of not more than 2 mm, and the solid fossil fuel in the feedstock composition has a particle size of less than 2 mm, the solids content in the slurry is at least 62 wt. % (or at least 65 wt. %, or at least 68 wt. %, or at least 69 wt. %, or at least 70 wt. %), the amount of CE and plastics present in the feedstock stream slurry composition is 0.1 wt. % up to 25 wt. %, or up to 20 wt. %, or up 15 wt. %, or up to 12 wt. %, or up to 10 wt. %, or up to 7 wt. %, or up to 5 wt. %, or less than 5 wt. % based on the weight of all solids, and the water is at least 20 wt. % based on the weight of the feedstock slurry composition, and wherein either:

a. the slurry is stable as determined by having an initial viscosity of 100,000 cP or less at 5 minutes, or 10 minutes, or 15 minutes, or 20 minutes, or 25 minutes, or even for 30 minutes using a Brookfield R/S Rheometer equipped with V80-40 vane operating at a shear rate of 1.83/s or a Brookfield viscometer with an LV-2 spindle rotating at a rate of 0.5 rpm, measured at ambient conditions; or b. the slurry is pumpable as determined by having a viscosity of less than 30,000 cP, or 25,000 cP or less, or not more than 23,000 cP, or not more than 20,000 cP, or not more than 18,000 cP, or not more than 15,000 cP, or not more than 13,000 cP, after mixing to obtain a homogeneous distribution of solids throughout the slurry and using a Brookfield R/S Rheometer equipped with V80-40 vane operating at a shear rate of 1.83/s or a Brookfield viscometer with an LV-2 spindle rotating at a rate of 0.5 rpm Brookfield R/S Rheometer equipped with V80-40 vane operating at a shear rate of 1.83/s or a Brookfield viscometer with an LV-2 spindle rotating at a rate of 0.5 rpm Brookfield R/S Rheometer equipped with V80-40 vane operating at a shear rate of 1.83/s or a Brookfield viscometer with an LV-2 spindle rotating at a rate of 0.5 rpm, measured at ambient conditions, or c. both.

In embodiments, the recycled CE content syngas can comprise a syngas composition discharged from a gasifier and obtained by gasifying a feedstock stream comprising CE (and optional other plastics) and solid fossil fuel, wherein either (i) the amount of CE and plastics are up to 25 wt. %, or up to 20 wt. %, or up 15 wt. %, or up to 12 wt. %, or up to 10 wt. %, or up to 7 wt. %, or up to 5 wt. %, or less than 5 wt. % based on the weight of solids in the feedstock stream, or (ii) wherein the CE and plastics have a particle size of not more than 2 mm, or (iii) both, and said syngas stream contains no tar or less than 4 wt. % (or less than 3 wt. %, or not more than 2 wt. %, or not more than 1 wt. %, or not more than 0.5 wt. %, or not more than 0.2 wt. %, or not more than 0.1 wt. %, or not more than 0.08 wt. %, or not more than 0.05 wt. %, or not more than 0.02 wt. %, or not more than 0.01 wt. %, or nor more than 0.005 wt. %) tar, based on the weight of all condensable solids in the syngas composition.

In embodiments, the recycled CE content syngas can comprise a syngas composition stream produced by gasifying in a gasifier a feedstock comprising solid fossil fuel, CE and other plastics (Mixed Feed) having a compositional variability that is 5% or less measured over a time period that is the lesser of 12 days or feeding the Mixed Feed to the gasifier, said syngas compositional variability is measured and satisfied against at least one of the following gaseous compounds (in moles):

a. CO amount, or
b. H2 amount, or
c. CO2 amount, or
d. CH4 amount, or
e. H2S amount, or
f. COS amount, or
g. H2+CO amount, or its molar ratio in sequence (e.g. H2:CO ratio), or
h. H2+CO+CO2 amount, or its molar ratio in sequence, or
i. H2+CO+CH4 amount, or its molar ratio in sequence, or
j. H2+CO+CO2+CH4 amount, or its molar ratio in sequence, or
k. H2S+COS amount, or its molar ratio in sequence, or
l. $H2+CO+CO_2+CH_4+H_2S+COS$.

In embodiments, the recycled CE content syngas can comprise a syngas composition stream having a switching variability that is negative, zero, or not more than 15%, wherein the switching frequency is at least 1×/2 years and the switching variability is determined by the following equation:

$$\% SV = \frac{V_m - V_{ff}}{V_{ff}} \times 100$$

where % SW is percent syngas switching variability on one or more measured ingredients in the syngas composition; and $V_m$ is the syngas compositional variability of a gaseous compound(s) using a mixed stream containing CE (and optional plastics) and the fossil fuel; and $V_{ff}$ is the syngas compositional variability of the same gaseous compound(s) using a fossil fuel only stream, and where the solids concentration is the same in both cases, the fossil fuel is the same in both cases, and the feedstocks are gasified under the same conditions, other than temperature fluctuations which may autogenously differ as a result of having CE and plastics in the feedstock, and the variabilities are measured and satisfied against at least one of the following gaseous compounds (in moles):

a. CO amount, or
b. $H_2$ amount, or
c. CO2 amount, or
d. CH4 amount, or
e. H2S amount, or
f. COS amount, or
g. H2+CO amount, or its molar ratio in sequence (e.g. H2:CO ratio), or
h. H2+CO+CO2 amount, or its molar ratio in sequence, or
i. H2+CO+CH4 amount, or its molar ratio in sequence, or
j. H2+CO+CO2+CH4 amount, or its molar ratio in sequence, or
k. H2S+COS amount, or its molar ratio in sequence, or
l. H2+CO+$CO_2$+$CH_4$+$H_2S$+COS.

In embodiments, the process for preparing a cellulose ester is a closed loop process. In one embodiment, at least a portion of the recycled CE content syngas is used to make a cellulose ester material, and at least a portion of the feedstock to the gasifier is obtained from the same cellulose ester material type. In one embodiment, at least a portion of the recycled CE content syngas is used to make a cellulose ester material, for use in an article, through one or more intermediate products, at least one of which is made at least in part from the syngas, and at least a portion of the feedstock to the gasifier is obtained from the same article type.

In one embodiment, the cellulose ester material is cellulose acetate or cellulose diacetate. In one embodiment, the article is sheet material containing cellulose acetate or cellulose diacetate. In one embodiment, the article is an ophthalmic article, e.g., eyeglass frames.

DETAILED DESCRIPTION OF THE INVENTION

Cellulose Esters

Figure 1:
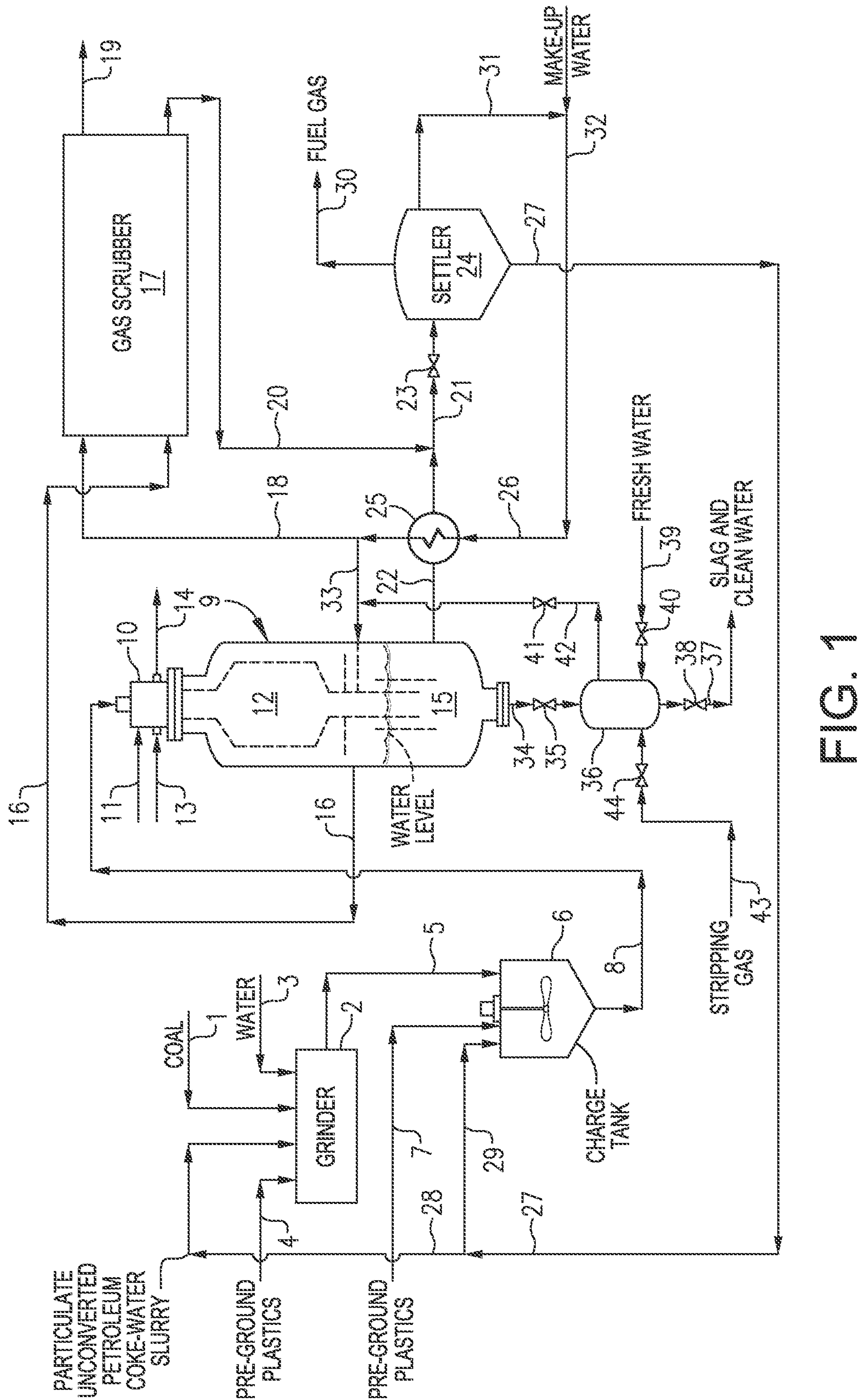
FIG. 1 is a schematic plant design for combining CE/plastics and solid fossil fuel as a feedstock to a gasification process to produce syngas.

In one embodiment or in combination with any of the mentioned embodiments, a recycle cellulose ester or a recycle cellulose ester composition (a Recycle CE) comprising at least one recycle cellulose ester is provided, wherein the cellulose ester has at least one substituent on an anhydroglucose unit (AU) derived from recycled CE content syngas. As used herein, a Recycle CE is a term used for convenience to refer to cellulose esters and composition in which at least one substituent on an anhydroglucose unit (AU) is derived from recycled CE content syngas.

In embodiments, the cellulose ester utilized in this invention can be any that is known in the art. Cellulose esters that can be used for the present invention generally comprise repeating units of the structure:

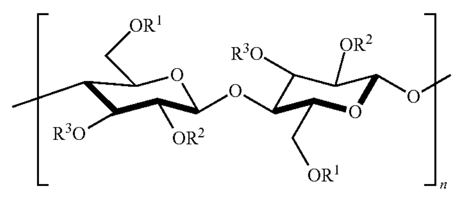

wherein $R^1$, $R^2$, and $R^3$ are selected independently from the group consisting of hydrogen or straight chain alkanoyl having from 2 to 10 carbon atoms. For cellulose esters, the substitution level is usually express in terms of degree of substitution (DS), which is the average number of non-OH substitutents per anhydroglucose unit (AGU). Generally, conventional cellulose contains three hydroxyl groups in each AGU unit that can be substituted; therefore, DS can have a value between zero and three. However, low molecular weight cellulose mixed esters can have a total degree of substitution slightly above 3 due to end group contributions. Native cellulose is a large polysaccharide with a degree of polymerization from 250-5,000 even after pulping and purification, and thus the assumption that the maximum DS is 3.0 is approximately correct. However, as the degree of polymerization is lowered, as in low molecular weight cellulose mixed esters, the end groups of the polysaccharide backbone become relatively more significant, thereby resulting in a DS that can range in excess of 3.0. Low molecular weight cellulose mixed esters are discussed in more detail subsequently in this disclosure. Because DS is a statistical mean value, a value of 1 does not assure that every AGU has a single substitutent. In some cases, there can be unsubstituted anhydroglucose units, some with two and some with three substitutents, and typically the value will be a non-integer. Total DS is defined as the average number of all of substituents per anhydroglucose unit. The degree of substitution per AGU can also refer to a particular substitutent, such as, for example, hydroxyl, acetyl, butyryl, or propionyl.

In embodiments, the cellulose ester utilized can be a cellulose triester or a secondary cellulose ester. Examples of cellulose triesters include, but are not limited to, cellulose triacetate, cellulose tripropionate, or cellulose tributyrate. Examples of secondary cellulose esters include cellulose acetate, cellulose acetate propionate, and cellulose acetate butyrate.

In one embodiment or in combination with any of the mentioned embodiments, the cellulose ester can be chosen from cellulose acetate (CA), cellulose propionate (CP), cellulose butyrate (CB), cellulose acetate propionate (CAP), cellulose acetate butyrate (CAB), cellulose propionate butyrate (CPB), and the like, or combinations thereof.

Examples of such cellulose esters are described in U.S. Pat. Nos. 1,698,049; 1,683,347; 1,880,808; 1,880,560; 1,984, 147, 2,129,052; and 3,617,201, incorporated herein by reference in their entirety to the extent that they do not contradict the statements herein.

In embodiments of the invention, the cellulose esters have at least 2 anhydroglucose rings and can have between at least 50 and up to 5,000 anhydroglucose rings. The number of anhydroglucose units per molecule is defined as the degree of polymerization (DP) of the cellulose ester. In embodiments, n is in a range from 20 to 2,500, or 25 to 2,000, or 25 to 1,000, or 50 to 500, or 50 to 250. In embodiments, cellulose esters can have an inherent viscosity (IV) of about 0.2 to about 3.0 deciliters/gram, or about 0.5 to about 1.8, or about 1 to about 1.5, as measured at a temperature of 25° C. for a 0.25 gram sample in 100 ml of a 60/40 by weight solution of phenol/tetrachloroethane. Examples of cellulose esters include, but are not limited to, cellulose acetate, cellulose diacetate, cellulose propionate, cellulose butyrate, cellulose acetate propionate (CAP), cellulose acetate butyrate (CAB), cellulose propionate butyrate, and the like. In embodiments, cellulose esters useful herein can have a DS/AGU of about 2 to about 2.99, and the substituting ester can comprise acetyl, propionyl, butyryl, or any combinations of these. In another embodiment of the invention, the total DS/AGU ranges from about 2 to about 2.99 and the DS/AGU of acetyl ranges from about 0 to 2.2, with the remainder of the ester groups comprising propionyl, butyryl or combinations thereof.

Cellulose esters can be produced by any method known in the art. Examples of processes for producing cellulose esters are taught in Kirk-Othmer, Encyclopedia of Chemical Technology, 5th Edition, Vol. 5, Wiley-Interscience, New York (2004), pp. 394-444. Cellulose, the starting material for producing cellulose esters, can be obtained in different grades and sources such as from cotton linters, softwood pulp, hardwood pulp, corn fiber and other agricultural sources, and bacterial cellulose, among others.

One method of producing cellulose esters is esterification of the cellulose by mixing cellulose with the appropriate organic acids, acid anhydrides, and catalysts. Cellulose is then converted to a cellulose triester. Ester hydrolysis is then performed by adding a water-acid mixture to the cellulose triester, which can then be filtered to remove any gel particles or fibers. Water is then added to the mixture to precipitate the cellulose ester. The cellulose ester can then be washed with water to remove reaction by-products followed by dewatering and drying.

The cellulose triesters to be hydrolyzed can have three substitutents selected independently from alkanoyls having from 2 to 10 carbon atoms. Examples of cellulose triesters include cellulose triacetate, cellulose tripropionate, and cellulose tributyrate or mixed triesters of cellulose such as cellulose acetate propionate, and cellulose acetate butyrate. These cellulose esters can be prepared by a number of methods known to those skilled in the art. For example, cellulose esters can be prepared by heterogeneous acylation of cellulose in a mixture of carboxylic acid and anhydride in the presence of a catalyst such as H2SO4. Cellulose triesters can also be prepared by the homogeneous acylation of cellulose dissolved in an appropriate solvent such as LiCl/DMAc or LiCl/NMP.

Those skilled in the art will understand that the commercial term of cellulose triesters also encompasses cellulose esters that are not completely substituted with acyl groups. For example, cellulose triacetate commercially available from Eastman Chemical Company, Kingsport, TN, U.S.A., typically has a DS from about 2.85 to about 2.99.

After esterification of the cellulose to the triester, part of the acyl substitutents can be removed by hydrolysis or by alcoholysis to give a secondary cellulose ester. As noted previously, depending on the particular method employed, the distribution of the acyl substituents can be random or non-random. Secondary cellulose esters can also be prepared directly with no hydrolysis by using a limiting amount of acylating reagent. This process is particularly useful when the reaction is conducted in a solvent that will dissolve cellulose. All of these methods yield cellulose esters that are useful in this invention.

In one embodiment or in combination with any of the mentioned embodiments, the secondary cellulose esters useful in the present invention have an absolute weight average molecular weight (Mw) from about 5,000 to about 400,000 as measured by gel permeation chromatography (GPC) according to ASTM D6474. The following method is used to calculate the absolute weight average molecular weight values (Mw) for CE. The solvent is THF stabilized with BHT Preservative. The instrumentation for the THF/cellulose ester procedure consists of the following Agilent 1200 series components: degasser, isocratic pump, auto-sampler, column oven, UV/Vis detector and a refractive index detector. The test temperature is 30° C. and flow rate is 1.0 ml/min. A sample solution of 25 mg cellulose ester in 10 ml THF with BHT preservative and 10 μl toluene flow rate marker is made. The injection volume is 50 μl. The column set is Polymer Laboratories 5 μm PLgel, Guard+Mixed C+Oligopore. The detection is by refractive index. The calibrants are monodisperse polystyrene standards, Mw=580 to 3,220,000 from Polymer Laboratories. The universal calibration parameters are as follows: PS (K=0.0001280 and a=0.7120) and CE (K=0.00007572 and a=0.8424). The universal calibration parameters above were determined by light scattering and viscometery to yield the correct weight average molecular weights. In a further embodiment, the Mw is from about 15,000 to about 300,000. In yet further embodiments, the Mw ranges from about 10,000 to about 250,000; from about 15000 to 200000; from about 20,000 to about 150,000; from about 50,000 to about 150,000, or from about 70,000 to about 120,000.

The most common commercial secondary cellulose esters are prepared by initial acid catalyzed heterogeneous acylation of cellulose to form the cellulose triester. After a homogeneous solution in the corresponding carboxylic acid of the cellulose triester is obtained, the cellulose triester is then subjected to hydrolysis until the desired degree of substitution is obtained. After isolation, a random secondary cellulose ester is obtained. That is, the relative degree of substitution (RDS) at each hydroxyl is roughly equal.

The cellulose esters useful in the present invention can be prepared using techniques known in the art, and can be chosen from various types of cellulose esters, such as for example the cellulose esters that can be obtained from Eastman Chemical Company, Kingsport, TN, U.S.A., e.g., Eastman™ Cellulose Acetate Propionate CAP 482-20, Eastman™ Cellulose Acetate Propionate CAP 141-20, Eastman™ Cellulose Acetate Butyrate CAB 381-20, Cellulose Acetate Butyrate CAB 171-15 and Eastman™ Cellulose Acetate CA 398-30.

In embodiments, the cellulose esters can contain chemical functionality and are described herein as either derivatized, modified, or functionalized cellulose esters. Functionalized cellulose esters can be produced by reacting the free hydroxyl groups of cellulose esters with a bifunctional reactant that has one linking group for grafting to the cellulose ester and one functional group to provide a new chemical group to the cellulose ester. Examples of such bifunctional reactants include succinic anhydride which links through an ester bond and provides acid functionality; mercaptosilanes which links through alkoxysilane bonds and provides mercapto functionality; and isocyanotoethyl methacrylate which links through a urethane bond and gives methacrylate functionality.

In one embodiment or in combination with any of the mentioned embodiments, In one embodiment or in combination with any of the mentioned embodiments, or in combination with any of the mentioned embodiments, of the invention, functionalized cellulose esters are produced by reacting the free hydroxyl groups of the cellulose esters with a bifunctional reactant producing a cellulose ester with at least one functional group selected from the group consisting of unsaturation (double bonds), carboxylic acids, acetoacetate, acetoacetate imide, mercapto, melamine, and long alkyl chains.

Bifunctional reactants to produce cellulose esters containing unsaturation (double bonds) functionality are described in U.S. Pat. Nos. 4,839,230, 5,741,901, 5,871,573, 5,981,738, 4,147,603, 4,758,645, and 4,861,629; all of which are incorporated by reference to the extent they do not contradict the statements herein. In one embodiment or in combination with any of the mentioned embodiments, In one embodiment or in combination with any of the mentioned embodiments, or in combination with any of the mentioned embodiments, the cellulose esters containing unsaturation is produced by reacting a cellulose ester containing residual hydroxyl groups with an acrylic based compound and m-isopropenyl-$\alpha,\alpha'$-dimethylbenzyl isocyanate. The grafted cellulose ester is a urethane-containing product having pendant (meth)acrylate and $\alpha$-methylstyrene moieties. In another embodiment, the cellulose esters containing unsaturation is produced by reacting maleic anhydride and a cellulose ester in the presence of an alkaline earth metal or ammonium salt of a lower alkyl monocarboxylic acid catalyst, and at least one saturated monocarboxylic acid have 2 to 4 carbon atoms. In another embodiment, the cellulose esters containing unsaturation is produced from the reaction product of (a) at least one cellulosic polymer having isocyanate reactive hydroxyl functionality, and (b) at least one hydroxyl reactive poly(alpha, beta ethyleneically unsaturated) isocyanate.

Bifunctional reactants to produce cellulose esters containing carboxylic acid functionality are described in U.S. Pat. Nos. 5,384,163, 5,723,151, and 4,758,645; all of which are incorporated by reference to the extent they do not contradict the statements herein. In one embodiment or in combination with any of the mentioned embodiments, In one embodiment or in combination with any of the mentioned embodiments, or in combination with any of the mentioned embodiments, the cellulose esters containing carboxylic acid functionality are produced by reacting a cellulose ester and a mono- or di-ester of maleic or furmaric acid, thereby obtaining a cellulose derivative having double bond functionality. In another embodiment, the cellulose esters containing carboxylic acid functionality has a first and second residue, wherein the first residue is a residue of a cyclic dicarboxylic acid anhydride and the second residue is a residue of an oleophilic monocarboxylic acid and/or a residue of a hydrophilic monocarboxylic acid. In yet another embodiment, the cellulose esters containing carboxylic acid functionality are cellulose acetate phthalates, which can be prepared by reacting cellulose acetate with phthalic anhydride.

Bifunctional reactants to produce cellulose esters containing acetoacetate functionality are described in U.S. Pat. No. 5,292,877; which is incorporated by reference to the extent it does not contradict the statements herein. In one embodiment or in any of the mentioned embodiments, the cellulose esters containing acetoacetate functionality are produced by contacting: (i) cellulose; (ii) diketene, an alkyl acetoacetate, 2,2,6, trimethyl-4H 1,3-dioxin-4-one, or a mixture thereof, and (iii) a solubilizing amount of solvent system comprising lithium chloride plus a carboxamide selected from the group consisting of 1-methyl-2-pyrolidinone, N,N dimethylacetamide, or a mixture thereof.

Bifunctional reactants to produce cellulose esters containing acetoacetate imide functionality are described in U.S. Pat. No. 6,369,214 which is incorporated by reference to the extent it does not contradict the statements herein. Cellulose esters containing acetoacetate imide functionality are the reaction product of a cellulose ester and at least one acetoacetyl group and an amine functional compound comprising at least one primary amine.

Bifunctional reactants to produce cellulose esters containing mercapto functionality are described in U.S. Pat. No. 5,082,914; which is incorporated by reference to the extent it does not contradict the statements herein. In one embodiment or in any of the mentioned embodiments, of the invention, the cellulose ester is grafted with a silicon-containing thiol component which is either commercially available or can be prepared by procedures known in the art. Examples of silicon-containing thiol compounds include, but are not limited to, (3-mercaptopropyl)trimethoxysilane, (3-mercaptopropyl)-dimethyl-methoxysilane, (3-mercaptopropyl)dimethoxymethylsilane, (3-mercaptopropyl)dimethylchlorosilane, (3-mercaptopropyl)dimethylethoxysilane, (3-mercaptopropyl)diethyoxy-methylsilane, and (3-mercapto-propyl)triethoxysilane.

Bifunctional reactants to produce cellulose esters containing melamine functionality are described in U.S. Pat. No. 5,182,379; which is incorporated by reference to the extent it does not contradict the statements herein. In one embodiment or in any of the mentioned embodiments, the cellulose esters containing melamine functionality are prepared by reacting a cellulose ester with a melamine compound to form a grafted cellulose ester having melamine moieties grafted to the backbone of the anhydrogluclose rings of the cellulose ester. In one embodiment or in any of the mentioned embodiments, the melamine compound is selected from the group consisting of methylol ethers of melamine and aminoplast resins.

Bifunctional reactants to produce cellulose esters containing long alkyl chain functionality are described in U.S. Pat. No. 5,750,677; which is incorporated by reference to the extent it does not contradict the statements herein. In one embodiment or in any of the mentioned embodiments, the cellulose esters containing long alkyl chain functionality is produced by reaction of cellulose in a carboxamide diluents or a urea-based diluent with an acylating reagent using a titanium-containing specifies. Cellulose esters containing long alkyl chain functionality can be selected from the group consisting of cellulose acetate hexanoate, cellulose acetate nonanoate, cellulose acetate laurate, cellulose palmitate, cellulose acetate stearate, cellulose nonanoate, cellulose hexanoate, cellulose hexanoate propionate, and cellulose nonanoate propionate.

In embodiments of the invention, the cellulose esters can be prepared by converting cellulose to cellulose esters with reactants that are obtained from a recycled CE content syngas source. In embodiments, such reactants can be cellulose reactants that include organic acids and/or acid anhydrides used in the esterification or acylation reactions of the cellulose, e.g., as discussed herein.

The cellulose esters, which include cellulose acetate, cellulose diacetate, cellulose triacetate, cellulose acetate propionate, and cellulose acetate butyrate, can be formulated with additives and fillers. Examples of additives include plasticizers, waxes, compatibilizers, biodegradation promoters, dyes, pigments, colorants, luster control agents, lubricants, anti-oxidants, viscosity modifiers, antifungal agents, anti-fogging agents, heat stabilizers, impact modifiers, flame retardants, corrosion inhibitors, antibacterial agents, softening agents, fragrances, and mold release agents.

The plasticizer reduces the melt temperature, the Tg, and/or the melt viscosity of the cellulose ester. Examples of plasticizers include phosphate plasticizers, benzoate plasticizers, adipate plasticizer, phthalate plasticizer, a glycolic acid ester, a citric acid ester plasticizer and a hydroxyl-functional plasticizer. More specifically, examples of plasticizers include triphenyl phosphate, tricresyl phosphate, cresyldiphenyl phosphate, octyldiphenyl phosphate, diphenylbiphenyl phosphate, trioctyl phosphate, tributyl phosphate, diethyl phthalate, dimethoxyethyl phthalate, dimethyl phthalate, dioctyl phthalate, dibutyl phthalate, di-2-ethylhexyl phthalate, butylbenzyl phthalate, dibenzyl phthalate, butyl phthalyl butyl glycolate, ethyl phthalyl ethyl glycolate, methyl phthalyl ethyl glycolate, triethyl citrate, tri-n-butyl citrate, acetyltriethyl citrate, acetyl-tri-n-butyl citrate, and acetyl-tri-n-(2-ethylhexyl) citrate, triacetin (glycerol triacetate), diethylene glycol diacetate, triethylene glycol diacetate, and tripropionin, diethylene glycol dibenzoate, rosin; hydrogenated rosin; stabilized rosin, and their monofunctional alcohol esters or polyol esters; a modified rosin including, but not limited to, maleic- and phenol-modified rosins and their esters; terpene resins; phenol-modified terpene resins; coumarin-indene resins; phenolic resins; alkylphenol-acetylene resins; and phenol-formaldehyde resins.

Some examples of plasticizers are those that are biodegradable. Examples of these plasticizers include triacetin, triethyl citrate, acetyl triethyl citrate, polyethylene glycol, the benzoate containing plasticizers such as the Benzoflex™ plasticizer series, poly (alkyl succinates) such as poly (butyl succinate), polyethersulfones, adipate based plasticizers, soybean oil expoxides such as the Paraplex™ plasticizer series, sucrose based plasticizers, dibutyl sebacate, tributyrin, sucrose acetate isobutyrate, the Resolflex™ series of plasticizers, triphenyl phosphate, glycolates, 2,2,4-trimethylpentane-1,3-diyl bis(2-methylpropanoate), and polycaprolactones.

The amount of plasticizer in the cellulose ester can range from about 0.5 to about 50 weight percent based on the weight of the cellulose ester. Other ranges can be from about 5 to about 35 weight percent based on the weight of the cellulose ester, from about 5 to about 30, and from about 10 to about 20.

Waxes have also been used to increase firmness. See, for example, U.S. Pat. No. 2,904,050, incorporated herein by reference.

The compatibilizer can be either a non-reactive compatibilizer or a reactive compatibilizer. The compatibilizer can enhance the ability of the cellulose ester to reach a desired small particle size to improve the dispersion of the cellulose ester into an elastomer. The compatibilizers used can also improve mechanical and physical properties of the elastomeric composition compositions by improving the interfacial interaction/bonding between the cellulose ester and the elastomer.

The amount of compatibilizer in the cellulose ester can range from about 1 wt % to about 40 wt %, from about 5 wt % to about 20 wt %, or about 10 to about 20 wt % based on the weight of the cellulose ester.

If desired, biodegradation and decomposition agents, e.g. hydrolysis assistant or any intentional degradation promoter additives can be added to or contained in the cellulose ester, added either during manufacture of the cellulose ester or subsequent to its manufacture and melt or solvent blended together. Those additives can promote hydrolysis by releasing acidic or basic residues, and/or accelerate photo (UV) or oxidative degradation and/or promote the growth of selective microbial colony to aid the disintegration and biodegradation in compost and soil medium. In addition to promoting the degradation, these additives can have an additional function such as improving the processability of the article or improving mechanical properties.

One set of examples of decomposition agents include inorganic carbonate, synthetic carbonate, nepheline syenite, talc, magnesium hydroxide, aluminum hydroxide, diatomaceous earth, natural or synthetic silica, calcined clay, and the like. If used, it is desirable that these fillers are dispersed well in the polymer matrix. The fillers can be used singly, or in a combination of two or more.

Another set of examples is aromatic ketones used as an oxidative decomposition agent, including benzophenone, anthraquinone, anthrone, acetylbenzophenone, 4-octylbenzophenone, and the like. These aromatic ketones may be used singly, or in a combination of two or more.

Other examples include transition metal compounds used as oxidative decomposition agents, such as salts of cobalt or magnesium, preferably aliphatic carboxylic acid (C12 to C20) salts of cobalt or magnesium, and more preferably cobalt stearate, cobalt oleate, magnesium stearate, and magnesium oleate; or anatase-form titanium dioxide, or titanium dioxide may be used. Mixed phase titanium dioxide particles may be used in which both rutile and anatase crystalline structures are present in the same particle. The particles of photoactive agent can have a relatively high surface area, for example from about 10 to about 300 sq. m/g, or from 20 to 200 sq. m/g, as measured by the BET surface area method. The photoactive agent can be added to the plasticizer if desired. These transition metal compounds can be used singly, or in a combination of two or more.

Examples of rare earth compounds used as an oxidative decomposition agents include rare earths belonging to periodic table Group 3A, and oxides thereof. Specific examples thereof include cerium (Ce), yttrium (Y), neodymium (Nd), rare earth oxides, hydroxides, rare earth sulfates, rare earth nitrates, rare earth acetates, rare earth chlorides, rare earth carboxylates, and the like. More specific examples thereof include cerium oxide, ceric sulfate, ceric ammonium Sulfate, ceric ammonium nitrate, cerium acetate, lanthanum nitrate, cerium chloride, cerium nitrate, cerium hydroxide, cerium octylate, lanthanum oxide, yttrium oxide, Scandium oxide, and the like. These rare earth compounds may be used singly, or in a combination of two or more.

Examples of basic additives used as an oxidative decomposition agents include alkaline earth metal oxides, alkaline earth metal hydroxides, alkaline earth metal carbonates, alkali metal carbonates, alkali metal bicarbonates, ZηO and basic Al2O3. At least one basic additive can be MgO, Mg(OH)2, MgCO3, CaO, Ca(OH)2, CaCO3, $NaHCO_3$, Na2CO3, K2CO3, ZηO KHCO3 or basic Al2O3. In one aspect, alkaline earth metal oxides, ZηO and basic A1203 can be used as a basic additive.

Examples of organic acid additives used as an oxidative decomposition agents include acetic acid, propionic acid, butyric acid, valeric acid, citric acid, tartaric acid, oxalic acid, malic acid, benzoic acid, formate, acetate, propionate, butyrate, valerate citrate, tartarate, oxalate, malate, maleic acid, maleate, phthalic acid, phthalate, benzoate, and combinations thereof.

Examples of other hydrophilic polymer or biodegradation promoter may include glycols, polyethers, and polyalcohols or other biodegradable polymers such as poly(glycolic acid), poly(lactic acid), polydioxanes, polyoxalates, poly(α-esters), polycarbonates, polyanhydrides, polyacetals, polycaprolactones, poly(orthoesters), polyamino acids, aliphatic polyesters such as poly(butylene)succinate, poly(ethylene) succinate, starch, regenerated cellulose, or aliphatic-aromatic polyesters such as PBAT.

Colorants can include carbon black, iron oxides such as red or blue iron oxides, titanium dioxide, silicon dioxide, cadmium red, calcium carbonate, kaolin clay, aluminum hydroxide, barium sulfate, zinc oxide, aluminum oxide; and organic pigments such as azo and disazo and triazo pigments, condensed azo, azo lakes, naphthol pigments, anthrapyrimidine, benzimidazolone, carbazole, diketopyrrolopyrrole, flavanthrone, indigoid pigments, isoindolinone, isoindoline, isoviolanthrone, metal complex pigments, oxazine, perylene, perinone, pyranthrone, pyrazoloquinazolone, quinophthalone, triarylcarbonium pigments, triphendioxazine, xanthene, thioindigo, indanthrone, isoindanthrone, anthanthrone, anthraquinone, isodibenzanthrone, triphendioxazine, quinacridone and phthalocyanine series, especially copper phthalocyanme and its nuclear halogenated derivatives, and also lakes of acid, basic and mordant dyes, and isoindolinone pigments, as well as plant and vegetable dyes, and any other available colorant or dye.

Luster control agents for adjusting the glossiness and fillers include silica, talc, clay, barium sulfate, barium carbonate, calcium sulfate, calcium carbonate, magnesium carbonate, and the like.

Suitable flame retardants include silica, metal oxides, phosphates, catechol phosphates, resorcinol phosphates, borates, inorganic hydrates, and aromatic polyhalides.

Antifungal and/or antibacterial agents include polyene antifungals (e.g., natamycin, rimocidin, filipin, nystatin, amphotericin B, candicin, and hamycin), imidazole antifungals such as miconazole (available as MICATIN® from WellSpring Pharmaceutical Corporation), ketoconazole (commercially available as NIZORAL® from McNeil consumer Healthcare), clotrimazole (commercially available as LOTRAMIN® and LOTRAMIN AF® available from Merck and CANESTEN® available from Bayer), econazole, omoconazole, bifonazole, butoconazole, fenticonazole, isoconazole, oxiconazole, sertaconazole (commercially available as ERTACZO® from OrthoDematologics), sulconazole, and tioconazole; triazole antifungals such as fluconazole, itraconazole, isavuconazole, ravuconazole, posaconazole, voriconazole, terconazole, and albaconazole), thiazole antifungals (e.g., abafungin), allylamine antifungals (e.g., terbinafine (commercially available as LAMISIL® from Novartis Consumer Health, Inc.), naftifine (commercially available as NAFTIN® available from Merz Pharmaceuticals), and butenafine (commercially available as LOTRAMIN ULTRA® from Merck), echinocandin antifungals (e.g., anidulafungin, caspofungin, and micafungin), polygodial, benzoic acid, ciclopirox, tolnaftate (e.g., commercially available as TINACTIN® from MDS Consumer Care, Inc.), undecylenic acid, flucytosine, 5-fluorocytosine, griseofulvin, haloprogin, caprylic acid, and any combination thereof.

Viscosity modifiers in modifying the melt flow index or viscosity of the cellulose ester, and include polyethylene glycols and polypropylene glycols, and glycerin.

Fragrances can be added if desired. Examples of fragrances include spices, spice extracts, herb extracts, essential oils, smelling salts, volatile organic compounds, volatile small molecules, methyl formate, methyl acetate, methyl butyrate, ethyl acetate, ethyl butyrate, isoamyl acetate, pentyl butyrate, pentyl pentanoate, octyl acetate, myrcene, geraniol, nerol, citral, citronellal, citronellol, linalool, nerolidol, limonene, camphor, terpineol, alpha-ionone, thujone, benzaldehyde, eugenol, isoeugenol, cinnamaldehyde, ethyl maltol, vanilla, vannillin, cinnamyl alcohol, anisole, anethole, estragole, thymol, furaneol, methanol, rosemary, lavender, citrus, freesia, apricot blossoms, greens, peach, jasmine, rosewood, pine, thyme, oakmoss, musk, vetiver, myrrh, blackcurrant, bergamot, grapefruit, acacia, passiflora, sandalwood, tonka bean, mandarin, neroli, violet leaves, gardenia, red fruits, ylang-ylang, acacia farnesiana, mimosa, tonka bean, woods, ambergris, daffodil, hyacinth, narcissus, black currant bud, iris, raspberry, lily of the valley, sandalwood, vetiver, cedarwood, neroli, strawberry, carnation, oregano, honey, civet, heliotrope, caramel, coumarin, patchouli, dewberry, helonial, coriander, pimento berry, labdanum, cassie, aldehydes, orchid, amber, orris, tuberose, palmarosa, cinnamon, nutmeg, moss, styrax, pineapple, foxglove, tulip, wisteria, clematis, ambergris, gums, resins, civet, plum, castoreum, civet, myrrh, geranium, rose violet, jonquil, spicy carnation, galbanum, petitgrain, iris, honeysuckle, pepper, raspberry, benzoin, mango, coconut, hesperides, castoreum, osmanthus, mousse de chene, nectarine, mint, anise, cinnamon, orris, apricot, plumeria, marigold, rose otto, narcissus, tolu balsam, frankincense, amber, orange blossom, bourbon vetiver, opopanax, white musk, papaya, sugar candy, jackfruit, honeydew, lotus blossom, muguet, mulberry, absinthe, ginger, juniper berries, spicebush, peony, violet, lemon, lime, hibiscus, white rum, basil, lavender, balsamics, fo-ti-tieng, osmanthus, karo karunde, white orchid, calla lilies, white rose, rhubrum lily, tagetes, ambergris, ivy, grass, seringa, spearmint, clary sage, cottonwood, grapes, brimbelle, lotus, cyclamen, orchid, glycine, tiare flower, ginger lily, green osmanthus, passion flower, blue rose, bay rum, cassie, African tagetes, Anatolian rose, Auvergne narcissus, British broom, British broom chocolate, Bulgarian rose, Chinese patchouli, Chinese gardenia, Calabrian mandarin, Comoros Island tuberose, Ceylonese cardamom, Caribbean passion fruit, Damascena rose, Georgia peach, white Madonna lily, Egyptian jasmine, Egyptian marigold, Ethiopian civet, Farnesian cassie, Florentine iris, French jasmine, French jonquil, French hyacinth, Guinea oranges, Guyana wacapua, Grasse petitgrain, Grasse rose, Grasse tuberose, Haitian vetiver, Hawaiian pineapple, Israeli basil, Indian sandalwood, Indian Ocean vanilla, Italian bergamot, Italian iris, Jamaican pepper, May rose, Madagascar ylang-ylang, Madagascar vanilla, Moroccan jasmine, Moroccan rose, Moroccan oakmoss, Moroccan orange blossom, Mysore sandalwood, Oriental rose, Russian leather, Russian coriander, Sicilian mandarin, South African marigold, South American tonka bean, Singapore patchouli, Spanish orange blossom, Sicilian lime, Reunion Island vetiver, Turkish rose, Thai benzoin, Tunisian orange blossom, Yugoslavian oakmoss, Virginian cedarwood, Utah yarrow, West Indian rosewood, and the like, and any combination thereof.

The cellulose esters and/or cellulose ester compositions can be extrudable, moldable, castable, thermoformable, or can be 3D printed. By "recycled CE content syngas" is meant syngas obtained from a synthesis gas operation utilizing a feedstock that contains a solid fossil fuel source, at least some content of recycled CE and optionally other recycled plastics, as described in the various embodiments more fully herein below. In embodiments, the recycled CE content syngas can be made in accordance with any of the processes for producing syngas described herein; can comprise, or consist of, any of the syngas compositions or syngas composition streams described herein; or can be made from any of the feedstock slurry compositions described herein.

In embodiments, the feedstock (for the synthesis gas operation) can be in the form of a combination of one or more particulated fossil fuel sources and particulated recycled CE and optional other plastics. In one embodiment or in any of the mentioned embodiments, the solid fossil fuel source can include coal. In one embodiment or in any of the mentioned embodiments, the solid fossil fuel source is coal having an average particle size less than 2 mm and recycled CE and plastic having an average particle size less than 2 mm or less than 1 mm, e.g., particulated recycled cellulose diacetate and particulated polyethylene and/or PET. In one embodiment or in any of the mentioned embodiments, the feedstock is in the form of an aqueous slurry that comprises coal and recycled CE. In embodiments, the feedstock is fed to a gasifier along with an oxidizer gas, and the feedstock is converted to syngas, as described more fully herein.

In embodiments, the recycled CE content syngas is utilized to make at least one chemical intermediate in a reaction scheme to make a Recycle CE (CE intermediate). In embodiments, the recycled CE content syngas can be a component of feedstock (used to make at least one CE intermediate) that includes other sources of syngas, hydrogen, carbon monoxide, or combinations thereof. In one embodiment or in any of the mentioned embodiments, the only source of syngas used to make the CE intermediates is the recycled CE content syngas.

In embodiments, the CE intermediates made using the recycled CE content syngas can be chosen from methanol, acetic acid, methyl acetate, acetic anhydride and combinations thereof. In embodiments, the CE intermediates can be a at least one reactant or at least one product in one or more of the following reactions: (1) syngas conversion to methanol; (2) syngas conversion to acetic acid; (3) methanol conversion to acetic acid, e.g., carbonylation of methanol to produce acetic acid; (4) producing methyl acetate from methanol and acetic acid; and (5) conversion of methyl acetate to acetic anhydride, e.g., carbonylation of methyl acetate and methanol to acetic acid and acetic anhydride.

In embodiments, recycled CE content syngas is used to produce at least one cellulose reactant. In embodiments, the recycled CE content syngas is used to produce at least one Recycle CE.

In embodiments, the recycled CE content syngas is utilized to make acetic anhydride. In embodiments, syngas that comprises recycled CE content syngas is first converted to methanol and this methanol is then used in a reaction scheme to make acetic anhydride. "RCES acetic anhydride" refers to acetic anhydride that is derived from recycled CE content syngas. Derived from means that at least some of the feedstock source material (that is used in any reaction scheme to make a CE intermediate) has some content of recycled CE content syngas.

In embodiments, the RCES acetic anhydride is utilized as a CE intermediate reactant for the esterification of cellulose to prepare a Recycle CE, as discussed more fully above. In embodiments, the RCES acetic acid is utilized as a reactant to prepare cellulose acetate or cellulose diacetate.

In embodiments, the RCES acetic anhydride is utilized to make a biodegradable Recycle CE.

In one aspect, a Recycle CE composition is provided that comprises at least one cellulose ester having at least one substituent on an anhydroglucose unit (AGU) derived from recycled CE content syngas. In embodiments, the substituent is a combination of acetyl and propionyl functional groups. In embodiments, the substituent is a combination of acetyl and butyryl functional groups. In embodiments, the substituent is any combination of organic acid functional groups. In an embodiment, the at least one substituent is an acetyl functional group.

In embodiments, the Recycle CE is cellulose di-acetate (CDA). In an embodiment, the Recycle CE is cellulose tri-acetate (CTA).

In embodiments, the Recycle CE is prepared from a cellulose reactant that comprises acetic anhydride that is derived from recycled CE content syngas.

In embodiments, the recycled CE content syngas comprises gasification products from a gasification feedstock. In an embodiment, the gasification products are produced by a gasification process using a gasification feedstock that comprises recycled CE. In embodiments, the gasification feedstock comprises coal.

In embodiments, the gasification feedstock comprises a liquid slurry that comprises coal and recycled CE. In embodiments, the gasification process comprises gasifying said gasification feedstock in the presence of oxygen.

In one aspect, a Recycle CE composition is provided that comprises at least one cellulose ester having at least one substituent on an anhydroglucose unit (AGU) derived from one or more chemical intermediates, at least one of which is obtained at least in part from recycled CE content syngas.

In aspects, an Recycle CE is provided that comprises the cellulose ester compositions, as described herein. In embodiments, the Recycle CE is a textile fabric. In embodiments, the Recycle CE is biodegradable and/or compositable. In embodiments, a staple fiber is provided that comprises a cellulose ester composition that comprises cellulose acetate, as described herein.

In embodiments, the Recycle CE is biodegradable. In embodiments, the Recycle CE is biodegradable and contains content derived from a renewable source, e.g., cellulose from wood or cotton linter, and content derived from a recycled material source, e.g., recycled CE. Thus, in embodiments, a thermoplastic material is provided that is biodegradable and contains both renewable and recycled content, i.e., made from renewable and recycled sources.

In one aspect, the invention is directed to a fiber comprising at least one Recycle CE, as described herein. In embodiments, sheets, webs or fabrics are provided that comprise such fibers. In embodiments, the sheets, webs or fabrics can be woven or non-woven. In embodiments, the sheets, webs or fabrics can be wet laid or dry laid.

In another aspect, the invention is directed to a spun yarn that comprises at least one Recycle CE, as described herein. In embodiments, fibers comprising at least one Recycle CE can be prepared by spinning fibers. The fibers can be spun as a continuous fiber or can be cut to a desired length.

In embodiments, the invention can include fibers, filaments, yarns and nonwoven fabrics as described in WO2018/160588 A1, published on Sep. 7, 2018 (Applicant: Eastman Chemical Company), the contents of which is incorporated herein by reference, with the proviso that the fibers, filaments, yarns or nonwoven fabrics comprise at least one Recycle CE having recycled CE content, as described more fully herein.

In another aspect, the invention is directed to a textile fabric comprising fibers that comprise at least one Recycle CE, as described herein. In embodiments, the textile fabric can be prepared from spun yarns comprising at least one Recycle CE, as described herein.

It has been found that slivers can be successfully formed from CA staple fibers and further processed successfully to spun yarns to make textile fabric. CA staple fibers may be environmentally-friendly, exhibit thermoplastic behavior, have a soft feel similar to that of cotton, and can be processed using both new and existing processing equipment.

As used herein, textile fabrics are materials made from spun yarn and that are either woven, knitted, crocheted, knotted, embroidered, braided/plaited, laced, or carpet piling. Textile fabrics can include geotextile fabrics, carpet pilings, and fabrics (which includes cloth). The geotextile fabrics as used in the context of a textile fabric herein are those that are woven or knitted. Examples of suitable types of textile fabrics formable from the inventive staple fibers can include, but are not limited to, clothing (undergarments, socks, hats, shirts, pants, dresses, scarves, gloves, etc.), bags, baskets, upholstered furnishings, window shades, towels, table cloths, bed coverings, flat surface coverings, in art work, filters, flags, backpacks, tents, handkerchiefs, rags, balloons, kites, sails, parachutes, automotive upholstery, protective clothing such as against heat for firefighters and welders, protective clothing for bullet armor or stab protection, medical textile fabrics such as implants, and agrotextile fabrics for crop protection. A CA staple fiber means a cellulose acetate staple fiber, and a "staple fiber" refers to a fiber cut from a continuous filament or tow band of continuous filaments. A carded sliver, spun yarn, or textile fabric "obtained from" a described element includes any number and type of intervening steps or process operations.

Staple fibers as described herein may be formed from one or more Recycle CEs including, but not limited to, cellulose acetate, cellulose propionate, cellulose butyrate, cellulose acetate formate, cellulose acetate propionate, cellulose acetate butyrate, cellulose propionate butyrate, and mixtures thereof. Although described herein with reference to "cellulose acetate," it should be understood that one or more of the above cellulose acid esters or mixed esters may also be used to form the fibers, nonwovens, and Recycle CEs as described herein. Various types of cellulose esters are described, for example, in U.S. Pat. Nos. 1,698,049; 1,683,347; 1,880,808; 1,880,560; 1,984,147, 2,129,052; and 3,617,201, each of which is incorporated herein by reference to the extent not inconsistent with the present disclosure. In some cases, other types of treated or regenerated cellulose (e.g., viscose, rayon, or lyocell) may or may not be used in forming staple fibers as described herein.

When the staple fiber is formed from cellulose acetate, it may be formed from cellulose diacetate, cellulose triacetate, or mixtures thereof. The cellulose acetate (or other Recycle CE) useful in embodiments of the present invention can have a degree of substitution in the range of from 1.9 to 2.9. As used herein, the term "degree of substitution" or "DS" refers to the average number of acyl substituents per anhydroglucose ring of the cellulose polymer, wherein the maximum degree of substitution is 3.0, as described above. In some cases, the cellulose acetate used to form fibers as described herein may have an average degree of substitution of at least about 1.95, 2.0, 2.05, 2.1, 2.15, 2.2, 2.25, or 2.3 and/or not more than about 2.9, 2.85, 2.8, 2.75, 2.7, 2.65, 2.6, 2.55, 2.5, 2.45, 2.4, or 2.35, with greater than 90, 91, 92, 93, 94, 95, 96, 97, 98, or 99 percent of the cellulose acetate having a degree of substitution greater than 2.15, 2.2, or 2.25. In some cases, greater than 90 percent of the cellulose acetate can have a degree of substitution greater than 2.2, 2.25, 2.3, or 2.35. Typically, acetyl groups can make up at least about 1, 5, 10, 15, 20, 25, 30, 35, 40, 45, 50, 55, or 60 percent and/or not more than about 99, 95, 90, 85, 80, 75, or 70 percent of the total acyl substituents.

In embodiments, the cellulose acetate may have a weight-average molecular weight (Mw) of not more than 90,000, measured using gel permeation chromatography with N-methyl-2-pyrrolidone (NMP) as the solvent. In some cases, the cellulose acetate may have a molecular weight of at least about 10,000, at least about 20,000, 25,000, 30,000, 35,000, 40,000, or 45,000 and/or not more than about 100,000, 95,000, 90,000, 85,000, 80,000, 75,000, 70,000, 65,000, 60,000, or 50,000.

In an aspect, the invention is directed to a staple fiber formed from cellulose acetate, as described herein. In embodiments, the fiber is at least partially coated with at least one finish. In embodiments, the fiber has a denier per filament of less than about 3.0 and a crimp frequency of less than 22 crimps per inch (CPI). In embodiments, a plurality of the fibers exhibits a fiber-to-fiber staple pad coefficient of friction of not more than about 0.70.

In aspects of the invention, a carded sliver is provided comprising CA staple fibers that comprise cellulose acetate prepared according to the methods described herein. A carded sliver is a continuous bundle or strand of loose untwisted fibers that are aligned generally relatively parallel to each other. This alignment is conducted by subjecting the fibers to a carding process.

Optionally, the carded sliver can be combed, which may be a desirable operation on natural fibers for very fine yarns intended to make finer fabrics. In combining, fine tooth combs are applied to the sliver to further separate and remove fibers that are too short and further align the fibers parallel to each other.

The carded sliver can be the output of a carding machine that is not yet subjected to combing (if used) and drawing operations. In embodiments, the carded sliver desirably has a total denier of at least 10,000 or least 15,000, or at least 20,000, or at least 25,000, or at least 30,000, or at least 35,000, or at least 40,000, or at least 45,000, or at least 50,000. In general, the sliver total denier would not exceed 200,000, or not exceed 150,000, or not exceed 100,000, or not exceed 80,000, or not exceed 60,000, or not exceed 50,000. For most applications, the sliver will have a total denier of 20,000 to 80,000, or 25,000 to 60,000 or 30,000 to 60,000. If one desires to convert the sliver denier to grains, a conversion factor of 60 grain sliver=35,000 denier is used.

In embodiments, spun yarns are provided that are obtained from one or more carded slivers, where at least one of the carded slivers comprise CA staple fibers (as described herein). Slivers and spun yarns of the present invention may be formed according to any suitable process.

In embodiments, carded slivers, spun yarn, and textile fabrics can be blends of CA staple fibers with other fibers that are not CA staple fibers. The CA staple fibers may be present in a sliver or spun yarn or in an amount of at least 5, or at least 10, or at least 15, or at least 20, or at least 25, or at least 30, or at least 35, or at least 40, or at least 45 wt. % and up to 70 or up to 60, or up to 55, or up to 52, or up to 50, or up to 45, or up to 40, or up to 35, or up to 30, or up to 25, or up to 22, or up to 20 wt. %, based on the total weight of the blend. One or more of the other fibers may be present in an amount of at least about 5, or at least 10, or at least 15, or at least 20, or at least 25, or at least 30, or at least 35, or at least 40, or at least 45, or at least 50, or at least 55, or at least 60, or at least 65, or at least 70, or at least 75, or at least 80 weight percent. Compositions of specific blends can be determined according to AATCC TM20A-2014, No. 1. Examples of suitable ranges of the CA staple fibers in the sliver, spun yarn, or textile fabric include from 5 to 70, or 5 to 65, or 5 to 60, or 5 to 55, or 5 to 50, or 5 to 45, or 5 to 40 or 5 to 35, or 5 to 30, or 5 to 25, or 5 to 25, or 5 to 20, or 10 to 70, or 10 to 65, or 10 to 60, or 10 to 55, or 10 to 50, or 10 to 45, or 10 to 40 or 10 to 35, or 10 to 30, or 10 to 25, or 10 to 25, or 10 to 20, or 15 to 70, or 15 to 65, or 15 to 60, or 15 to 55, or 15 to 50, or 15 to 45, or 15 to 40 or 15 to 35, or 15 to 30, or 15 to 25, or 15 to 25, or 15 to 20, or 20 to 70, or 20 to 65, or 20 to 60, or 20 to 55, or 20 to 50, or 20 to 45, or 20 to 40 or 20 to 35, or 20 to 30, or 20 to 25 wt % based on the weight of all fibers in the sliver, spun yarn, or textile fabric.

Other types of fibers suitable for use in a blend with CA staple fibers can include natural and/or synthetic fibers including, but not limited to, cotton, rayon, viscose) or other types of regenerated cellulose such as Cupro, Tencel, Modal, and Lyocell cellulose, acetates such as polyvinylacetate, wool, glass, polyamides including nylon, polyesters such as polyethylene terephthalate (PET), polycyclohexylenedimethylene terephthalate (PCT) and other copolymers, olefinic polymers such as polypropylene and polyethylene, polycarbonates, poly sulfates, poly sulfones, polyethers, acrylics, acrylonitrile copolymers, polyvinylchloride (PVC), poly lactic acid, poly glycolic acid and combinations thereof.

In embodiments, the Recycle CE can be biodegradable, meaning that such fibers are expected to decompose under certain environmental conditions. The degree of degradation can be characterized by the weight loss of a sample over a given period of exposure to certain environmental conditions. In some cases, the Recycle CE can exhibit a weight loss of at least about 5, 10, 15, or 20 percent after burial in soil for 60 days and/or a weight loss of at least about 15, 20, 25, 30, or 35 percent after 15 days of exposure to a typical municipal composter. However, the rate of degradation may vary depending on the particular end use of the cellulose ester, as well as the composition of the remaining article, and the specific test. Exemplary test conditions are provided in U.S. Pat. Nos. 5,970,988 and 6,571,802.

In some embodiments, the Recycle CE may be biodegradable fibers and such fibers may be used to form fibrous articles such as textiles, nonwoven fabrics, filters, and yarns. It has been found that Recycle CE as described herein exhibit enhanced levels of environmental non-persistence, characterized by better-than-expected degradation under various environmental conditions. Recycle CE including fibers and fibrous articles described herein may meet or exceed passing standards set by international test methods and authorities for industrial compostability, home compostability, and/or soil biodegradability.

To be considered "compostable," a material must meet the following four criteria: (1) the material must be biodegradable; (2) the material must be disintegrable; (3) the material must not contain more than a maximum amount of heavy metals; and (4) the material must not be ecotoxic. As used herein, the term "biodegradable" generally refers to the tendency of a material to chemically decompose under certain environmental conditions.

Biodegradability is an intrinsic property of the material itself, and the material can exhibit different degrees of biodegradability, depending on the specific conditions to which it is exposed. The term "disintegrable" refers to the tendency of a material to physically decompose into smaller fragments when exposed to certain conditions. Disintegration depends both on the material itself, as well as the physical size and configuration of the article being tested. Ecotoxicity measures the impact of the material on plant life, and the heavy metal content of the material is determined according to the procedures laid out in the standard test method.

The Recycle CE can exhibit a biodegradation of at least 70 percent in a period of not more than 50 days, when tested under aerobic composting conditions at ambient temperature (28° C.±2° C.) according to ISO 14855-1 (2012). In some cases, the Recycle CE can exhibit a biodegradation of at least 70 percent in a period of not more than 49, 48, 47, 46, 45, 44, 43, 42, 41, 40, 39, 38, or 37 days when tested under these conditions, also called "home composting conditions." These conditions may not be aqueous or anaerobic. In some cases, the Recycle CE can exhibit a total biodegradation of at least about 71, 72, 73, 74, 75, 76, 77, 78, 79, 80, 81, 82, 83, 84, 85, 86, 87, or 88 percent, when tested under according to ISO 14855-1 (2012) for a period of 50 days under home composting conditions. This may represent a relative biodegradation of at least about 95, 97, 99, 100, 101, 102, or 103 percent, when compared to cellulose subjected to identical test conditions.

To be considered "biodegradable," under home composting conditions according to the French norm NF T 51-800 and the Australian standard AS 5810, a material must exhibit a biodegradation of at least 90 percent in total (e.g., as compared to the initial sample), or a biodegradation of at least 90 percent of the maximum degradation of a suitable reference material after a plateau has been reached for both the reference and test item. The maximum test duration for biodegradation under home compositing conditions is 1 year. The Recycle CE as described herein may exhibit a biodegradation of at least 90 percent within not more than 1 year, measured according 14855-1 (2012) under home composting conditions. In some cases, the Recycle CE may exhibit a biodegradation of at least about 91, 92, 93, 94, 95, 96, 97, 98, 99, or 99.5 percent within not more than 1 year, or Recycle CE may exhibit 100 percent biodegradation within not more than 1 year, measured according 14855-1 (2012) under home composting conditions.

Additionally, or in the alternative, the Recycle CE described herein may exhibit a biodegradation of at least 90 percent within not more than about 350, 325, 300, 275, 250, 225, 220, 210, 200, 190, 180, 170, 160, 150, 140, 130, 120, 110, 100, 90, 80, 70, 60, or 50 days, measured according 14855-1 (2012) under home composting conditions. In some cases, the Recycle CE can be at least about 97, 98, 99, or 99.5 percent biodegradable within not more than about 70, 65, 60, or 50 days of testing according to ISO 14855-1 (2012) under home composting conditions. As a result, the Recycle CE may be considered biodegradable according to, for example, French Standard NF T 51-800 and Australian Standard AS 5810 when tested under home composting conditions.

The Recycle CE can exhibit a biodegradation of at least 60 percent in a period of not more than 45 days, when tested under aerobic composting conditions at a temperature of 58° C. (±2° C.) according to ISO 14855-1 (2012). In some cases, the Recycle CE can exhibit a biodegradation of at least 60 percent in a period of not more than 44, 43, 42, 41, 40, 39, 38, 37, 36, 35, 34, 33, 32, 31, 30, 29, 28, or 27 days when tested under these conditions, also called "industrial composting conditions." These may not be aqueous or anaerobic conditions. In some cases, the Recycle CE can exhibit a total biodegradation of at least about 65, 70, 75, 80, 85, 87, 88, 89, 90, 91, 92, 93, 94, or 95 percent, when tested under according to ISO 14855-1 (2012) for a period of 45 days under industrial composting conditions. This may represent a relative biodegradation of at least about 95, 97, 99, 100, 102, 105, 107, 110, 112, 115, 117, or 119 percent, when compared to the same Recycle CE subjected to identical test conditions.

To be considered "biodegradable," under industrial composting conditions according to ASTM D6400 and ISO 17088, at least 90 percent of the organic carbon in the whole item (or for each constituent present in an amount of more than 1% by dry mass) must be converted to carbon dioxide by the end of the test period when compared to the control or in absolute. According to European standard ED 13432 (2000), a material must exhibit a biodegradation of at least 90 percent in total, or a biodegradation of at least 90 percent of the maximum degradation of a suitable reference material after a plateau has been reached for both the reference and test item. The maximum test duration for biodegradability under industrial compositing conditions is 180 days. The Recycle CE described herein may exhibit a biodegradation of at least 90 percent within not more than 180 days, measured according 14855-1 (2012) under industrial composting conditions. In some cases, the Recycle CE may exhibit a biodegradation of at least about 91, 92, 93, 94, 95, 96, 97, 98, 99, or 99.5 percent within not more than 180 days, or Recycle CE may exhibit 100 percent biodegradation within not more than 180 days, measured according 14855-1 (2012) under industrial composting conditions.

Additionally, or in the alternative, Recycle CE described herein may exhibit a biodegradation of least 90 percent within not more than about 175, 170, 165, 160, 155, 150, 145, 140, 135, 130, 125, 120, 115, 110, 105, 100, 95, 90, 85, 80, 75, 70, 65, 60, 55, 50, or 45 days, measured according 14855-1 (2012) under industrial composting conditions. In some cases, the Recycle CE can be at least about 97, 98, 99, or 99.5 percent biodegradable within not more than about 65, 60, 55, 50, or 45 days of testing according to ISO 14855-1 (2012) under industrial composting conditions. As a result, the Recycle CE described herein may be considered biodegradable according ASTM D6400 and ISO 17088 when tested under industrial composting conditions.

The Recycle CE may exhibit a biodegradation in soil of at least 60 percent within not more than 130 days, measured according to ISO 17556 (2012) under aerobic conditions at ambient temperature. In some cases, Recycle CE can exhibit a biodegradation of at least 60 percent in a period of not more than 130, 120, 110, 100, 90, 80, or 75 days when tested under these conditions, also called "soil composting conditions." These may not be aqueous or anaerobic conditions. In some cases, the Recycle CE can exhibit a total biodegradation of at least about 65, 70, 72, 75, 77, 80, 82, or 85 percent, when tested under according to ISO 17556 (2012) for a period of 195 days under soil composting conditions. This may represent a relative biodegradation of at least about 70, 75, 80, 85, 90, or 95 percent, when compared to the same Recycle CE subjected to identical test conditions.

In order to be considered "biodegradable," under soil composting conditions according the OK biodegradable SOIL conformity mark of Vinçotte and the DIN Geprüft Biodegradable in soil certification scheme of DIN CERTCO, a material must exhibit a biodegradation of at least 90 percent in total (e.g., as compared to the initial sample), or a biodegradation of at least 90 percent of the maximum degradation of a suitable reference material after a plateau has been reached for both the reference and test item. The maximum test duration for biodegradability under soil compositing conditions is 2 years. The Recycle CE as described herein may exhibit a biodegradation of at least 90 percent within not more than 2 years, 1.75 years, 1 year, 9 months, or 6 months measured according ISO 17556 (2012) under soil composting conditions. In some cases, the Recycle CE may exhibit a biodegradation of at least about 91, 92, 93, 94, 95, 96, 97, 98, 99, or 99.5 percent within not more than 2 years, or Recycle CE may exhibit 100 percent biodegradation within not more than 2 years, measured according ISO 17556 (2012) under soil composting conditions.

Additionally, or in the alternative, Recycle CE described herein may exhibit a biodegradation of at least 90 percent within not more than about 700, 650, 600, 550, 500, 450, 400, 350, 300, 275, 250, 240, 230, 220, 210, 200, or 195 days, measured according 17556 (2012) under soil composting conditions. In some cases, the Recycle CE can be at least about 97, 98, 99, or 99.5 percent biodegradable within not more than about 225, 220, 215, 210, 205, 200, or 195 days of testing according to ISO 17556 (2012) under soil composting conditions. As a result, the Recycle CE described herein may meet the requirements to receive The OK biodegradable SOIL conformity mark of Vinçotte and to meet the standards of the DIN Geprüft Biodegradable in soil certification scheme of DIN CERTCO.

In some embodiments, Recycle CE may include less than 1, 0.75, 0.50, or 0.25 weight percent of components of unknown biodegradability. In some cases, the Recycle CE described herein may include no components of unknown biodegradability.

In addition to being biodegradable under industrial and/or home composting conditions, Recycle CE as described herein may also be compostable under home and/or industrial conditions. As described previously, a material is considered compostable if it meets or exceeds the requirements set forth in EN 13432 for biodegradability, ability to disintegrate, heavy metal content, and ecotoxicity. The Recycle CE described herein may exhibit sufficient compostability under home and/or industrial composting conditions to meet the requirements to receive the OK compost and OK compost HOME conformity marks from Vinçotte.

In some cases, the Recycle CE described herein may have a volatile solids concentration, heavy metals and fluorine content that fulfill all of the requirements laid out by EN 13432 (2000). Additionally, the Recycle CE may not cause a negative effect on compost quality (including chemical parameters and ecotoxicity tests).

In some cases, the Recycle CE can exhibit a disintegration of at least 90 percent within not more than 26 weeks, measured according to ISO 16929 (2013) under industrial composting conditions. In some cases, the Recycle CE may exhibit a disintegration of at least about 91, 92, 93, 94, 95, 96, 97, 98, 99, or 99.5 percent under industrial composting conditions within not more than 26 weeks, or Recycle CE may be 100 percent disintegrated under industrial composting conditions within not more than 26 weeks. Alternatively, or in addition, the Recycle CE may exhibit a disintegration of at least 90 percent under industrial compositing conditions within not more than about 26, 25, 24, 23, 22, 21, 20, 19, 18, 17, 16, 15, 14, 13, 12, 11, or 10 weeks, measured according to ISO 16929 (2013). In some cases, the Recycle CE described herein may be at least 97, 98, 99, or 99.5 percent disintegrated within not more than 12, 11, 10, 9, or 8 weeks under industrial composting conditions, measured according to ISO 16929 (2013).

In some cases, the Recycle CE can exhibit a disintegration of at least 90 percent within not more than 26 weeks, measured according to ISO 16929 (2013) under home composting conditions. In some cases, the Recycle CE may exhibit a disintegration of at least about 91, 92, 93, 94, 95, 96, 97, 98, 99, or 99.5 percent under home composting conditions within not more than 26 weeks, or the Recycle CE may be 100 percent disintegrated under home composting conditions within not more than 26 weeks. Alternatively, or in addition, the Recycle CE may exhibit a disintegration of at least 90 percent within not more than about 26, 25, 24, 23, 22, 21, 20, 19, 18, 17, 16, or 15 weeks under home composting conditions, measured according to ISO 16929 (2013). In some cases, the Recycle CE described herein may be at least 97, 98, 99, or 99.5 percent disintegrated within not more than 20, 19, 18, 17, 16, 15, 14, 13, or 12 weeks, measured under home composting conditions according to ISO 16929 (2013).

In embodiments, Recycle CE is provided that comprises recycled CE content and are biodegradable and/or compostable. It is believed that the Recycle CE can achieve higher levels of biodegradability and/or compostability without use of additives that have traditionally been used to facilitate environmental non-persistence of similar fibers. Such additives can include, for example, photodegradation agents, biodegradation agents, decomposition accelerating agents, and various types of other additives. Despite being substantially free of these types of additives, in embodiments, the Recycle CE can be provided that exhibit enhanced biodegradability and compostability when tested under industrial, home, and/or soil conditions, as discussed herein.

In some embodiments, the Recycle CE described herein may be substantially free of photodegradation agents. For example, the Recycle CE may include not more than about 1, 0.75, 0.50, 0.25, 0.10, 0.05, 0.025, 0.01, 0.005, 0.0025, or 0.001 weight percent of photodegradation agent, based on the total weight of the Recycle CE, or the Recycle CE may include no photodegradation agents. Examples of such photodegradation agents include, but are not limited to, pigments which act as photooxidation catalysts and are optionally augmented by the presence of one or more metal salts, oxidizable promoters, and combinations thereof. Pigments can include coated or uncoated anatase or rutile titanium dioxide, which may be present alone or in combination with one or more of the augmenting components such as, for example, various types of metals. Other examples of photodegradation agents include benzoins, benzoin alkyl ethers, benzophenone and its derivatives, acetophenone and its derivatives, quinones, thioxanthones, phthalocyanine and other photosensitizers, ethylene-carbon monoxide copolymer, aromatic ketone-metal salt sensitizers, and combinations thereof.

In some embodiments, the Recycle CE described herein may be substantially free of biodegradation agents and/or decomposition agents. For example, Recycle CE may include not more than about 1, 0.75, 0.50, 0.25, 0.10, 0.05, 0.025, 0.01, 0.005, 0.0025, 0.0020, 0.0015, 0.001, 0.0005 weight percent of biodegradation agents and/or decomposition agents, based on the total weight of the fiber, or Recycle CE may include no biodegradation and/or decomposition agents. Examples of such biodegradation and decomposition agents include, but are not limited to, salts of oxygen acid of phosphorus, esters of oxygen acid of phosphorus or salts thereof, carbonic acids or salts thereof, oxygen acids of phosphorus, oxygen acids of sulfur, oxygen acids of nitrogen, partial esters or hydrogen salts of these oxygen acids, carbonic acid and its hydrogen salt, sulfonic acids, and carboxylic acids.

Other examples of such biodegradation and decomposition agents include an organic acid selected from the group consisting of oxo acids having 2 to 6 carbon atoms per molecule, saturated dicarboxylic acids having 2 to 6 carbon atoms per molecule, and lower alkyl esters of the oxo acids or the saturated dicarboxylic acids with alcohols having from 1 to 4 carbon atoms. Biodegradation agents may also comprise enzymes such as, for example, a lipase, a cellulase, an esterase, and combinations thereof. Other types of biodegradation and decomposition agents can include cellulose phosphate, starch phosphate, calcium secondary phosphate, calcium tertiary phosphate, calcium phosphate hydroxide, glycolic acid, lactic acid, citric acid, tartaric acid, malic acid, oxalic acid, malonic acid, succinic acid, succinic anhydride, glutaric acid, acetic acid, and combinations thereof.

Recycle CE described herein may also be substantially free of several other types of additives that have been added to other fibers to encourage environmental non-persistence. Examples of these additives can include, but are not limited to, polyesters, including aliphatic and low molecular weight (e.g., less than 5000) polyesters, enzymes, microorganisms, water soluble polymers, modified cellulose acetate, water-dispersible additives, nitrogen-containing compounds, hydroxy-functional compounds, oxygen-containing heterocyclic compounds, sulfur-containing heterocyclic compounds, anhydrides, monoepoxides, and combinations thereof. In some cases, Recycle CE described herein may include not more than about 0.5, 0.4, 0.3, 0.25, 0.1, 0.075, 0.05, 0.025, 0.01, 0.0075, 0.005, 0.0025, or 0.001 weight percent of these types of additives, or the Recycle CE may not include any of these types of additives.

In another aspect, durable articles are provided that comprise the Recycle CEs, as described herein. In embodiments, the durable articles are made from moldable thermoplastic material comprising the Recycle CEs, as described herein. In embodiments, the moldable thermoplastic material comprises Recycle CEs chosen from cellulose acetate, cellulose diacetate, cellulose acetate propionate, cellulose acetate butyrate, or combinations thereof.

Examples of the articles that can be made with the Recycle CE include cups, trays, multi-compartment trays, candy sticks, balloon sticks, pots, plant pots, films, sheets, thermoformed trays and lids, straws, liquid carrying containers, solid or gel carrying containers, tool handles, ophthalmic articles such as eyeglass frames, optical films such as used in the displayers or televisions, computers, mobile phones, photographic film, coatings, buttons, and toys including toy construction/building articles, e.g., puzzle pieces, or other interlocking components such as building bricks.

In another aspect, an integrated process for preparing a Recycle CE is provide which comprises the processing steps of: (1) preparing a recycled CE content syngas in a synthesis gas operation utilizing a feedstock that contains a solid fossil fuel source, at least some content of recycled CE, and optional other recycled plastics; (2) preparing at least one chemical intermediate from said syngas; (3) reacting said chemical intermediate in a reaction scheme to prepare at least one cellulose reactant for preparing a Recycle CE, and/or selecting said chemical intermediate to be at least one cellulose reactant for preparing a Recycle CE; and (4) reacting said at least one cellulose reactant to prepare said Recycle CE; wherein said Recycle CE comprises at least one substituent on an anhydroglucose unit (AGU) derived from recycled CE content syngas.

In embodiments, the processing steps (1) to (4) are carried out in a system that is in fluid and/or gaseous communication (i.e., including the possibility of a combination of fluid and gaseous communication). It should be understood that the chemical intermediates, in one or more of the reaction schemes for producing Recycle CEs starting from recycled CE content syngas, may be temporarily stored in storage vessels and later reintroduced to the integrated process system.

In embodiments, the at least one chemical intermediate is chosen from methanol, methyl acetate, acetic anhydride, acetic acid, or combinations thereof. In embodiments, one chemical intermediate is methanol, and the methanol is used in a reaction scheme to make a second chemical intermediate that is acetic anhydride. In embodiments, the cellulose reactant is acetic anhydride.

In embodiments, Recycle CE can be obtained in a reaction scheme as described herein, or can be obtained by way of a recycle content allotment, provided that the allotment has its origin in, or withdrawn from an inventory of allotments containing at least one allotment having its origin in, gasifying a feedstock containing a solid fossil fuel and at least some content of CE. The "recycle content allotment" is a recycle content value that is transferred from an originating composition, compound or polymer at least a portion of which is obtained by or with the gasification of feedstock containing a solid fossil fuel and recycled CE, to a receiving composition, compound, or polymer (referred to herein as a "composition" for brevity) receiving the allotment, or deposited into a recycle inventory at least a portion of which originates from recycle waste. The recycle content value (whether by mass or percentage or any other unit of measure) can optionally be determined according to a standard system for tracking, allocating, and/or crediting recycle content among various compositions.

In one aspect, a process for obtaining a recycle cellulose ester (Recycle CE) is provided that comprises: (a) obtaining a recycle content allotment associated with gasifying a feedstock containing a solid fossil fuel and at least some content of recycled CE; and (b) associating at least a portion of the recycle content allotment with a cellulose ester to obtain a Recycle CE. In embodiments, the process includes gasifying a feedstock containing a solid fossil fuel and at least some content of recycled CE to produce a recycled CE content syngas, determining a recycle content value based on said gasifying, and generating the recycle content allotment based on said recycle content value. In embodiments, a cellulose ester composition is provided that comprises at least one Recycle CE obtained according to such processes, wherein the Recycle CE has an associated recycle content allotment. In embodiments, the recycle content allotment is chosen from a recycle content allocation, a recycle content credit, or a combination thereof.

A recycle content allotment can include an allocation or a credit obtained with the transfer or use of a raw material. In one embodiment or in combination with any of the mentioned embodiments, the composition receiving the recycle content allotment can be a non-recycle composition. As used herein, "non-recycle" means a composition, compound or polymer none of which was directly or indirectly derived from a recycled CE content syngas. As used herein, a "non-recycle feed" in the context of a feed to the gasifier means a feed that does not contain a recycle waste stream of any kind. Once a non-recycle feed, composition, compound, polymer, or article obtains a recycle content allotment (e.g. either through a credit or allocation), it becomes a recycle content feed, composition, compound, polymer or article, or in this case, a Recycle CE.

As used herein, the term "recycle content allocation" is a type of recycle content allotment, where the entity or person supplying the composition sells or transfers the composition to the receiving entity, and the entity that made the composition has an allotment at least a portion of which can be associated with the composition sold or transferred by the supplying entity to the receiving entity. The supplying entity or person can be controlled by the same entity or a variety of affiliates that are ultimately controlled or owned at least in part by a parent entity ("Family of Entities"), or they can be from a different Family of Entities. The term "recycle content credit" is a type of recycle content allotment, where the allotment is available for sale or transfer by other than the supplier of the composition that is transferred to the receiving entity or person.

The Recycle CE can have associated with it a recycle content allotment and may or may not contain a physical component that is traceable to a recycled CE content syngas. For example, the (i) manufacturer of the product can operate within a legal framework, or an association framework, or an industry recognized framework for making a claim to a recycle content through, for example, a system of credits transferred to the product manufacturer regardless of where or from whom the recycled CE content syngas, or downstream products made thereby, or reactant feedstocks to make the cellulose ester, is purchased or transferred, or (ii) a supplier of the recycled CE (optional other plastic) content syngas or downstream products made thereby ("supplier") operates within an allocation framework that allows for allocating a recycle content value to a portion or all of the recycled CE content syngas or downstream products made thereby and to transfer the allotment to the manufacturer of the product or any intermediary who obtains a supply of recycled CE content syngas or a downstream product thereof, from the supplier. In this system, one need not trace the source of a cellulose ester reactant back to the manufacture of recycled CE content syngas or back to any atoms contained in the recycled CE content syngas, but rather can use any cellulose ester reactant made by any process and have associated with such cellulose ester reactant, or have associated with the Recycle CE, a recycle content allotment. In an embodiment, the Recycle CE reactants do not contain recycle content.

In an embodiment, the Recycle CE has associated with it, or contains, or is labelled, advertised, or certified as containing recycle content in an amount of at least 0.01 wt. %, or at least 0.05 wt. %, or at least 0.1 wt. %, or at least 0.5 wt. %, or at least 0.75 wt. %, or at least 1 wt. %, or at least 1.25 wt. %, or at least 1.5 wt. %, or at least 1.75 wt. %, or at least 2 wt. %, or at least 2.25 wt. %, or at least 2.5 wt. %, or at least 2.75 wt. %, or at least 3 wt. %, or at least 3.5 wt. %, or at least 4 wt. %, or at least 4.5 wt. %, or at least 5 wt. %, or at least 6 wt. %, or at least 7 wt. %, or at least 10 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 65 wt. % and/or the amount can be up to 100 wt. %, or up to 95 wt. %, or up to 90 wt. %, or up to 80 wt. %, or up to 70 wt. %, or up to 60 wt. %, or up to 50 wt. %, or up to 40 wt. %, or up to 30 wt. %, or up to 25 wt. %, or up to 22 wt. %, or up to 20 wt. %, or up to 18 wt. %, or up to 16 wt. %, or up to 15 wt. %, or up to 14 wt. %, or up to 13 wt. %, or up to 11 wt. %, or up to 10 wt. %, or up to 8 wt. %, or up to 6 wt. %, or up to 5 wt. %, or up to 4 wt. %, or up to 3 wt. %, or up to 2 wt. %, or up to 1 wt. %, or up to 0.9 wt. %, or up to 0.8 wt. %, or up to 0.7 wt. %. The recycle content associated with the Recycle CE can be associated by applying an allotment (credit or allocation) to any cellulose ester made or sold. The allotment can be contained in an inventory of allotments created, maintained or operated by or for the Recycle CE manufacturer. The allotment can be obtained from any source along any manufacturing chain of products provided that its origin is in gasifying a feedstock containing a solid fossil fuel and a CE.

The amount of recycle content in a cellulose ester reactant, or the amount of recycle content applied to the Recycle CE, or the amount of recycle content cellulose ester reactant (r-reactant) needed to feed the reactor to claim a desired amount of recycle content in the Recycle CE in the event that all the recycle content from the r-reactant is applied to the Recycle CE, can be determined or calculated by any of the following methods:

(i) the amount of an allotment associated with the r-reactant used to feed the reactor is determined by the amount certified or declared by the supplier of the reactant transferred to the manufacturer of the Recycle CE, or (ii) the amount of allocation declared by the Recycle CE manufacturer as fed to the Recycle CE reactor, or (iii) using a mass balance approach to back-calculate the minimum amount of recycle content in the feedstock from an amount of recycle content declared, advertised, or accounted for by the manufacturer, whether or not accurate, as applied to the Recycle CE product, (iv) blending of non-recycle content with recycle content feedstock cellulose ester reactant or associating recycle content to a portion of the feedstock, using pro-rata mass approach In one embodiment, the Recycle CE manufacturer can make Recycle CE, or process a cellulose ester reactant and make a Recycle CE, or make Recycle CE by obtaining any source of a cellulose ester reactant composition from a supplier, whether or not such cellulose ester reactant composition has any recycle content, and either:

i. from the same supplier of the cellulose ester reactant composition, also obtain a recycle content allotment, or ii. from any person or entity, obtaining a recycle content allotment without a supply of a cellulose ester reactant composition from said person or entity transferring said recycle content allotment.

The allotment in (i) is obtained from a cellulose ester reactant supplier, and the cellulose ester reactant supplier also supplies cellulose ester reactant to the Recycle CE manufacturer or within its Family of Entities. The circumstance described in (i) allows a Recycle CE manufacturer to obtain a supply of a cellulose ester reactant composition that is a non-recycle content cellulose ester reactant, yet obtain a recycle content allotment from the cellulose ester reactant supplier. In one embodiment, the cellulose ester reactant supplier transfers a recycle content allotment to the Recycle CE manufacturer and a supply of cellulose ester reactant to the Recycle CE manufacturer, where the recycle content allotment is not associated with the cellulose ester reactant supplied, or even not associated with any cellulose ester reactant made by the cellulose ester reactant supplier. The recycle content allotment does not have to be tied to an amount of recycle content in a cellulose ester reactant composition or to any monomer used to make Recycle CE, but rather the recycle content allotment transferred by the cellulose ester reactant supplier can be associated with other products having their origin in recycled CE (and other plastic) content syngas other than those in a reaction scheme to make cellulose esters. For example, the cellulose ester reactant supplier can transfer to the Recycle CE manufacturer a recycle content associated with r-butyraldehyde and also supply a quantity of propionic anhydride even though r-butyraldehyde is not used directly or via downstream products in the synthesis of the cellulose ester such as a cellulose diacetate. This allows flexibility among the cellulose ester reactant supplier and Recycle CE manufacturer to apportion a recycle content among the variety of products they each make.

In one embodiment, the cellulose ester reactant supplier transfers a recycle content allotment to the Recycle CE manufacturer and a supply of cellulose ester reactant to the Recycle CE manufacturer, where the recycle content allotment is associated with cellulose ester reactant. In this case, the cellulose ester reactant transferred does not have to be a r-reactant, but can be any cellulose ester reactant so long as the allocation is associated with a manufacture of cellulose ester reactant. Optionally, the cellulose ester reactant being supplied can r-reactant and at least a portion of the recycle content allotment being transferred can be the recycle content in the r-reactant. The recycle content allotment transferred to the Recycle CE manufacturer can be up front with the cellulose ester reactant supplied in installments, or with each cellulose ester reactant installment, or apportioned as desired among the parties.

The allotment in (ii) is obtained by the Recycle CE manufacturer (or its Family of Entities) from any person or entity without obtaining a supply of cellulose ester reactant from the person or entity. The person or entity can be a cellulose ester reactant manufacturer that does not supply cellulose ester reactant to the Recycle CE manufacturer or its Family of Entities, or the person or entity can be a manufacturer that does not make cellulose ester reactant. In either case, the circumstances of (ii) allows a Recycle CE manufacturer to obtain a recycle content allotment without having to purchase any cellulose ester reactant from the entity supplying the recycle content allotment. For example, the person or entity may transfer a recycle content allotment through a buy/sell model or contract to the Recycle CE manufacturer or its Family of Entities without requiring purchase or sale of a allotment (e.g. as a product swap of products that are not cellulose ester reactant), or the person or entity may outright sell the allotment to the Recycle CE manufacturer or one among its Family of Entities. Alternatively, the person or entity may transfer a product, other than a cellulose ester reactant, along with its associated recycle content allotment to the Recycle CE manufacturer. This can be attractive to a Recycle CE manufacturer that has a diversified business making a variety of products other than Recycle CE requiring raw materials other than a cellulose ester reactant that the person or entity can supply to the Recycle CE manufacturer.

The allotment can be deposited into a recycle inventory (e.g. an inventory of allotments). In one embodiment, the allotment is an allocation created by the manufacturer of the recycled CE content syngas. The Recycle CE manufacturer can also make a cellulose ester, whether or not a recycle content is applied to the cellulose ester and whether or not recycle content, if applied to the cellulose ester, is drawn from the inventory. For example, the Recycle CE manufacturer may:

a. deposit the allotment into an inventory and merely store it; or b. deposit the allotment into an inventory and apply allotments from the inventory to products other than cellulose esters made by the Recycle CE manufacturer, or c. sell or transfer an allocation from the inventory into which at least one allotment, obtained as noted above, was deposited.

If desired, however, from that inventory, any recycle content allotment can be deducted in any amount and applied to a cellulose ester to make a Recycle CE. For example, a Recycle inventory of allotments can be generated having a variety of sources for creating the allotments. Some recycle content allotments (credits) can have their origin in solvolysis, e.g., methanolysis of recycle waste, or from gasification of other types of recycle waste, or from mechanical recycling of waste plastic or metal recycling, and/or from pyrolyzing recycle waste, or from any other chemical or mechanical recycling technology. The recycle inventory may or may not track the origin or basis of obtaining a recycle content value, or the inventory may not allow one to associate the origin or basis of an allocation to the allocation applied to Recycle CE. It is sufficient that an allocation is deducted from an allocation inventory and applied to Recycle CE regardless of the source or origin of the allocation, provided that a recycle content allotment derived from gasifying a solid fossil fuel and recycle CE is present in the allotment inventory as the time of withdrawal, or a recycle content allotment is obtained by the Recycle CE manufacturer as specified in step (i) or step (ii), whether or not that recycle content allotment is actually deposited into the inventory. In one embodiment, the recycle content allotment obtained in step (i) or (ii) is deposited into an inventory of allotments. In one embodiment, the recycle content allotment deducted from the inventory and applied to the Recycle CE originates from gasifying a feedstock containing solid fossil fuel and recycle CE.

As used throughout, the inventory of allotments can be owned by the Recycle CE manufacturer, operated by the Recycle CE manufacturer, owned or operated by other than the Recycle CE manufacturer but at least in part for the Recycle CE manufacturer, or licensed by the Recycle CE manufacturer. Also, as used throughout, the Recycle CE manufacturer may also include its Family of Entities. For example, while the Recycle CE manufacturer may not own or operate the inventory, one among its Family of Entities may own such a platform, or license it from an independent vendor, or operate it for the Recycle CE manufacturer. Alternatively, an independent entity may own and/or operate the inventory and for a service fee operate and/or manage at least a portion of the inventory for the Recycle CE manufacturer.

In one embodiment, the Recycle CE manufacturer obtains a supply of cellulose ester reactant from a supplier, and also obtains an allotment from the supplier, where such allotment is derived from gasifying a feedstock containing a solid fossil fuel and recycle CE, and optionally the allotment is associated with the cellulose ester reactant supplied by the supplier. In one embodiment, at least a portion of the allotment obtained by the Recycle CE manufacturer is either:

a. applied to Recycle CE made by the supply of cellulose ester reactant;

b. applied to Recycle CE not made by the supply of cellulose ester reactant, such as would be the case where Recycle CE is already made and stored in inventory or future made Recycle CE; or c. deposited into an inventory from which is deducted an allocation applied to Recycle CE (the Recycle CE applied allocation) and the deposited allocation either does, or does not, contribute to the amount of allocations from which the Recycle CE applied allocation is drawn.

d. deposited into an inventory and stored.

It is not necessary in all embodiments that r-reactant is used to make Recycle CE composition or that the Recycle CE was obtained from a recycle content allotment associated with a cellulose ester reactant composition. Further, it is not necessary that an allotment be applied to the feedstock for making the Recycle CE to which recycle content is applied. Rather, as noted above, the allotment, even if associated with a cellulose ester reactant composition when the cellulose ester reactant composition is obtained, can be deposited into an electronic inventory. In one embodiment, however, r-reactant is used to make the Recycle CE composition. In one embodiment, the Recycle CE is obtained from a recycle content allotment associated with a cellulose reactant composition (e.g. acetic acid, acetic anhydride, propionic acid, propionic anhydride, etc.). In one embodiment, at least a portion of r-reactant allotments are applied to Recycle CE to make a Recycle CE.

There can now also be provided a package or a combination of a Recycle CE and a recycle content identifier associated with Recycle CE, where the identifier is or contains a representation that the Recycle CE contains, or is sourced from, or associated with a recycle content. The package can be any suitable package for containing a cellulose ester, such as a plastic or metal drum, railroad car, isotainer, totes, polytotes, IBC totes, bottles, compressed bales, jerricans, and polybags. The identifier can be a certificate document, a product specification stating the recycle content, a label, a logo or certification mark from a certification agency representing that the article or package contains contents or the Recycle CE contains, or is made from sources or associated with recycle content, or it can be electronic statements (or a secure electronic certificate issued) by or for the Recycle CE manufacturer that accompany a purchase order or the product, or posted on a website as a statement, representation, or a logo representing that the Recycle CE contains or is made from sources that are associated with or contain recycle content, or it can be an advertisement transmitted electronically, by or in a website, by email, or by television, or through a tradeshow, in each case that is associated with Recycle CE. The identifier need not state or represent that the recycle content is derived from gasifying a feedstock containing a solid fossil fuel and recycle CE. Rather, the identifier can merely convey or communicate that the Recycle CE has or is sourced from a recycle content, regardless of the source.

In one embodiment, one may communicate recycle content information about the Recycle CE to a third party where such recycle content information is based on or derived from at least a portion of the allocation or credit. The third party may be a customer of the Recycle CE manufacturer or supplier, or may be any other person or entity, or governmental organization other than the entity owning the Recycle CE. The communication may electronic, by document, by advertisement, or any other means of communication.

In one embodiment, there is provided a system or package comprising:

a. Recycle CE or article made thereby, and b. an identifier such as a credit, label or certification associated with said Recycle CE or article made thereby, where the identifier is a representation that the cellulose ester or article made thereby has, or is sourced from, a recycle content.

The system can be a physical combination, such as package having at least Recycle CE as its contents and the package has a label, such as a logo, that the contents such as the Recycle CE has or is sourced from a recycle content. Alternatively, the label or certification can be issued to a third party or customer as part of a standard operating procedure of an entity whenever it transfers or sells Recycle CE having or sourced from recycle content. The identifier does not have to be physically on the Recycle CE or on a package and does not have to be on any physical document that accompanies or is associated with the Recycle CE. For example, the identifier can be an electronic credit transferred electronically by the Recycle CE manufacturer to a customer in connection with the sale or transfer of the Recycle CE product, and by sole virtue of being a credit, it is a representation that the Recycle CE has recycle content. The identifier itself need only convey or communicate that the Recycle CE has or is sourced from a recycle content, regardless of the source. In one embodiment, articles made from the Recycle CE may have the identifier, such as a stamp or logo embedded or adhered to the article. In one embodiment, the identifier is an electronic recycle content credit from any source. In one embodiment, the identifier is an electronic recycle content credit having its origin in gasifying a feedstock containing a solid fossil fuel and recycle CE.

The cellulose ester composition is made from any source of a cellulose ester reactant composition, whether or not the cellulose ester reactant composition is a r-reactant. Once a Recycle CE composition is made, it can be designated as having recycle content based on and derived from at least a portion of the allotment, again whether or not the r-reactant is used to make the Recycle CE composition. The allocation can be withdrawn or deducted from inventory. The amount of the deduction and/or applied to the Recycle CE can correspond to any of the methods described above, e.g. a mass balance approach.

In an embodiment, a recycle cellulose ester composition can be made by having an inventory of allocations, reacting a cellulose ester reactant composition in a synthetic process to make a Recycle CE, and applying a recycle content to that Recycle CE to thereby obtain a Recycle CE by deducting an amount of allocation from an inventory of allocations. A Recycle CE manufacturer may have an inventory of allocations by itself or one among its Family of Entities owning, possessing, or operating the inventory, or a third party operating at least a portion of the inventory for the Recycle CE manufacturer or its Family of Entities or as a service provided to the Recycle CE manufacturer or one among its Family of Entities. The amount of allocation deducted from inventory is flexible and will depend on the amount of recycle content applied to the Recycle CE. It should be at least sufficient to correspond with at least a portion if not the entire amount of recycle content applied to the Recycle CE. The method of calculation can be a mass balance approach or the methods of calculation described above. The inventory of allocations can be established on any basis and may be a mix of basis, provided that at least some amount of allocation in the inventory is attributable to gasifying a feedstock containing a solid fossil fuel and recycle CE. The recycle content allotment applied to the Recycle CE does not have to have its origin in gasifying a feedstock containing a solid fossil fuel and recycle CE, and instead can have its origin in any other method of generating allocations from recycle waste, such as through methanolysis or gasification of recycle waste, provided that the inventory of allotments also contains an allotment or has an allotment deposit having its origin in gasifying a feedstock containing a solid fossil fuel and recycle CE. In one embodiment, however, the recycle content applied to the Recycle CE is an allotment obtained from gasifying a feedstock containing a solid fossil fuel and recycle CE.

The following are examples of designating or declaring a recycle content to Recycle CE or a recycle content to a cellulose ester reactant composition:

1. A Recycle CE manufacturer applies at least a portion of an allotment to a cellulose ester composition where the allotment is associated with a recycle CE content syngas, and the cellulose ester reactant composition used to make the Recycle CE did not contain any recycle content or it did contain recycle content; or
2. A Recycle CE manufacturer applies at least a portion of an allotment to a cellulose ester composition where the allotment is derived directly or indirectly with a recycle content cellulose ester reactant, whether or not such cellulose ester reactant volume is used to make the Recycle CE; or
3. A Recycle CE manufacturer applies at least a portion of an allotment to a Recycle CE composition where the allotment is derived directly or indirectly with a recycle content cellulose ester reactant, and the recycle content cellulose ester reactant is used as a feedstock to make the Recycle CE to which the allotment is applied, and:
    a. all of the recycle content in the r-cellulose ester reactant is applied to determine the amount of recycle content in the Recycle CE, or
    b. only a portion of the recycle content in the r-cellulose ester reactant is applied to determine the amount of recycle content applied to the Recycle CE, the remainder stored in inventory for use to future Recycle CE, or for application to other existing Recycle CE made from r-cellulose ester reactant not containing any recycle content, or to increase the recycle content on an existing Recycle CE, or a combination thereof, or
    c. none of the recycle content in the r-cellulose ester reactant is applied to the Recycle CE and instead is stored in an inventory, and a recycle content from any source or origin is deducted from the inventory and applied to Recycle CE; or
4. A Recycle CE manufacturer applies at least a portion of an allotment to a cellulose ester reactant composition used to make a Recycle CE to thereby obtain a Recycle CE, where the allotment was obtained with the transfer or purchase of the same cellulose ester reactant composition used to make the Recycle CE and the allotment is associated with the recycle content in a cellulose ester reactant composition; or
5. A Recycle CE manufacturer applies at least a portion of an allotment to a cellulose ester reactant composition used to make a Recycle CE to thereby obtain a Recycle CE, where the allotment was obtained with the transfer or purchase of the same cellulose ester reactant composition used to make the Recycle CE and the allotment is not associated with the recycle content in a cellulose ester reactant composition but rather on the recycle content of a reactant or intermediate used to make the cellulose ester reactant composition; or
6. A Recycle CE manufacturer applies at least a portion of an allotment to a cellulose ester reactant composition used to make a Recycle CE to thereby obtain a Recycle CE, where the allotment was not obtained with the transfer or purchase of the cellulose ester reactant composition and the allotment is associated with the recycle content in the cellulose ester reactant composition; or 7. A Recycle CE manufacturer applies at least a portion of an allotment to a cellulose ester reactant composition used to make a Recycle CE to thereby obtain a Recycle CE, where the allotment was not obtained with the transfer or purchase of the cellulose ester reactant composition and the allotment is not associated with the recycle content in the cellulose ester reactant composition but rather with the recycle content of any reactant or intermediate used to make the cellulose ester reactant composition, such as an allotment associated with recycle content in propylene or ethylene; or
8. A Recycle CE manufacturer obtains an allotment having it origin in gasifying a feedstock containing a solid fossil fuel and recycle CE, and:
   a. no portion of the allotment is applied to a cellulose ester reactant composition to make Recycle CE and at least a portion is applied to Recycle CE to make a Recycle CE; or
   b. less than the entire portion is applied to a cellulose ester reactant composition used to make Recycle CE and the remainder is stored in inventory or is applied to future made Recycle CE or is applied to existing Recycle CE in inventory.

In one embodiment, the Recycle CE, or articles made thereby, can be offered for sale or sold as Recycle CE containing or obtained with recycle content. The sale or offer for sale can be accompanied with a certification or representation of the recycle content claim made in association with the Recycle CE or article made with the Recycle CE.

The obtaining of an allocation and designating (whether internally such as through a bookkeeping or an inventory tracking software program or externally by way of declaration, certification, advertising, representing, etc.) can be by the Recycle CE manufacturer or within the Recycle CE manufacturer Family of Entities. The designation of at least a portion of the Recycle CE as corresponding to at least a portion of the allotment (e.g. allocation or credit) can occur through a variety of means and according to the system employed by the Recycle CE manufacturer, which can vary from manufacturer to manufacturer. For example, the designation can occur internally merely through a log entry in the books or files of the Recycle CE manufacturer or other inventory software program, or through an advertisement or statement on a specification, on a package, on the product, by way of a logo associated with the product, by way of a certification declaration sheet associated with a product sold, or through formulas that compute the amount deducted from inventory relative to the amount of recycle content applied to a product.

Optionally, the Recycle CE can be sold. In one embodiment, there is provided a method of offering to sell or selling cellulose esters by:

a. A Recycle CE manufacturer or its Family of Entities obtaining a recycle content allocation, and the allocation can be obtained by any of the means described herein and can be deposited into inventory, the recycle content allocation having its origin in gasification of a feedstock containing a solid fossil fuel and a recycle CE,
b. converting a cellulose ester reactant composition in a synthetic process to make a cellulose ester composition, and the cellulose ester reactant composition can be any cellulose ester reactant composition or a r-cellulose ester reactant composition,
c. designating (e.g. assigning or associating) a recycle content to at least a portion of the cellulose ester composition from an inventory of allocations, where the inventory contains at least one entry that is an allocation having its origin in gasification of a feedstock containing a solid fossil fuel and a recycle CE. The designation can be the amount of allocation deducted from inventory, or the amount of recycle content declared or determined by the Recycle CE manufacturer in its accounts. Thus, the amount of recycle content does not necessarily have to be applied to the Recycle CE product in a physical fashion. The designation can be an internal designation to or by the Recycle CE manufacturer or its Family of Entities or a service provider in contractual relationship to the Recycle CE manufacturer or its Family of Entities, and
d. offering to sell or selling the cellulose ester composition as containing or obtained with recycle content corresponding at least in part with such designation. The amount of recycle content represented as contained in the Recycle CE sold or offered for sale has a relationship or linkage to the designation. The amount of recycle content can be a 1:1 relationship in the amount of recycle content declared on a Recycle CE offered for sale or sold and the amount of recycle content assigned or designated to the Recycle CE by the Recycle CE manufacturer.

The steps described need not be sequential and can be independent from each other. For example, the step a) of obtaining an allocation and the step of making Recycle CE from a cellulose ester reactant composition can be simultaneous and related if one employs a r-reactant composition to make the Recycle CE since the r-reactant is both a cellulose ester reactant composition and has a recycle content allocation associated with it.

As used throughout, the step of deducting an allocation from an inventory of allocations does not require its application to a Recycle CE product. The deduction also does not mean that the quantity disappears or is removed from the inventory logs. A deduction can be an adjustment of an entry, a withdrawal, an addition of an entry as a debit, or any other algorithm that adjusts inputs and outputs based on an amount recycle content associated with a product and one or a cumulative amount of allocations on deposit in the inventory. For example, a deduction can be a simple step of a reducing/debit entry from one column and an addition/credit to another column within the same program or books, or an algorithm that automates the deductions and entries/additions and/or applications or designations to a product slate. The step of applying an allocation to a Recycle CE product where such allocation was deducted from inventory also does not require the allocation to be applied physically to a Recycle CE product or to any document issued in association with the Recycle CE product sold. For example, a Recycle CE manufacturer may ship Recycle CE product to a customer and satisfy the "application" of the allocation to the Recycle CE product by electronically transferring a recycle content credit to the customer.

In one embodiment, the amount of recycle content in the r-reactant or in the Recycle CE will be based on the allocation or credit obtained by the manufacturer of the Recycle CE composition or the amount available in the Recycle CE manufacturer's inventory of allotments. A portion or all of the allocation or credit obtained by or in the possession of a manufacturer of Recycle CE can be designated and assigned to a r-reactant or Recycle CE on a mass balance basis. The assigned value of the recycle content to the r-reactant or Recycle CE should not exceed the total amount of all allocations and/or credits available to the manufacturer of the Recycle CE or other entity authorized to assign a recycle content value to the Recycle CE.

There is now also provided a method of introducing or establishing a recycle content in a cellulose ester without necessarily using an r-cellulose ester reactant feedstock. In this method, a. A syngas supplier makes a recycle CE content syngas and
b. a cellulose ester manufacturer:
    i. obtains an allotment derived from said recycle CE content syngas from the supplier or a third-party transferring said allotment,
    ii. makes a cellulose ester from a cellulose ester reactant, and
    iii. associates at least a portion of the allotment with at least a portion of the cellulose ester, whether or not the cellulose ester reactant used to make the cellulose ester contains a recycle content.

In this method, the cellulose ester manufacturer need not purchase r-cellulose ester reactant from any entity or from the supplier of cellulose ester reactant, and does not require the cellulose ester manufacturer to purchase a cellulose ester reactant from a particular source or supplier, and does not require the cellulose ester manufacturer to use or purchase a cellulose ester reactant composition having r-cellulose ester reactant in order to successfully establish a recycle content in the cellulose ester composition. The cellulose ester reactant manufacturer may use any source of cellulose ester reactant and apply at least a portion of the allocation or credit to at least a portion of the cellulose ester reactant feedstock or to at least a portion of the cellulose ester product. The association by the cellulose ester manufacturer may come in any form, whether by on in its inventory, internal accounting methods, or declarations or claims made to a third party or the public.

There is also provided a use for a cellulose ester reactant, the use including converting r-cellulose ester reactant in any synthetic process to make Recycle CE.

There is also provided a use for a cellulose ester reactant that includes converting a cellulose ester reactant in a synthetic process to make cellulose esters and applying at least a portion of an allotment to the cellulose ester to the cellulose ester reactant, where the allotment has its origin in gasifying a feedstock containing a solid fossil fuel and recycle CE or has its origin in an inventory of allotments where at least one deposit made into the inventory has its origin in gasifying a feedstock containing a solid fossil fuel and recycle CE.

In one embodiment, there is provided a cellulose ester composition that is obtained by any of the methods described above.

The cellulose ester reactant, such as a cellulose ester reactant can be stored in a storage vessel and transferred to a Recycle CE manufacturing facility by way of truck, pipe, or ship, or as further described below, the cellulose ester reactant production facility can be integrated with the Recycle CE facility. The cellulose ester reactant may be shipped or transferred to the operator or facility that makes the cellulose ester.

In an embodiment, the process for making Recycle CE can be an integrated process. One such example is a process to make Recycle CE by:

a. gasifying a feedstock containing a solid fossil fuel and recycle CE to make a recycled CE content syngas;
b. reacting said syngas or a non-recycle content syngas made in the gasifier in a reaction scheme to make a cellulose ester reactant composition;
c. reacting any cellulose ester reactant in a synthetic process to make a cellulose ester;
d. depositing an allotment into an inventory of allotments, said allotment originating from gasifying a feedstock containing a solid fossil fuel and recycle CE; and
e. applying any allotment from said inventory to the cellulose ester to thereby obtain a recycle content cellulose ester composition.

In one embodiment, one may integrate two or more facilities and make Recycle CE. The facilities to make Recycle CE, the cellulose ester reactant, or the syngas can be stand-alone facilities or facilities integrated to each other. For example, one may establish a system of producing and consuming a cellulose ester reactant composition, as follows:

a. provide a cellulose ester reactant manufacturing facility configured to produce a cellulose ester reactant composition;
b. provide a cellulose ester manufacturing facility having a reactor configured to accept a cellulose ester reactant composition from the cellulose ester reactant manufacturing facility; and
c. a supply system providing fluid communication between these two facilities and capable of supplying a cellulose ester reactant composition from the cellulose ester reactant manufacturing facility to the cellulose ester manufacturing facility, whether either the cellulose ester manufacturing facility makes Recycle CE or the cellulose ester reactant facility makes a recycle content cellulose ester reactant.

The Recycle CE manufacturing facility can make Recycle CE by accepting any cellulose ester reactant composition from the cellulose ester reactant manufacturing facility and applying a recycle content to Recycle CE made with the cellulose ester reactant composition by deducting allotments from its inventory and applying them to the Recycle CE, optionally in amounts using the methods described above. The allotments obtained and stored in inventory can be obtained by any of the methods described above and need not necessarily be allotments associated with r-cellulose ester reactant.

In one embodiment, there is also provided a system for producing Recycle CE as follows:

a. Provide a gasification manufacturing facility configured to produce an output composition comprising a recycled CE content syngas;
b. provide a cellulose ester reactant manufacturing facility configured to accept a recycled CE content syngas stream from the gasification manufacturing facility and making, through a reaction scheme one or more downstream products of said syngas to make an output composition comprising a cellulose ester reactant composition;
c. provide a cellulose ester (Recycle CE) manufacturing facility having a reactor configured to accept a cellulose ester reactant composition and making an output composition comprising a recycle content Recycle CE; and
d. a supply system providing fluid communication between at least two of these facilities and capable of supplying the output composition of one manufacturing facility to another one or more of said manufacturing facilities.

The Recycle CE manufacturing facility can make Recycle CE. In this system, the gasification manufacturing facility can have its output in fluid communication with the cellulose ester reactant manufacturing facility which in turn can have its output in fluid communication with the Recycle CE manufacturing facility. Alternatively, the manufacturing facilities of a) and b) alone can be in fluid communication, or only b) and c). In the latter case, the Recycle CE manufacturing facility can make Recycle CE directly by having the recycle CE content syngas produced in the gasification manufacturing facility converted all the way to Recycle CE, or indirectly by accepting any cellulose ester reactant composition from the cellulose ester reactant manufacturing facility and applying a recycle content to Recycle CE by deducting allotments from its inventory and applying them to the Recycle CE, optionally in amounts using the methods described above. The allotments obtained and stored in inventory can be obtained by any of the methods described above, The fluid communication can be gaseous or liquid or both. The fluid communication need not be continuous and can be interrupted by storage tanks, valves, or other purification or treatment facilities, so long as the fluid can be transported from the manufacturing facility to the subsequent facility through an interconnecting pipe network and without the use of truck, train, ship, or airplane. Further, the facilities may share the same site, or in other words, one site may contain two or more of the facilities. Additionally, the facilities may also share storage tank sites, or storage tanks for ancillary chemicals, or may also share utilities, steam or other heat sources, etc., yet also be considered as discrete facilities since their unit operations are separate. A facility will typically be bounded by a battery limit.

In one embodiment, the integrated process includes at least two facilities co-located within 5, or within 3, or within 2, or within 1 mile of each other (measured as a straight line). In one embodiment, at least two facilities are owned by the same Family of Entities.

In an embodiment, there is also provided an integrated r-olefin and Recycle CE generating and consumption system. This system includes:

a. Provide a gasification manufacturing facility configured to produce an output composition comprising a recycled CE content syngas;
b. provide a cellulose ester reactant manufacturing facility configured to accept a recycled CE content syngas stream from the gasification manufacturing facility and making, through a reaction scheme one or more downstream products of said syngas to make an output composition comprising a cellulose ester reactant composition;
c. provide a cellulose ester (Recycle CE) manufacturing facility having a reactor configured to accept a cellulose ester reactant composition and making an output composition comprising a recycle content Recycle CE; and
d. a piping system interconnecting at least two of said facilities, optionally with intermediate processing equipment or storage facilities, capable of taking off the output composition from one facility and accept said output at any one or more of the other facilities.

The system does not necessarily require a fluid communication between the two facilities, although fluid communication is desirable. In this system, ethylene or propylene made at the olefin manufacturing facility can be delivered to the cellulose ester reactant facility through the interconnecting piping network that can be interrupted by other processing equipment, such as treatment, purification, pumps, compression, or equipment adapted to combine streams, or storage facilities, all containing optional metering, valving, or interlock equipment. The equipment can be a fixed to the ground or fixed to structures that are fixed to the ground. The interconnecting piping does not need to connect to the cellulose ester reactant reactor or the cracker, but rather to a delivery and receiving point at the respective facilities. The same concept applies between the cellulose ester reactant facility and the Recycle CE facility. The interconnecting pipework need not connect all three facilities to each other, but rather the interconnecting pipework can be between facilities a)-b), or b)-c), or between a)-b)-c).

Closed Loop Process for Cellulose Esters

In aspects, the processes described herein can be or include a closed loop process. In embodiments, the closed loop process for providing a Recycle CE is provided where at least a portion of the recycled CE content syngas is used to make a cellulose ester material, and at least a portion of the feedstock to the gasifier is obtained from the same cellulose ester material type. In one embodiment, at least a portion of the recycled CE content syngas is used to make a cellulose ester material, for use in an article, through one or more intermediate products, at least one of which is made at least in part from the syngas, and at least a portion of the feedstock to the gasifier is obtained from the same article type.

A closed loop process does not require that all of the CE (and optional other plastics) in the feedstock be obtained from the same articles ultimately made from the resulting syngas, nor does it require that all of the resulting syngas is used to ultimately make the same articles as employed in the feedstock to the gasifier. Rather, as long as at least a portion of the recycle articles used as a feedstock and at least a portion of the syngas is used to make at least a portion of intermediate products that through several reaction steps make up at least a portion of the same polymer used to make the same type of article, the process qualifies as including a closed loop process.

A closed loop process is differentiated by the open loop process in that the renewed articles made in the open loop process are different from the end of life articles recycled as a feedstock material to the gasifier.

The match between recycled articles and renewed material made in a closed loop system does not have to be compositionally identical. Rather, the family of products and articles are a match.

The gasification process can be operated as a closed loop process and an open loop process simultaneously. For example, syngas made from feedstock obtained from end of life articles or products can be split, some used to make intermediate chemicals and polymers that ultimately will be used to make renewed polymers or articles that are the same as the polymers or articles contained in the end of life articles that are recycled as material in the feedstock to the gasifier, and some to make renewed articles and products that are different from the end of life articles and polymers used as material for a feedstock to the gasifier.

In one embodiment, there is provided a feedstock containing an article, optionally size reduced (r-article) and a recycle content CE syngas used to make a chemical that is used in a reaction scheme to make a renewed article, which can be a polymer or end use application, (n-article), wherein the r-article and n-article are the same. If the closed loop is with respect to CE polymers, the CE polymers are considered to be in the closed loop process even though they are not compositionally identical, provided that the CE polymers have the same kind of repeating units. For example, CAP's may have varying degrees of proponyl substitution and can be used in a variety of applications, but nevertheless are in a closed loop system since they each contain cellulose, acetate, and proponyl moieties.

Examples of r-article and n-article matches are:

i. r-cellulose acetate:n-cellulose acetate
ii. r-cellulose diacetate:n-cellulose diacetate
iii. r-cellulose triacetate:n-cellulose triacetate
iv. r-cellulose acetate propionate:n-cellulose acetate propionate
v. r-cellulose acetate butyrate:n-cellulose acetate butyrate
vi. r-tool handles:n-tool handles
vii. r-eyeglass frames:n-eyeglass frames
viii. r-fiber:n-fiber
ix. r-film:n-film
x. r-sheet:n-sheet In one embodiment, the closed loop process is one in which the recycle article used in the feedstock has the same application family as the renewed article. For example, a recycle cellulose diacetate as a feedstock is obtained from a textile that is also ultimately made into a renewed textile containing cellulose diacetate, or r-eyeglass frames to r-eyeglass frames.

In one embodiment, the closed loop process is one in which the recycle article used in the feedstock has the same end use application as the renewed article. For example, while a recycle cellulose diacetate as a feedstock is obtained from an upholstery textile that is also ultimately made into a renewed upholstery textile containing cellulose diacetate, or r-eyeglass frames to r-eyeglass frames.

In one embodiment, the feedstock contains cellulose diacetate and optionally other plastic obtained from eyeglass frames, and the recycle content syngas is used to make a chemical that is used in a reaction scheme to make cellulose diacetate, and optionally such cellulose diacetate is used to make eyeglass frames.

Closed Loop Recycling of CE Based Ophthalmic Articles

A common method of manufacturing eyeglass frames, particularly using cellulose acetate (which can be or include cellulose diacetate), involves first manufacturing a sheet of material, milling that sheet to a specified thickness, and then milling the desired frame and leg pieces from the sheet. As used herein, cellulose acetate can be or include cellulose diacetate. Because of the geometry of the frames, a large amount of scrap is generated during this manufacturing process. Since the cellulose acetate material for eyeglass frames is highly colored and patterned, and milling waste is sometimes contaminated by dirt, oils, and the like, options for closed loop recycling of the milling waste within the compounder-extruder-frame manufacturer value chain can be extremely limited. Therefore, there is excess scrap which the frame manufacturers must dispose of, which typically means placing it in a landfill.

As described herein, a closed loop solution to landfill disposal is provided by taking the cellulose acetate scrap, feeding it to a gasification process to make synthesis gas (by any of the processes described herein), which is then used in a reaction scheme to make a cellulose reactant, e.g., acetic anhydride, which is used in the production of cellulose acetate flake. In embodiments, cellulose acetate flake with recycled content (by mass balance allocation) is provided using cellulose acetate scrap as a source of recycled content.

In embodiments, a substantially completely (by mass balance allocation) sustainably sourced cellulose acetate flake for ophthalmic applications (such as eyeglass frames) using cellulose acetate scrap sourced from the ophthalmic industry is provided.

Cellulose acetate flake can be manufactured from wood or cotton pulp and acetic anhydride using methods known in the art. Cellulose acetate flake for ophthalmic applications can be approximately 60 wt % cellulose and 40 wt % acetyl. In such applications, cellulose acetate flake is typically compounded with a plasticizer, a thermal stabilizer, and colorants, and subsequently pelletized. In embodiments, bio-derived plasticizer such as triethyl citrate, triacetin, or others can be used to maximizing sustainably sourced content in the compounded material.

In embodiments, pellets of compounded cellulose acetate can used to make decorative sheets of cellulose acetate. The sheet can be extruded or formed by compression molding processes known as wet block or dry block. These processes use a combination of heat, pressure and time, with or without solvent, respectively. Pellets of different colors may be combined in these processes to produce mottled patterns in the decorative sheet. Defective sheets (pattern defects, incomplete fusion of pellets, gels, etc.) are a possible source of scrap. Also, purge scrap from the flake compounding process or from the sheet extrusion process are other possible sources of scrap.

The sheets of cellulose acetate are then polished to the desired thickness by a rotary tip cutter. Shavings of scrap material are produced at this step in the process and may be collected as a recycle CE source. The desired articles, namely eyeglass frames and temple leg pieces can be machined from the polished sheet. Substantial amounts of scrap are generated at this step in the process, both in the form of shavings from the cutting and milling processes, as well as chunks of material from locations such as where the lenses and the nose are located. Scrap in a mixed physical form and may be collected at this step of the process.

Eyeglass frames are assembled and held in inventory. From time to time, fashion trends can change and styles or color patterns of eyeglass frames may become out of fashion. Impaired finished goods inventory is another possible source of recycle material.

In embodiments, once the cellulose acetate scrap material is collected, it can be introduced to a granulator of reduce the size of the scrap to flake approximately 1 cm in diameter. The flaked scrap can then be introduced to a pulverization device to produce a powder with a particle size as discussed herein (with regard to the gasification processes), e.g., approximately 1 mm in diameter.

The powdered scrap material can then be introduced to a gasifier and consumed to produce synthesis gas, as described herein. The synthesis gas may then be used to manufacture a cellulose reactant, e.g., acetic anhydride, and then used to produce a renewed CE material, thus closing the loop and providing for (e.g., acetyl) content derived from recycled CE sources.

In embodiments, the recycle content associated with the closed loop process can be determined as discussed in any of the embodiments herein, e.g., using a mass balance allocation method of syngas credits derived from recycled or scrap CE material sources, where the amount of recycle content allocated to the acetyl component of the cellulose acetate flake may be up to 100%.

In embodiments, the scrap material may originate in many different physical forms, including but not limited to flake, pellets, shavings, sheets, purge chunks, individual parts of eyeglasses, assembled eyeglasses prior to sale, and returned eyeglasses from consumers. In embodiments, the scrap cellulose acetate material may contain plasticizers, including but not limited to diethyl phthalate, triethyl citrate, and triacetin. The scrap material may be of a single color, or multiple colors. Colorants may be also be present including pigments or organic dyes. The scrap material may be cellulose diacetate, commonly referred to as cellulose acetate, and optionally may include one or more materials selected from cellulose acetate propionate, cellulose acetate butyrate, polycarbonate, CR-39, transparent polyamide, acrylic, polyolefins such as HPDE, LDPE, and PP, polystyrene, SAN, ABS, polyesters such as PET, PETG, PCTG, PCT, PCTA, and Tritan.

In embodiments, the scrap CE containing material may be co-fed to the gasifier with coal in amounts up to 2, 5, 10 or 20 wt % scrap of the total gasifier feed. In other embodiments, the scrap material may constitute a higher percentage of the feed to a gasifier.

The concept of cellulose acetate flake with recycled content derived from cellulose acetate scrap may be extended from the example provided above concerning the ophthalmics industry to other uses of decorative cellulose acetate such as hair clips, to other uses of cellulose acetate such as tapes, textile fibers or nonwovens, and to other cellulose based plastic materials, such as cellulose acetate propionate or cellulose acetate butyrate or other mixed esters of cellulose (with or without plasticizer) for use in a wide variety of applications including but not limited to cosmetics packaging, electronics, barware, and various durable goods. In all cases, scrap cellulose based materials are recovered either in a post-industrial or post-consumer context, are prepared and fed to the gasifier to produce chemicals that are then consumed in the production of those same or other cellulose based materials (by a mass balance allocation method).

Accordingly, in embodiments, a process for preparing a recycle cellulose acetate composition (Recycle CA) is provided that comprises: (1) preparing a recycled CE content syngas in a synthesis gas operation by gasifying a feedstock containing a solid fossil fuel source and at least some content of cellulose acetate scrap; (2) determining a recycled content value of the feedstock; (3) providing a cellulose acetate composition and determining a recycled content value for the composition to provide a recycle cellulose acetate composition (Recycle CA), wherein at least a portion of the composition recycled content value is associated with the feedstock recycled content value, and wherein the cellulose acetate scrap comprises cellulose acetate and/or cellulose diacetate. In one embodiment, the cellulose acetate composition is provided by using the recycled CE content syngas as a feedstock in a reaction scheme to produce at least one cellulose reactant for preparing the Recycle CA and reacting the at least one cellulose reactant to prepare the Recycle CA. In an embodiment, the composition recycled content value is determined from the feedstock that comprises the cellulose acetate scrap. The cellulose acetate scrap can comprise post-industrial scrap (as discussed herein). In one embodiment, the cellulose acetate scrap comprises cellulose acetate scrap obtained from ophthalmic article manufacturing and the Recycle CA is used in an ophthalmic article manufacturing process. In embodiments, the composition recycled content value is obtained by mass balance allocation. In other embodiments, a similar process can be utilized for preparing a recycle mixed cellulose ester composition, for example a recycle cellulose acetate propionate (Recycle CAP) or a recycle cellulose acetate butyrate (Recycle CAB); or for preparing a recycle cellulose triacetate (Recycle CTA).

In embodiments, use of cellulose ester, e.g., CDA, ophthalmic article scrap (including scrap from processing and finished articles) as a feedstock source for producing recycled or renewed CE ophthalmic articles is provided. In embodiments, such use includes feeding such scrap to a gasifier to produce recycle CE content syngas.

In embodiments, use of recycle CE content syngas to make recycled or renewed cellulose esters is provided.

In embodiments, use of a recycle allocation credit based on recycle CE content syngas to provide a closed loop process recycle content in ophthalmic articles is provided.

Gasification Process

Unless otherwise stated, reference to the weight of the feedstock stream includes all solids, and if present liquids, fed to the gasifier, and unless otherwise stated, does not include the weight of any gases in the feedstock stream as fed to the injector or gasifier.

For purposes of classifying materials in the feedstock stream, a fossil fuel used is coal, petcoke, or any other solid at 25° C. and 1 atmosphere that is a byproduct from refining oil or petroleum. The fossil fuel portion of the feedstock stream is to be distinguished from CE and plastics, even if the CE and plastics are carbonaceous and derived from raw materials obtained from refining crude oil.

Generally, in a synthesis gas operation the feedstock stream comprised of finely particulated fossil fuel sources (e.g. coal, petcoke) and particulated CE and plastics, and optionally water and other chemical additives, are injected along with an oxidizer gas into gasification reaction zone or chamber of a synthesis gas generator (gasifier). A hot gas stream is produced in the reaction zone, desirably refractory lined, at high temperature and pressure generating a molten slag, ash, soot, and gases including hydrogen, carbon monoxide, carbon dioxide and can include other gases such as methane, hydrogen sulfide and nitrogen depending on the fuel source and reaction conditions. The hot gas stream is produced in the reaction zone is cooled using a syngas cooler or in a quench water bath at the base of the gasifier which also solidifies ash and slag and separates solids from the gases. The quench water bath also acts as a seal to maintain the internal temperature and pressure in the gasifier while the slag, soot and ash are removed into a lock hopper. The cooled product gas stream removed from the gasifier (the raw syngas stream) is further treated to remove remaining solids, and then further treated to remove acid gas (e.g. hydrogen sulfide) after optionally further cooling and shifting the ratio of carbon monoxide to hydrogen.

The optional plastics employed in the feedstock stream include any organic synthetic polymers that is solid at 25° C. at 1 atm. The polymers can be thermoplastic or thermosetting polymers. The polymer number average molecular weight can be at least 300, or at least 500, or at least 1000, or at least 5,000, or at least 10,000, or at least 20,000, or at least 30,000, or at least 50,000 or at least 70,000 or at least 90,000 or at least 100,000 or at least 130,000. The weight average molecular weight of the polymers can be at least 300, or at least 500, or at least 1000, or at least 5,000, or at least 10,000, or at least 20,000, or at least 30,000 or at least 50,000, or at least 70,000, or at least 90,000, or at least 100,000, or at least 130,000, or at least 150,000, or at least 300,000.

The CE and plastics can be post-consumer plastics and post-industrial plastics, also generally known as pre-consumer plastics. Post-consumer CE and plastics are those that have been used at least once for its intended application for any duration of time regardless of wear. Post-industrial or pre-consumer CE and plastics include rework, regrind, scrap, trim, out of specification materials that have not been used for their intended application, any CE materials that have been synthesized but not used in the finished application, or any CE and plastic that has not been used by the end consumer.

The form of the CE and plastics useful to be ground, and the pre-ground CE and plastics, are obtained from plastic forms that are not limited, and can include sheets, extruded shapes, moldings, films, laminates, pipes, foam, chips, flakes, particles, agglomerates, briquettes, powder, shredded pieces, long strips, or randomly shaped pieces having a wide variety of shapes, or any other form other than the original form of the article. The CE and plastics to be ground can be first roughly or coarsely size reduced prior to granulation or pulverization, by any means including chopping, shredding, harrowing, confrication, or cutting.

Desirably, textiles are not used as a source for obtaining the pre-ground CE and plastics since many textiles are mixed synthetic and natural fibers. The CE and plastics can be of varying age and composition. Non-combustible inorganic matter such as metals and minerals that prevent the CE and plastics from being incinerated and emitted may be contained in the CE and plastics for gasification. Examples include tin, cobalt, manganese, antimony, titanium, sodium, calcium, sulfur, zinc, and aluminum, their oxides and other compounds thereof. Advantageously, titanium and calcium that may be present in the CE and plastics can be slag modifiers.

In one embodiment or in any of the mentioned embodiments, the amount of calcium compounds present in the ash of pre-ground CE and plastics used in the feedstock is at least 30 wt. %, or at least 40 wt. %, or at least 50 wt. %, or at least 55 wt. %, or at least 60 wt. %, or at least 63 wt. %, based on the weight of the CE and plastic ash. The upper amount is desirably not more than 90 wt. %, or not more than 80 wt. %, or not more than 75 wt. %, based on the weight of the CE and plastic ash.

In another embodiment, the amount of sodium compounds present in the ash of pre-grounds CE and plastics used in the feedstock is at least 2 wt. %, or at least 3 wt. %, or at least 4 wt. %, or at least 5 wt. %, or at least 6 wt. %, or at least 7 wt. %, based on the weight of the CE and plastic ash. The upper amount is desirably not more than 20 wt. %, or not more than 17 wt. %, or not more than 15 wt. %, based on the weight of the CE and plastic ash.

In another embodiment, the amount of titanium compounds present in the ash of pre-ground CE and plastics used in the feedstock is at least 30 wt. %, or at least 40 wt. %, or at least 50 wt. %, or at least 60 wt. %, or at least 70 wt. %, or at least 75 wt. %, based on the weight of the CE and plastic ash. The upper amount is desirably not more than 96 wt. %, or not more than 90 wt. %, or not more than 86 wt. %, based on the weight of the CE and plastic ash.

In another embodiment, the amount of iron compounds present in the ash of pre-ground CE and plastics used in the feedstock is not more than 20 wt. %, or not more than 15 wt. %, or not more than 10 wt. %, or not more than 5 wt. %, or not more than 3 wt. %, or not more than 2 wt. %, or not more than 1.5 wt. %, based on the weight of the CE and plastic ash.

In another embodiment, the amount of aluminum compounds present in the ash of pre-ground CE and plastics used in the feedstock is not more than 20 wt. %, or not more than 15 wt. %, or not more than 10 wt. %, or not more than 5 wt. %, or not more than 3 wt. %, or not more than 2 wt. %, or not more than 1.5 wt. %, based on the weight of the CE and plastic ash.

In another embodiment, the amount of silicon compounds present in the ash of pre-ground CE and plastics used in the feedstock is not more than 20 wt. %, or not more than 15 wt. %, or not more than 10 wt. %, or not more than 8 wt. %, or not more than 6 wt. %, based on the weight of the CE and plastic ash.

Examples of CE and plastics (i.e. organic synthetic polymers that are solid at 25° C. at 1 atm) include acrylobutadienestyrene (ABS), cellulosics such as cellulose acetate, cellulose diacetate, cellulose triacetate, cellulose acetate propionate, cellulose acetate butyrate, and regenerated cellulose; epoxy, polyamides, phenolic resins, polyacetal, polycarbonates, polyesters including PET (polyethylene terephthalate) and copolyesters such as those containing residues of TMCD (2,2,4,4-tetramethyl-1,3-cyclobutanediol), CHDM (cyclohexanedimethanol), propylene glycol, or NPG (neopentylglycol) monomers; high density polyethylene, low density polyethylene, crosslinked polyethylene, polyphenylene-based alloys, polypropylene and copolymers thereof, other polyolefins, polystyrene, poly(methyl methacrylate), polytetrafluoroethylene, styrenic containing polymers, polyurethane, vinyl-based polymers, styrene acrylonitrile, thermoplastic elastomers other than tires which include thermoplastic elastomers, epoxy, and urea containing polymers and melamines.

In one embodiment or in any of the mentioned embodiments, the CE and plastics feedstock contains thermosetting polymers. Examples of the amounts of thermosetting polymers present in the CE and plastics feedstock can be at least 5 wt. %, or at least 10 wt. %, or at least 15 wt. %, or at least 20 wt. %, or at least 25 wt. %, or at least 30 wt. %, or at least 40 wt. %, or at least 50 wt. %, or at least 60 wt. %, or at least 70 wt. %, or at least 80 wt. %, or at least 90 wt. %, or at least 95 wt. %, or at least 97 wt. %, or at least 98 wt. %, or 100 wt. %, based on the weight of all CE and plastics in the feedstock or fed to the gasifier.

Examples of families of articles containing one or more of the above polymers that can be size reduced through granulation or pulverization or can be first densified followed by size reduction of the densified material, fed to the gasifier include packaging, engineering plastics, building and construction articles, household and houseware articles, furniture, lawn and garden, and automotive plastics. Examples of types of articles include bottles (for all types of applications such as beverage, food, detergents, cosmetics, personal care, etc.), bottle caps, cigarette filters and rods, eyeglass frames, cups, lids, trays, plumbing pipes (e.g. PBT, PVC, and PEX pipes), cable insulations, sheets, carrier bags, automotive moldings, bedding, seat cushions, seat covers, beverage machine fronts, fuel tanks, acrylic sheeting, buckets, audio tape, plumbing pipes, septic tanks, toys, cling film, agricultural film, milk carton coatings, electrical cable coating, heavy duty industrial bags, sound insulation, helmets, surf boards, stretch film, industrial packaging film, thin-walled containers, crates and boxes, and industrial wrapping and film, packaging made from flashspun high density polyethylene such as used for envelopes or medical packaging or house wrap, building insulation, diapers, sports equipment, eyeglass lenses, CD's and DVD's, food packaging, microwave-proof containers, garden furniture, medical packaging and appliances, luggage, and kitchen appliances.

Any of CE and plastics used to make the feedstock to the gasifier can be formulated with the additives and fillers described above that include plasticizers, waxes, compatibilizers, biodegradation promoters, dyes, pigments, colorants, luster control agents, lubricants, anti-oxidants, viscosity modifiers, antifungal agents, anti-fogging agents, heat stabilizers, impact modifiers, flame retardants, corrosion inhibitors, antibacterial agents, softening agents, fragrances, and mold release agents.

In one embodiment or in any of the mentioned embodiments, the feedstock contains CE and plastics at least a portion of which include or are obtained from cellulosics, such as cellulose derivates having an acyl degree of substitution of less than 3, or 1.8 to 2.8, such as cellulose acetate, cellulose diacetate, cellulose triacetate, cellulose acetate propionate, cellulose acetate butyrate.

In one embodiment or in any of the mentioned embodiments, the feedstock contains CE and plastics at least a portion of which include or are obtained from polymers having repeating terephthalate units, such as polyethylene terephthalate, polypropylene terephthalate, polybutylene terephthalate, and copolyesters thereof.

In one embodiment or in any of the mentioned embodiments, the feedstock contains CE and plastics at least a portion of which include or are obtained from copolyesters having multiple dicyclohexane dimethanol moeities, 2,2,4,4-tetramethyl-1,3-cyclobutanediol moieties, or combinations thereof.

In one embodiment or in any of the mentioned embodiments, the feedstock contains CE and plastics at least a portion of which include or are obtained from low density polyethylene, high density polyethylene, linear low-density polyethylene, polypropylene, polymethylpentene, polybutene-1, and copolymers thereof.

In one embodiment or in any of the mentioned embodiments, the feedstock contains CE and plastics at least a portion of which include or are obtained from high density polyethylene or fuel tanks.

In one embodiment or in any of the mentioned embodiments, the feedstock contains CE and plastics at least a portion of which include or are obtained from eyeglass frames. In one embodiment or in any of the mentioned embodiments, the feedstock contains plastics at least a portion of which include or are obtained from crosslinked polyethylene. An example of the feedstock is one which is obtained from or includes crosslinked polyethylene pipes or size reduced portions thereof. Crosslinked polyethylene is also commonly referred to as PEX. Its structure contains cross-linked bonds in the polymer to convert the thermoplastic polyethylene to a polymer which has more thermosetting characteristic. In one embodiment or in combination with any of the mentioned embodiments, or in combination with any of the mentioned embodiments, the cross-linked polyethylene is a thermoset polymer. The crosslinked polyethylene can be obtained by crosslinking any polyethylene (LDPE, LLDPE, HDPE), but typically is obtained by crosslinking low density polyethylene. The method of crosslinking is not limited, and can be accomplished during and after extrusion. The degree of crosslinking can be at least 50%. In one embodiment or in combination with any of the mentioned embodiments, or in combination with any of the mentioned embodiments, the degree of crosslinking satisfied ASTM F876. In one embodiment or in combination with any of the mentioned embodiments, or in combination with any of the mentioned embodiments, the degree of crosslinking is from 60 to 92%, or from 65 to 89%.

The cross-linking methods may be by irradiating a tube with an electron beam, the Engel crosslinking method by mixing a peroxide with the polyethylene and crosslinking occurring before extrusion as in the long die. Crosslinking the polyethylene can also be accomplished in a silane or vinylsilane based process or in an azo based process. The types of crosslinked polyethylene include PE-Xa (peroxide crosslinked with at least 75% crosslinking), PE-Xb (moisture cure or silane based with at least 65% crosslinking), PE-Xc (electron beam based with at least 60% crosslinking), and PE-Xd (azo based with at least 60% crosslinking).

In one embodiment or in any of the mentioned embodiments, the feedstock contains CE and plastics at least a portion of which include or are obtained from plastic bottles.

In one embodiment or in any of the mentioned embodiments, the feedstock contains CE and plastics at least a portion of which include or are obtained from diapers.

In one embodiment or in any of the mentioned embodiments, the feedstock contains CE and plastics at least a portion of which include or are obtained from Styrofoam.

In one embodiment or in any of the mentioned embodiments, the feedstock contains CE and plastics at least a portion of which include or are obtained from flashspun high density polyethylene.

Suitable CE and plastics (i.e. organic synthetic polymers that are solid at 25° C. at 1 atm.) include those having or classified within a resin ID code numbered 1-7 within the chasing arrow triangle established by the SPI. In one embodiment or in any of the mentioned embodiments, at least a portion of the feedstock to the gasifier, or at least a portion of the plastic recycle fed to the gasifier, contains one or more plastics that are not generally recycled. These would include plastics having numbers 3 (polyvinyl chloride), 5 (polypropylene), 6 (polystyrene), and 7 (other). In one embodiment or in combination with any of the mentioned embodiments, the recycle CE and plastics fed to the gasifier, or at least a portion of the feedstock, contains less than 10 wt %, or not more than 5 wt. %, or not more than 3 wt. %, or not more than 2 wt. %, or not more than 1 wt. %, or not more than 0.5 wt. %, or not more than 0.2 wt. %, or not more than 0.1 wt. %, or not more and 0.05 wt. % plastics having or corresponding to number 3 designation (polyvinyl chloride), or optionally plastics with a number 3 and 6 designation, or optionally with a number 3, 6 and 7 designation, based on the weight of all CE and plastics fed to the gasifier or gasification zone. In one embodiment or in combination with any of the mentioned embodiments, the recycle CE and plastics fed to the gasifier, or at least a portion of the feedstock, contains at least 1 wt %, or at least 2 wt. %, or at least 3 wt. %, or at least 5 wt. %, or at least 7 wt. %, or at least 10 wt. %, or at least 12 wt. %, or at least 15 wt. %, or at least 20 wt. %, or at least 25 wt. %, or at least 30 wt. %, or at least 40 wt. %, or at least or more than 50 wt. %, or at least 65 wt. %, or at least 85 wt. %, or at least 90 wt. % plastics having or corresponding to a number 5, or a number 6, or a number 7, or a combination thereof, based on the weight of the CE and plastics in the feedstock or fed to the gasifier or gasification zone. In one embodiment or in combination with any of the mentioned embodiments, the waste CE and plastic-containing feed can comprise at least 30, 35, 40, 45, 50, 55, 60, 65, 70, 75, 80, 85, 90, 95, or 99 weight percent of at least one, two, three, or four different kinds of resin ID codes. In one embodiment or in combination with any of the mentioned embodiments, the waste CE and plastic-containing feed contains less than 25, 20, 15, 10, 5, or 1 weight percent of polyvinyl chloride.

One of the advantages of gasifying CE and other plastics is that many plastics that would otherwise be landfilled because they cannot be re-melted (e.g. ground and melt extruded to renewed articles) can now be recycled and made into renewed products. An example of such a plastic is a thermoset plastic. In one embodiment or in combination with any of the mentioned embodiments, the feedstock contains plastics at least a portion of which cannot be melt extruded into a renewed product.

One of the advantages of gasifying CE and plastics is that many plastics that would otherwise be landfilled because they cannot or are not mechanically recycled due to the presence of an additive, coating, or dye/pigment can now be recycled and made into renewed products. For example, some CE and plastics which are heavily dyed, or contain additives that are suited for only a limited kind of application, or have coatings can all impair the functionality or appearance of renewed products. Other CE and plastics are typically not mechanically recycled through a process in which the plastic is melted because they are difficult to chop, granulate, or pulverize without first going through the step of densification, which adds costs. These plastics that are typically not mechanically recycled have a Resin ID code of 4, 5, 6, or 7, or combinations thereof.

In one embodiment or in combination with any of the mentioned embodiments, the feedstock contains CE and plastics at least a portion of which cannot or are not mechanically recycled, optionally within a 10 mile radius of the gasifier, or within a 50 mile, or within a 100 mile, or within a 150 mile, or within a 200 mile, or within a 250 mile, or within a 300 mile, or within a 400 mile, or within a 500 mile, or within a 600 mile, or within a 700 mile, or within a 800 mile, or within a 1000 mile, or within a 1250 mile, or within a 1500 mile, or within a 2000 mile radius of the gasifier, or within the same province, state, or country as the location of the gasifier.

In one embodiment or in combination with any of the mentioned embodiments, the feedstock contains CE and plastics at least a portion of which are obtained from polymers that are colored with a pigment or dye, optionally other than black.

In one embodiment or in combination with any of the mentioned embodiments, the feedstock contains CE and plastics at least a portion of which are obtained from articles having a layer of a label that is size reduced with the label.

In one embodiment or in combination with any of the mentioned embodiments, the feedstock contains CE and plastics at least a portion of which are obtained from articles that are not mechanically recycled due to the presence of an additive in article.

The source for obtaining post-consumer or post-industrial waste is not limited. A post-consumer CE and plastic source can include CE and plastic present in and/or separated from municipal solid waste streams ("MSW"). For example, an MSW stream can be processed and sorted to several discrete components, including textiles, fibers, mixed plastics, papers, wood, glass, metals, etc. Other sources of plastics include those obtained by collection agencies, or by or for or on behalf of plastics brand owners or consortiums or organizations, or from brokers, or from postindustrial sources such as scrap from mills or commercial production facilities, unsold fabrics from wholesalers or dealers, from mechanical and/or chemical sorting or separation facilities, from landfills, or stranded on docks or ships.

In one embodiment or in combination with any of the mentioned embodiments, at least a portion of the plastics in the feedstock, or the feedstock to the gasifier or gasification zone, contains or is obtained from cellulosic material. Examples of plastics that are cellulosics include cellulose acetate, cellulose diacetate, cellulose triacetate, cellulose acetate propionate, cellulose acetate butyrate, regenerated cellulose such a viscose, rayon, and Lyocel™ products. These cellulosics can be in any form, such as films, sheets, molded or stamped products, and contained in or on any article. Examples of articles containing cellulosics that can be contained in the feedstock or fed to the gasifier or gasification zone include ophthalmic products such as eyeglass frames, tool handles such as screwdriver handles, optical films such as used in the displayers or televisions, computers, mobile phones, photographic film, coatings, buttons, and toys including building bricks.

Desirably, the CE and plastics contain low levels or no halide containing polymers, in particular polyvinyl chloride, polyvinyl fluoride, polyvinylidene fluoride, and polytetrafluoroethane, and other fluorinated or chlorinated polymers. The release of chlorine or fluorine elements or radicals over time can impact the longevity of refractory lining on gasifiers operating at high temperature and pressure. In one embodiment or in any of the mentioned embodiments, the CE and other plastics contain less than 10 wt. %, or not more than 8 wt. %, or not more than 6 wt. %, or not more than 5 wt. %, or not more than 4 wt. %, or not more than 3.5 wt. %, or not more than 3 wt. %, or not more than 2.5 wt. %, or not more than 2 wt. %, or not more than 1.5 wt. %, or not more than 1 wt. %, or not more than 0.5 wt. %, or not more than 0.25 wt. %, or not more than 0.1 wt. %, or not more than 0.05 wt. %, or not more than 0.01 wt. % halide containing polymers, based on the weight of the CE and plastics. Desirably, the halide minimized or excluded is chlorine or fluorine.

The CE and plastics, as a co-fuel in a feedstock stream, have the advantage of not requiring thermal treatment prior to their introduction into the gasification zone or their introduction to one or more components of a feedstock stream. Unlike wood or grain which typically requires a thermal treatment beyond drying such as torrefaction, the pre-ground CE and plastics (those ground to the final size as combined into the feedstock stream) are not pyrolized or torrefied prior to their introduction into the gasifier, and desirably, the pre-ground CE and plastics are not obtained from a source of plastics which have been pyrolized or torrefied. In another embodiment, the pre-ground CE and plastics are not obtained from post-consumer plastics or post-industrial plastics which, after the consumer or industrial manufacture stage, are melted or extruded, and desirably the pre-ground CE and plastics are not melted or extruded prior to their entry into the gasifier. In another embodiment, the post-consumer or postindustrial CE and plastics, after shredding or any type of granulation, are not melted or extruded or receive a thermal treatment above their pyrolysis temperature, or above 150° C., or above 110° C., or above 100° C., or above 90° C., or above 80° C., or above 60° C., or above 58° C. or above their nominal temperature at their ambient conditions prior to their introduction into the gasification zone. It is to be noted that the pre-ground CE and plastics can be dried before their introduction into the feedstock stream, however, this would not be necessary in a slurry-based feedstock stream.

There is also provided a circular manufacturing process comprising:

i. providing a recycled CE, and
ii. size reducing said CE to make a pre-ground recycled CE, and
iii. gasifying said pre-ground CE to produce a recycled CE derived syngas, and
iv. either
   (i) reacting said recycled CE derived syngas to make a recycle content CE intermediate, polymer, or article (Recycle PIA) each of which have their origin at least in part to said recycled CE derived syngas or (ii) assigning a recycle content allotment, obtained from recycled CE or pre-ground CE, to a CE intermediate, polymer or article to produce a Recycle PIA; and v. optionally, taking back at least a portion of said Recycle PIA as a feedstock to said gasification process step (i), or (ii), or (iii).

In the above described process, an entirely circular or closed loop process is provided in which CE can be recycled multiple times to make the same family or classification of CE.

In this or in combination with any of the mentioned embodiments, the allotment can be assigned to an intermediate, polymer or article to produce a Recycle PIA directly from a recycle content value taken from the recycle CE or pre-ground CE or from the step of gasifying a feedstock containing a solid fossil fuel and recycle CE or pre-ground CE, or the allotment can be assigned to the intermediate, polymer or article to produce a recycle PIA indirectly by assigning the recycle content value taken from a recycle inventory into which recycle content value is deposited from the recycle content present in the recycled CE or in the pre-ground CE or the step of gasifying a feedstock containing a solid fossil fuel and recycle CE or pre-ground CE.

In one embodiment, the Recycle PIA is a CE of the same family or classification of CE as the recycled CE used in step (i).

In one embodiment, a Recycle PIA can be made by a process in which recycled CE are gasified according to any of the processes described herein.

There is also provided a circular manufacturing process comprising:

1. A manufacturer of syngas, or one among its Family of Entities, or an entity contracted with either of them (collectively the "Recipient"), receiving recycled CE (whether postindustrial or post-consumer), optionally and desirably from an industrial supplier of said CE or articles containing said CE, and
2. One or more of the Recipients size reducing said CE (optionally first densifying said CE, such as in the form of agglomerates or extrudates, followed by size reduction or coarse size reduction/densification/finer size reduction) to make a pre-ground recycled CE, and
3. One or more of the Recipients gasifying said pre-ground CE to produce a recycled CE derived syngas, and
4. either
   (i) reacting said recycled CE derived syngas to make a recycle content intermediate, polymer, or article (Recycle PIA) each of which have their origin at least in part to said recycled CE derived syngas or
   (ii) assigning a recycle content allotment, obtained from recycled CE or pre-ground CE, to an intermediate, polymer or article to thereby produce a Recycle PIA; and
5. optionally, furnishing at least a portion of said Recycle PIA to said industrial supplier, or to an entity contracted with said industrial supplier or with one among the Family of Entities of the industrial supplier for the supply of said Recycle PIA or an article made with said Recycle PIA.

In this or in combination with any of the mentioned embodiments, the allotment can be assigned to an intermediate, polymer or article to produce a Recycle PIA directly from a recycle content value taken from the recycled CE or pre-ground CE or from the step of gasifying a feedstock containing a solid fossil fuel and recycle CE or pre-ground CE, or the allotment can be assigned to the intermediate, polymer or article to produce a recycle PIA indirectly by assigning the recycle content value taken from a recycle inventory into which recycle content value is deposited from the recycle content present in the recycled CE or in the pre-ground CE or the step of gasifying a feedstock containing a solid fossil fuel and recycle CE or pre-ground CE.

In the above described process, an entirely circular or closed loop process is provided in which CE can be recycled multiple times to make the same family or classification of CE. The industrial supplier may furnish a processor entity with the CE or articles containing the CE to process those CE or articles into a form suitable or more suitable for gasification as further described herein to make pre-ground CE or precursors to pre-ground CE such as agglomerates, extrudates, chips, etc., and in turn, the processor entity supplies the pre-ground CE or precursors thereof to the manufacturer of syngas or one among its Family of Entities who can either feed to pre-ground CE as such to a feedstock stream to a gasifier, or can further process the precursors or pre-ground CE into a final size suitable for gasification by any suitable process, such as pulverization or grinding. The gasification processes, equipment, and designs used can be any of those mentioned herein. The syngas made using feedstocks containing the pre-ground CE can then either by converted through a reaction scheme to make Recycle PIA, or the allotments created by such gasification step can be stored in an inventory of allotments, and from the inventory of allotments from any source, a portion thereof can be withdrawn and assigned to an intermediate, polymer or article to make Recycle PIA. To close the circularity of the CE, at least a portion of the Recycle PIA can by furnished to the industrial supplier of the CE or articles, or it can be supplied to any entity contracted with the industrial supplier to process the Recycle PIA into a different form, different size, or to combine with other ingredients or CE (e.g. compounders and/or sheet extruders), or to make articles containing the PIA, for supply to or on behalf of the industrial supplier. The Recycle PIA furnished to the industrial supplier or one of its contracted entities is desirably in the same family or type of CE as the CE or article containing the CE was supplied by the industrial supplier to the Recipient.

The "recycle content allotment" is a recycle content value that is transferred from an originating composition, compound or polymer at least a portion of which is obtained by or with the gasification of feedstock a feedstock containing a solid fossil fuel and pre-ground CE, to a receiving composition, compound, or polymer (referred to herein as a "composition" for brevity) receiving the allotment, or deposited into a recycle inventory at least a portion of which originates from recycle waste.

The recycle content value (whether by mass or percentage or any other unit of measure) can optionally be determined according to a standard system for tracking, allocating, and/or crediting recycle content among various compositions. A "recycle content value" is a unit of measure representative of a quantity of material having its origin in recycled CE or pre-ground CE. The recycle content value can have its origin in any type of recycled CE or any recycled CE processed in any type of process before being gasified.

The particular recycle content value can be determined by a mass balance approach or a mass ratio or percentage or any other unit of measure and can be determined according to any system for tracking, allocating, and/or crediting recycle content among various compositions. A recycle content value can be deducted from a recycle inventory and applied to a product or composition to attribute recycle content to the product or composition. A recycle content value does not have to originate from gasifying recycled CE and can be a unit of measure having its known or unknown origin in any technology used to process recycled CE. In one embodiment, at least a portion of the recycle CE from which an allotment is obtained is also gasified as described throughout the one or more embodiments herein; e.g. combined with a fossil fuel and subjected to gasification.

In one embodiment, at least a portion of the recycle content allotment or allotment or recycle value deposited into a recycle content inventory is obtained from recycled CE or pre-ground CE. Desirably, at least 60%, or at least 70%, or at least 80%, or at least 90% or at least 95%, or up to 100% of the:

a. allotments or
b. deposits into the recycle inventory, or
c. recycle content value in the recycle inventory, or
d. recycle content value applied to compositions to make Recycle PIA are obtained from recycled CE or pre-ground CE.

A recycle content allotment can include an allocation or a credit obtained with the transfer or use of a raw material. In one embodiment or in combination with any of the mentioned embodiments, the composition receiving the recycle content allotment can be a non-recycle composition. As used herein, "non-recycle" means a composition, compound or polymer none of which was directly or indirectly derived from a recycle derived syngas stream. As used herein, a "non-recycle feed" in the context of a feed to the gasifier means a feed that does not contain a recycle waste stream of any kind. Once a non-recycle composition, compound, polymer, or article obtains a recycle content allotment (e.g. either through a credit or allocation), it becomes a recycle content composition, compound, polymer or article, or in this case, a Recycle PIA.

As used herein, the term "recycle content allocation" is a type of recycle content allotment, where the entity or person supplying the composition sells or transfers the composition to the receiving entity, and the entity that made the composition has an allotment at least a portion of which can be associated with the composition sold or transferred by the supplying entity to the receiving entity. The supplying entity or person can be controlled by the same entity or a variety of affiliates that are ultimately controlled or owned at least in part by a parent entity ("Family of Entities"), or they can be from a different Family of Entities. Generally, a recycle content allocation travels with a composition and with the downstream derivates of the composition. An allocation may be deposited into a recycle inventory and withdrawn from the recycle inventory as an allocation and applied to a composition to make a Recycle PIA.

The term "recycle content credit" is a type of recycle content allotment, where the allotment is available for sale or transfer by other than the supplier of the composition that is transferred to the receiving entity or person, or without the sale of a composition, or with the sale or transfer of a composition but the allotment is not associated the sale or transfer of the composition, or is deposited into or withdrawn from a recycle inventory that does not track the molecules of a recycle content feedstock to the molecules of the resulting compositions which were made with the recycle content feedstocks, or which does have such tracking capability but which did not track the particular allotment as applied to a composition.

In one embodiment or in combination with any of the mentioned embodiments, an allocation may be deposited into a recycle inventory, and a credit may be withdrawn from the inventory and applied to a composition to make a Recycle PIA. This would be the case where an allocation is created from a recycled CE and deposited into a recycle inventory, and deducting a recycle content value from the recycle inventory and applying it to a composition to make a Recycle PIA that either has no portion originating from syngas or does have a portion originating from syngas but such syngas making up the portion of the composition was not a recycle content syngas. In this system, one need not trace the source of a reactant compound or composition back to the manufacture of recycle derived syngas stream or back to any atoms contained in the recycle derived syngas stream, but rather can use any reactant compound or composition made by any process and have associated with such reactant compound or composition, or have associated with the Recycle PIA, a recycle content allotment. In an embodiment, the Recycle PIA reactants (the compositions used to make Recycle PIA or the compositions to which an allotment is applied) do not contain recycle content.

In one embodiment, the composition receiving an allotment to make a Recycle PIA originates in part from a syngas stream obtained by any gasification process. The feedstock to the gasification process may optionally contain solid fossil fuel such as coal. The feedstock may optionally also contain a combination of solid fossil fuel and recycle CE or pre-ground CE. In one embodiment, there is provided a process in which:

a. a recycled CE is obtained,
b. a recycle content value (or allotment) is obtained from the recycled CE and
    i. deposited into a recycle inventory, and an allotment (or credit) is withdrawn from the recycle inventory and applied to a composition to obtain a Recycle PIA, or
    ii. applied to a composition to obtain a Recycle PIA; and
c. at least a portion of the recycled CE is subjected to a gasification process, optionally by combining it with a solid fossil fuel as a feedstock to a gasifier, optionally according to any of the designs or processes described herein; and
d. optionally at least a portion of the composition in step b. originates from a syngas stream, optionally the syngas stream having been obtained by any of the feedstocks and methods described herein.

The steps b. and c. do not have to occur simultaneously. In one embodiment, they occur within a year of each other, or within six (6) months of each other, or within three (3) months of each other, or within one (1) month of each other, or within two (2) weeks of each other, or within one (1) week of each other, or within three (3) days of each other. The process allows for a time lapse between the time an entity or person receiving the recycled CE and creating the allotment (which can occur upon receipt or ownership of the recycled CE) and the actual processing of the recycled CE in a gasifier.

As used herein, "recycle inventory" and "inventory" mean a group or collection of allotments (allocations or credits) from which deposits and deductions of allotments in any units can be tracked. The inventory can be in any form (electronic or paper), using any or multiple software programs, or using a variety of modules or applications that together as a whole tracks the deposits and deductions. Desirably, the total amount of recycle content withdrawn (or applied to the Recycle PIA) does not exceed the total amount of recycle content allotments or credits on deposit in the recycle inventory (from any source, not only from gasification of recycle CE). However, if a deficit of recycle content value is realized, the recycle content inventory is rebalanced to achieve a zero or positive recycle content value available. The timing for rebalancing can be either determined and managed in accordance with the rules of a particular system of accreditation adopted by the recycle content syngas manufacturer or by one among its Family of Entities, or alternatively, is rebalanced within one (1) year, or within six (6) months, or within three (3) months, or within one (1) month of realizing the deficit. The timing for depositing an allotment into the recycle inventory, applying an allotment (or credit) to a composition to make a Recycle PIA, and gasifying a recycled CE, need not be simultaneous or in any particular order. In one embodiment, the step of gasifying a particular volume of recycle CE occurs after the recycle content value or allotment from that volume of recycled CE is deposited into a recycle inventory. Further, the allotments or recycle content values withdrawn from the recycle inventory need not be traceable to recycle CE or gasifying recycle CE, but rather can be obtained from any waste recycle stream, and from any method of processing the recycle waste stream. Desirably, at least a portion of the recycle content value in the recycle inventory is obtained from recycle CE, and optionally at least a portion of recycle CE are processed in the one or more gasification processes as described herein, optionally within a year of each other and optionally at least a portion of the volume of recycle CE from which a recycle content value is deposited into the recycle inventory is also processed by any or more of the gasification processes described herein.

The determination of whether a Recycle PIA is derived directly or indirectly from recycled waste is not on the basis of whether intermediate steps or entities do or do not exist in the supply chain, but rather whether at least a portion of the recycled CE molecules fed to the gasifier can be traced into a Recycle PIA. The Recycle PIA is considered to be directly derived from recycled CE or have direct contact with recycled CE if at least a portion of the molecules in the Recycle PIA can be traced back, optionally through one or more intermediate steps or entities, to at least a portion of the recycle content syngas molecules. Any number of intermediaries and intermediate derivates can be made before the Recycle PIA is made.

A Recycle PIA can be indirectly derived from recycled CE if no portion of its molecules are obtained from recycle content syngas molecules or some portion of is molecules are obtained from recycle content syngas molecules but the Recycle PIA has a recycle content value that exceeds the recycle content value associated with the recycle content syngas molecules, and in this latter case, a Recycle PIA can be both directly and indirectly derived from recycled CE.

In one embodiment or in combination with any of the mentioned embodiments, the Recycle PIA is indirectly derived from recycled CE or recycle content syngas. In another embodiment, the Recycle PIA is directly derived from recycled CE or recycle content syngas. In another embodiment, the Recycle PIA is indirectly derived from recycled CE or recycle content syngas and no portion of the Recycle PIA is directly derived from the recycled CE or recycle content syngas.

In another embodiment, there is provided a variety of methods for apportioning the recycle content among the various Recycle PIA compositions made by any one entity or a combinations of entities among the Family of Entities of which the recycle content syngas manufacturer is a part. For example, the recycle content syngas manufacturer, of any combination or the entirety of its Family of Entities, or a Site, can:

a. adopt a symmetric distribution of recycle content values among its product(s) based on the same fractional percentage of recycle content in one or more feedstocks or based on the amount of allotment received. For example, if 5 wt. % of the gasification feedstock is recycled CE, or if the recycle content value is 5 wt. % of the entire gasifier feedstock, then all Recycle PIA compositions may contain 5 wt. % recycle content value. In this case, the amount of recycle content in the products is proportional to the amount of recycle content in the feedstock to make the products; or b. adopt an asymmetric distribution of recycle content values among its product(s) based on the same fractional percentage of recycle content in the one or more feedstocks or based on the amount of allotment received. For example, if 5 wt. % of the gasifier feedstock is recycled CE, or if the allotment value is 5 wt. % of the entire gasifier feedstock, then one volume or batch of Recycle PIA can receive a greater amount of recycle content value that other batches or volume of Recycle PIA. One batch of PVA can contain 20% recycle content by mass, and another batch can contain zero 0% recycle content, even though both volumes may be compositionally the same, provided that the amount of recycle content value withdrawn from a recycle inventory and applied to the Recycle PIA does not exceed the amount of recycle content value deposited into the recycle inventory, or if a deficit is realized, the overdraft is rebalanced to zero or a positive credit available status as described above. In the asymmetric distribution of recycle content, a manufacturer can tailor the recycle content to volumes of Recycle PIA sold as needed among customers, thereby providing flexibility among customers some of whom may need more recycle content than others in a PVA volume.

Both the symmetric distribution and the asymmetric distribution of recycle content can be proportional on a Site wide basis, or on a multi-Site basis. In one embodiment or in combination with any of the mentioned embodiments, the recycle content input (recycle CE or allotments) can be within a Site and recycle content values from said inputs are applied to one or more compositions made at the same Site to make Recycle PIA. The recycle content values can be applied symmetrically or asymmetrically to one or more different compositions made at the Site.

In one embodiment or in combination with any of the mentioned embodiments, the recycle content input or creation (recycle content feedstock or allotments) can be to or at a first Site, and recycle content values from said inputs are transferred to a second Site and applied to one or more compositions made at a second Site, The recycle content values can be applied symmetrically or asymmetrically to the compositions at the second Site.

The Recycle PIA can have associated with it a recycle content allotment and may or may not contain a physical component that is traceable to a recycle derived syngas stream. For example, the (i) manufacturer of the product can operate within a legal framework, or an association framework, or an industry recognized framework for making a claim to a recycle content through, for example, a system of credits transferred to the product manufacturer regardless of where or from whom the recycle derived syngas stream, or downstream products made thereby, or reactant feedstocks to make the polymer and/or article, is purchased or transferred, or (ii) a supplier of the recycle derived syngas stream or downstream products made thereby ("supplier") operates within an allocation framework that allows for allocating a recycle content value to a portion or all of the recycle derived syngas stream or downstream products made thereby and to transfer the allotment to the manufacturer of the product or any intermediary who obtains a supply of recycle derived syngas stream or a downstream product thereof, from the supplier. In this system, one need not trace the source of a reactant compound or composition back to the manufacture of recycle derived syngas stream or back to any atoms contained in the recycle derived syngas stream, but rather can use any reactant compound or composition made by any process and have associated with such reactant compound or composition, or have associated with the Recycle PIA, a recycle content allotment. In an embodiment, the Recycle PIA reactants do not contain recycle content.

As used herein, a compound or composition includes liquids, solids, formulations, polymers, and each to the solids can be in any form, including pellets, sheets, films, strands, mats, webs, fibers, flake, extrudates, agglomerates, etc.

In an embodiment, the Recycle PIA has associated with it, or contains, or is labelled, advertised, or certified as containing recycle content in an amount of at least 0.01 wt. %, or at least 0.05 wt. %, or at least 0.1 wt. %, or at least 0.5 wt. %, or at least 0.75 wt. %, or at least 1 wt. %, or at least 1.25 wt. %, or at least 1.5 wt. %, or at least 1.75 wt. %, or at least 2 wt. %, or at least 2.25 wt. %, or at least 2.5 wt. %, or at least 2.75 wt. %, or at least 3 wt. %, or at least 3.5 wt. %, or at least 4 wt. %, or at least 4.5 wt. %, or at least 5 wt. %, or at least 6 wt. %, or at least 7 wt. %, or at least 10 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 65 wt. % and/or the amount can be up to 100 wt. %, or up to 95 wt. %, or up to 90 wt. %, or up to 80 wt. %, or up to 70 wt. %, or up to 60 wt. %, or up to 50 wt. %, or up to 40 wt. %, or up to 30 wt. %, or up to 25 wt. %, or up to 22 wt. %, or up to 20 wt. %, or up to 18 wt. %, or up to 16 wt. %, or up to 15 wt. %, or up to 14 wt. %, or up to 13 wt. %, or up to 11 wt. %, or up to 10 wt. %, or up to 8 wt. %, or up to 6 wt. %, or up to 5 wt. %, or up to 4 wt. %, or up to 3 wt. %, or up to 2 wt. %, or up to 1 wt. %, or up to 0.9 wt. %, or up to 0.8 wt. %, or up to 0.7 wt. %. The recycle content associated with the Recycle PIA can be associated by applying an allotment (credit or allocation) to any polymer and/or article made or sold. The allotment can be contained in an inventory of allotments created, maintained or operated by or for the Recycle PIA manufacturer. The allotment can be obtained from any source along any manufacturing chain of products provided that its origin is in gasifying a feedstock containing a solid fossil fuel and pre-ground CE.

The amount of recycle content in a reactant compound or composition, or the amount of recycle content applied to the Recycle PIA, or the amount of recycled CE (recycled CE feedstock) needed to feed the gasifier to claim a desired amount of recycle content in the Recycle PIA in the event that all the recycle content from the recycled CE feedstock is applied to the Recycle PIA, can be determined or calculated by any of the following methods:

(i) the amount of an allotment associated with the Recycle PIA is determined by the amount certified or declared by the supplier of transferred Recycle PIA, or
(ii) the amount of allocation declared by the entity using Recycle PIA, or
(iii) using a mass balance approach to back-calculate the minimum amount of recycle content in the feedstock from an amount of recycle content declared, advertised, or accounted for by the manufacturer, whether or not accurate, as applied to the Recycle PIA product,
(iv) blending of non-recycle content with pre-ground CE feedstock, or associating recycle content to a portion of the feedstock, using pro-rata mass approach In one embodiment, the Recycle PIA manufacturer can make Recycle PIA, or process a reactant compound or composition and make a Recycle PIA, or make Recycle PIA by obtaining any source of a reactant compound or composition from a supplier, whether or not such reactant compound or composition has any recycle content, and either:

i. from the same supplier of the reactant compound or composition, also obtain a recycle content allotment applied to either syngas or to any product, article, polymer, or composition, or
ii. from any person or entity, obtaining a recycle content allotment without a supply of a reactant compound or composition from said person or entity transferring said recycle content allotment.

The allotment in (i) can be obtained from a supplier of the reactant compound or composition used to make Recycle PIA, and the supplier also supplies and transfers the reactant compound or composition to the Recycle PIA manufacturer or within its Family of Entities. The circumstance described in (i) allows a Recycle PIA manufacturer to obtain a supply of a reactant compound or composition that has non-recycle content, yet obtain a recycle content allotment from the reactant compound or composition. In one embodiment, the reactant compound or composition supplier transfers a recycle content allotment to the Recycle PIA manufacturer as well as a supply of reactant compound or composition to the Recycle PIA manufacturer, where the recycle content allotment is not associated with the reactant compound or composition supplied, provided that the recycle content allotment transferred has its origins in gasifying recycled pre-ground CE. The recycle content allotment does not have to be tied to an amount of recycle content in a reactant compound or composition or to any monomer used to make Recycle PIA, but rather the recycle content allotment transferred by the reactant compound or composition supplier can be associated with other products having their origin in a recycle derived syngas stream other than those in a reaction scheme to make polymer and/or articles. For example, the reactant compound or composition can transfer to the Recycle PIA manufacturer a recycle content associated with r-butyraldehyde and also supply a quantity of propionic anhydride even though r-butyraldehyde is not used directly or via downstream products in the synthesis of the polymer and/or article such as a cellulose diacetate. This allows flexibility among the reactant compound or composition supplier and Recycle PIA manufacturer to apportion a recycle content among the variety of products they each make. In each of these cases, however, the recycle content allotment has its origins in gasifying recycle CE.

In one embodiment, the reactant compound or composition supplier transfers a recycle content allotment to the Recycle PIA manufacturer and a supply of reactant compound or composition to the Recycle PIA manufacturer, where the recycle content allotment is associated with reactant compound or composition. Optionally, the reactant compound or composition being supplied can be derived from recycled CE feedstock and at least a portion of the recycle content allotment being transferred can be the recycle content in the reactant compound or composition. The recycle content allotment transferred to the Recycle PIA manufacturer can be up front with the reactant compound or composition supplied, optionally in installments, or with each reactant compound or composition portion supplier, or apportioned as desired among the parties.

The allotment in (ii) is obtained by the Recycle PIA manufacturer (or its Family of Entities) from any person or entity without obtaining a supply of reactant compound or composition from the person or entity. The person or entity can be a reactant compound or composition manufacturer that does not supply reactant compound or composition to the Recycle PIA manufacturer or its Family of Entities, or the person or entity can be a manufacturer that does not make a reactant compound or composition. In either case, the circumstances of (ii) allows a Recycle PIA manufacturer to obtain a recycle content allotment without having to purchase any reactant compound or composition from the entity supplying the recycle content allotment. For example, the person or entity may transfer a recycle content allotment through a buy/sell model or contract to the Recycle PIA manufacturer or its Family of Entities without requiring purchase or sale of an allotment (e.g. as a product swap of products that are not reactant compound or composition), or the person or entity may outright sell the allotment to the Recycle PIA manufacturer or one among its Family of Entities. Alternatively, the person or entity may transfer a product, other than a reactant compound or composition, along with its associated recycle content allotment to the Recycle PIA manufacturer. This can be attractive to a Recycle PIA manufacturer that has a diversified business making a variety of products other than Recycle PIA requiring raw materials other than a reactant compound or composition that the person or entity can supply to the Recycle PIA manufacturer.

The allotment can be deposited into a recycle inventory (e.g. an inventory of allotments). In one embodiment, the allotment is an allocation created by the manufacturer of the recycle derived syngas stream. The Recycle PIA manufacturer can also make a polymer and/or article, whether or not a recycle content is applied to the polymer and/or article and whether or not recycle content, if applied to the polymer and/or article, is drawn from the inventory. For example, either the recycle derived syngas stream manufacturer and/or the Recycle PIA manufacturer may:

- a. deposit the allotment into an inventory and merely store it; or
- b. deposit the allotment into an inventory and apply allotments from the inventory to products other than:
  - i. any products derived directly or indirectly from the recycle derived syngas stream, or
  - ii. to a polymer and/or articles made by the Recycle PIA manufacturer, or
- c. sell or transfer an allocation from the inventory into which at least one allotment, obtained as noted above, was deposited.

If desired, however, from that inventory, any recycle content allotment can be deducted in any amount and applied to a polymer and/or article to make a Recycle PIA. For example, a Recycle inventory of allotments can be generated having a variety of sources for creating the allotments. Some recycle content allotments (credits) can have their origin in methanolysis of recycle waste, or from mechanical recycling of waste plastic or metal recycling, and/or from pyrolyzing recycle waste, or from any other chemical or mechanical recycling technology. The recycle inventory may or may not track the origin or basis of obtaining a recycle content value, or the inventory may not allow one to associate the origin or basis of an allocation to the allocation applied to Recycle PIA. It is sufficient that an allocation is deducted from an allocation inventory and applied to Recycle PIA regardless of the source or origin of the allocation, provided that a recycle content allotment derived from a recycled CE feedstock containing a solid fossil fuel and pre-ground CE is present in the allotment inventory as the time of withdrawal, or a recycle content allotment is obtained by the Recycle PIA manufacturer as specified in step (i) or step (ii), whether or not that recycle content allotment is actually deposited into the inventory. In one embodiment, the recycle content allotment obtained in step (i) or (ii) is deposited into an inventory of allotments. In one embodiment, the recycle content allotment deducted from the inventory and applied to the Recycle PIA originates from gasifying a recycled CE feedstock containing a solid fossil fuel and pre-ground CE.

As used throughout, the inventory of allotments can be owned by the recycle derived syngas manufacturer, or by the Recycle PIA manufacturer, or operated by either of them, or owned or operated by neither but at least in part for the benefit of either of them, or licensed by either of them. Also, as used throughout, the recycle derived syngas manufacturer or the Recycle PIA manufacturer may also include either of their Family of Entities. For example, while either of them may not own or operate the inventory, one among its Family of Entities may own such a platform, or license it from an independent vendor, or operate it for either of them. Alternatively, an independent entity may own and/or operate the inventory and for a service fee operate and/or manage at least a portion of the inventory for either of them.

In one embodiment, the Recycle PIA manufacturer obtains a supply of reactant compound or composition from a supplier, and also obtains an allotment from the supplier, where such allotment is derived from gasifying a feedstock containing a solid fossil fuel and pre-ground CE, and optionally the allotment is associated with the reactant compound or composition supplied. In one embodiment, at least a portion of the allotment obtained by the Recycle PIA manufacturer is either:

- a. applied to Recycle PIA made by the supply of reactant compound or composition;
- b. applied to Recycle PIA not made by the supply of reactant compound or composition, such as would be the case where Recycle PIA is already made and stored in inventory or future made Recycle PIA; or
- c. deposited into an inventory from which is deducted an allocation applied to Recycle PIA (the Recycle PIA applied allocation) and the deposited allocation either does, or does not, contribute to the amount of allocations from which the Recycle PIA applied allocation is drawn.
- d. deposited into an inventory and stored.

It is not necessary in all embodiments that recycled CE feedstock is used to make Recycle PIA composition or that the Recycle PIA was obtained from a recycle content allotment associated with a reactant compound or composition. Further, it is not necessary that an allotment be applied to the recycled CE feedstock for making the Recycle PIA to which recycle content is applied. Rather, as noted above, the allotment, even if associated with a reactant compound or composition when the reactant compound or composition is obtained, can be deposited into an electronic inventory. In one embodiment, however, the reactant compound or composition associated with the allotment is used to make the Recycle PIA compound or composition. In one embodiment, the Recycle PIA is obtained from a recycle content allotment associated with gasifying a recycled CE feedstock. In one embodiment, at least a portion of the allotments obtained from gasifying solid fossil fuel and pre-ground CE are applied to Recycle PIA to make a Recycle PIA.

In one embodiment, the recycle derived syngas stream manufacturer generates an allotment by gasifying a combination of solid fossil fuel and pre-ground CE, and either:

a. applies the allotment to any compound or composition (whether liquid or solid or polymer in any form, including pellets, sheet, fibers, flake, etc.) made directly or indirectly (e.g. through a reaction scheme of several intermediates) from the recycle derived syngas stream; or
b. applies the allotment to a compound or composition not made directly or indirectly from the recycle derived syngas stream, such as would be the case where reactant compounds or compositions are already made and stored in inventory or future made non-recycle content reactant compounds or compositions; or
c. deposited into an inventory from which is deducted any allocation that is applied to reactant compounds or compositions; and the deposited allocation either is or is not associated with the particular allocation applied to the reactant compounds or compositions; or
d. is deposited into an inventory and stored for use at a later time.

There is now also be provided a package or a combination of a Recycle PIA and a recycle content identifier associated with Recycle PIA, where the identifier is or contains a representation that the Recycle PIA contains, or is sourced from or associated with a recycle content. The package can be any suitable package for containing a polymer and/or article, such as a plastic or metal drum, railroad car, isotainer, totes, polytotes, IBC totes, bottles, compressed bales, jerricans, and polybags. The identifier can be a certificate document, a product specification stating the recycle content, a label, a logo or certification mark from a certification agency representing that the article or package contains contents or the Recycle PIA contains, or is made from sources or associated with recycle content, or it can be electronic statements by the Recycle PIA manufacturer that accompany a purchase order or the product, or posted on a website as a statement, representation, or a logo representing that the Recycle PIA contains or is made from sources that are associated with or contain recycle content, or it can be an advertisement transmitted electronically, by or in a website, by email, or by television, or through a tradeshow, in each case that is associated with Recycle PIA. The identifier need not state or represent that the recycle content is derived from gasifying a feedstock containing a solid fossil fuel and pre-ground CE. Rather, the identifier can merely convey or communicate that the Recycle PIA has or is sourced from a recycle content, regardless of the source. However, the Recycle PIA has a recycle content allotment that, at least in part, originates from gasifying solid fossil fuels and recycled CE.

In one embodiment, one may communicate recycle content information about the Recycle PIA to a third party where such recycle content information is based on or derived from at least a portion of the allocation or credit. The third party may be a customer of the recycle derived syngas manufacturer or Recycle PIA manufacturer or supplier, or may be any other person or entity or governmental organization other than the entity owning the either of them. The communication may electronic, by document, by advertisement, or any other means of communication.

In one embodiment, there is provided a system or package comprising:

a. Recycle PIA or article made thereby, and
b. an identifier such as a credit, label or certification associated with said Recycle PIA or article made thereby, where the identifier is a representation that the polymer and/or article or article made thereby has, or is sourced from, a recycle content provided that the Recycle PIA or article made thereby has an allotment, or is made from a reactant compound or composition, at least in part originating directly or indirectly from gasifying solid fossil fuels and pre-ground recycle CE.

The system can be a physical combination, such as package having at least Recycle PIA as its contents and the package has a label, such as a logo, that the contents such as the Recycle PIA has or is sourced from a recycle content. Alternatively, the label or certification can be issued to a third party or customer as part of a standard operating procedure of an entity whenever it transfers or sells Recycle PIA having or sourced from recycle content. The identifier does not have to be physically on the Recycle PIA, or on a package, and does not have to be on any physical document that accompanies or is associated with the Recycle PIA. For example, the identifier can be an electronic credit transferred electronically by the Recycle PIA manufacturer to a customer in connection with the sale or transfer of the Recycle PIA product, and by sole virtue of being a credit, it is a representation that the Recycle PIA has recycle content. The identifier itself need only convey or communicate that the Recycle PIA has or is sourced from a recycle content, regardless of the source. In one embodiment, articles made from the Recycle PIA may have the identifier, such as a stamp or logo embedded or adhered to the article. In one embodiment, the identifier is an electronic recycle content credit from any source. In one embodiment, the identifier is an electronic recycle content credit having its origin in gasifying a feedstock containing a solid fossil fuel and pre-ground CE.

The Recycle PIA is made from a reactant compound or composition, whether or not the reactant is a recycle content reactant (recycled CE feedstock). Once a Recycle PIA composition is made, it can be designated as having recycle content based on and derived from at least a portion of the allotment, again whether or not the recycled CE feedstock is used to make the Recycle PIA composition. The allocation can be withdrawn or deducted from inventory. The amount of the deduction and/or applied to the Recycle PIA can correspond to any of the methods described above, e.g. a mass balance approach.

In an embodiment, a Recycle PIA compound or composition can be made by having an inventory of allocations, and reacting a reactant compound or composition a synthetic process to make a Recycle PIA, and applying a recycle content to that Recycle PIA to thereby obtain a Recycle PIA by deducting an amount of allocation from an inventory of allocations. A Recycle PIA manufacturer may have an inventory of allocations by itself or one among its Family of Entities owning, possessing, or operating the inventory, or a third party operating at least a portion of the inventory for the Recycle PIA manufacturer or its Family of Entities or as a service provided to the Recycle PIA manufacturer or one among its Family of Entities. The amount of allocation deducted from inventory is flexible and will depend on the amount of recycle content applied to the Recycle PIA. It should be at least sufficient to correspond with at least a portion if not the entire amount of recycle content applied to the Recycle PIA. The method of calculation can be a mass balance approach or a method of calculation described above. The inventory of allocations can be established on any basis and may be a mix of basis, provided that at least some amount of allocation in the inventory is attributable to gasifying a feedstock containing a solid fossil fuel and pre-ground CE. The recycle content allotment applied to the Recycle PIA does not have to have its origin in gasifying a feedstock containing a solid fossil fuel and pre-ground CE, and instead can have its origin in any other method of generating allocations from recycle waste, such as through methanolysis or gasification of recycle waste, provided that the inventory of allotments also contains an allotment or has an allotment deposit having its origin in gasifying a feedstock containing a solid fossil fuel and pre-ground CE. In one embodiment, however, the recycle content applied to the Recycle PIA is an allotment obtained from gasifying a feedstock containing a solid fossil fuel and pre-ground CE.

The following are examples of designating or declaring a recycle content to Recycle PIA or a recycle content to a reactant compound or composition:

1. A Recycle PIA manufacturer applies at least a portion of an allotment to a polymer and/or article composition where the allotment is associated with a pre-ground CE derived syngas stream, and the reactant compound or composition used to make the Recycle PIA did not contain any recycle content or it did contain recycle content; or
2. A Recycle PIA manufacturer applies at least a portion of an allotment to a polymer and/or article composition where the allotment is derived directly or indirectly with a recycle content reactant compound or composition, whether or not such reactant compound or composition volume is used to make the Recycle PIA; or
3. A Recycle PIA manufacturer applies at least a portion of an allotment to a Recycle PIA composition where the allotment is derived directly or indirectly from a recycled CE feedstock used to make the Recycle PIA to which the allotment is applied, and:
   a. all of the recycle content in the recycled CE feedstock is applied to determine the amount of recycle content in the Recycle PIA, or
   b. only a portion of the recycle content in the recycled CE feedstock is applied to determine the amount of recycle content applied to the Recycle PIA, the remainder stored in inventory for use to future Recycle PIA, or for application to other existing Recycle PIA made from recycled CE feedstock not containing any recycle content, or to increase the recycle content on an existing Recycle PIA, or a combination thereof, or
   c. none of the recycle content in the recycled CE feedstock is applied to the Recycle PIA and instead is stored in an inventory, and a recycle content from any source or origin is deducted from the inventory and applied to Recycle PIA; or
4. A Recycle PIA manufacturer applies at least a portion of an allotment to a reactant compound or composition used to make a Recycle PIA to thereby obtain a Recycle PIA, where the allotment was obtained with the transfer or purchase of the same reactant compound or composition used to make the Recycle PIA and the allotment is associated with the recycle content in a reactant compound or composition; or
5. A Recycle PIA manufacturer applies at least a portion of an allotment to a reactant compound or composition used to make a Recycle PIA to thereby obtain a Recycle PIA, where the allotment was obtained with the transfer or purchase of the same reactant compound or composition used to make the Recycle PIA and the allotment is not associated with the recycle content in a reactant compound or composition but rather on the recycle content of a monomer used to make the reactant compound or composition; or
6. A Recycle PIA manufacturer applies at least a portion of an allotment to a reactant compound or composition used to make a Recycle PIA to thereby obtain a Recycle PIA, where the allotment was not obtained with the transfer or purchase of the reactant compound or composition and the allotment is associated with the recycle content in the reactant compound or composition; or
7. A Recycle PIA manufacturer applies at least a portion of an allotment to a reactant compound or composition used to make a Recycle PIA to thereby obtain a Recycle PIA, where the allotment was not obtained with the transfer or purchase of the reactant compound or composition and the allotment is not associated with the recycle content in the reactant compound or composition but rather with the recycle content of any monomers used to make the reactant compound or composition; or
8. A Recycle PIA manufacturer obtains an allotment having it origin in gasifying a feedstock containing a solid fossil fuel and pre-ground CE, and:
   a. no portion of the allotment is applied to a reactant compound or composition to make Recycle PIA and at least a portion is applied to Recycle PIA to make a Recycle PIA; or
   b. less than the entire portion is applied to a reactant compound or composition used to make Recycle PIA and the remainder is stored in inventory or is applied to future made Recycle PIA or is applied to existing Recycle PIA in inventory.

In one embodiment, the Recycle PIA, or articles made thereby, can be offered for sale or sold as Recycle PIA containing or obtained with recycle content. The sale or offer for sale can be accompanied with a certification or representation of the recycle content claim made in association with the Recycle PIA or article made with the Recycle PIA.

The obtaining of an allocation and designating (whether internally such as through a bookkeeping or an inventory tracking software program or externally by way of declaration, certification, advertising, representing, etc.) can be by the Recycle PIA manufacturer or within the Recycle PIA manufacturer Family of Entities. The designation of at least a portion of the Recycle PIA as corresponding to at least a portion of the allotment (e.g. allocation or credit) can occur through a variety of means and according to the system employed by the Recycle PIA manufacturer, which can vary from manufacturer to manufacturer. For example, the designation can occur internally merely through a log entry in the books or files of the Recycle PIA manufacturer or other inventory software program, or through an advertisement or statement on a specification, on a package, on the product, by way of a logo associated with the product, by way of a certification declaration sheet associated with a product sold, or through formulas that compute the amount deducted from inventory relative to the amount of recycle content applied to a product.

Optionally, the Recycle PIA can be sold. In one embodiment, there is provided a method of offering to sell or selling polymer and/or articles by:

a. A Recycle PIA manufacturer or its Family of Entities obtaining or generating a recycle content allocation, and the allocation can be obtained by any of the means described herein and can be deposited into inventory, the recycle content allocation having its origin in gasification of a feedstock containing a solid fossil fuel and pre-ground CE,
b. converting a reactant compound or composition in a synthetic process to make a compound, composition, polymer and/or article composition,
c. designating (e.g. assigning or associating) a recycle content to at least a portion of the compound, composition, polymer and/or article composition from an inventory of allocations, where the inventory contains at least one entry that is an allocation having its origin in gasification of a feedstock containing a pre-ground CE. The designation can be the amount of allocation deducted from inventory, or the amount of recycle content declared or determined by the Recycle PIA manufacturer in its accounts. Thus, the amount of recycle content does not necessarily have to be applied to the Recycle PIA product in a physical fashion. The designation can be an internal designation to or by the Recycle PIA manufacturer or its Family of Entities or a service provider in contractual relationship to the Recycle PIA manufacturer or its Family of Entities, and
d. offering to sell or selling the compound, composition, polymer and/or article composition as containing or obtained with recycle content corresponding at least in part with such designation. The amount of recycle content represented as contained in the Recycle PIA sold or offered for sale has a relationship or linkage to the designation. The amount of recycle content can be a 1:1 relationship in the amount of recycle content declared on a Recycle PIA offered for sale or sold and the amount of recycle content assigned or designated to the Recycle PIA by the Recycle PIA manufacturer.

The steps described need not be sequential, and can be independent from each other. For example, the step a) of obtaining an allocation and the step of making Recycle PIA from a reactant compound or composition can be simultaneous and related if one employs a recycled CE feedstock composition to make the Recycle PIA since the recycled CE feedstock is both a reactant compound or composition and has a recycle content allocation associated with it.

As used throughout, the step of deducting an allocation from an inventory of allocations does not require its application to a Recycle PIA product. The deduction also does not mean that the quantity disappears or is removed from the inventory logs. A deduction can be an adjustment of an entry, a withdrawal, an addition of an entry as a debit, or any other algorithm that adjusts inputs and outputs based on an amount recycle content associated with a product and one or a cumulative amount of allocations on deposit in the inventory. For example, a deduction can be a simple step of a reducing/debit entry from one column and an addition/credit to another column within the same program or books, or an algorithm that automates the deductions and entries/additions and/or applications or designations to a product slate. The step of applying an allocation to a Recycle PIA product where such allocation was deducted from inventory also does not require the allocation to be applied physically to a Recycle PIA product or to any document issued in association with the Recycle PIA product sold. For example, a Recycle PIA manufacturer may ship Recycle PIA product to a customer and satisfy the "application" of the allocation to the Recycle PIA product by electronically transferring a recycle content credit to the customer.

In one embodiment, the amount of recycle content in the recycled CE feedstock or in the Recycle PIA will be based on the allocation or credit obtained by the manufacturer of the Recycle PIA composition or the amount available in the Recycle PIA manufacturer's inventory of allotments. A portion or all of the allocation or credit obtained by or in the possession of a manufacturer of Recycle PIA can be designated and assigned to a recycled CE feedstock or Recycle PIA on a mass balance basis. The assigned value of the recycle content to the recycled CE feedstock or Recycle PIA should not exceed the total amount of all allocations and/or credits available to the manufacturer of the Recycle PIA or other entity authorized to assign a recycle content value to the Recycle PIA.

In an aspect, there is now also provided a method of introducing or establishing a recycle content in a compound, composition, polymer and/or article without necessarily using reactant compound or composition having recycle content. In this method, a. a syngas manufacturer makes a recycled CE derived syngas stream and
b. a polymer and/or article manufacturer:
    i. obtains an allotment having it origin in gasifying recycle CE, or derived from said recycled CE derived syngas stream, the syngas manufacturer or from a third-party transferring said allotment,
    ii. makes a polymer and/or article from any reactant compound or composition, and
    iii. associates at least a portion of the allotment with at least a portion of the polymer and/or article, whether or not the reactant compound or composition used to make the polymer and/or article contains a recycle content.

In this method, the polymer and/or article manufacturer need not purchase a recycle reactant compound or composition from a particular source or supplier, and does not require the polymer and/or article manufacturer to use or purchase a reactant compound or composition having recycle content in order to successfully establish a recycle content in the polymer and/or article composition. The polymer or article manufacturer may use any source of reactant compound or composition and apply at least a portion of the allocation or credit to at least a portion of the reactant compound or composition feedstock or to at least a portion of the polymer and/or article product. The association by the polymer and/or article manufacturer may come in any form, whether by on in its inventory, internal accounting methods, or declarations or claims made to a third party or the public.

There is also provided a use for a reactant compound or composition, the use including converting recycled pre-ground CE in any synthetic process, such as gasification, to make syngas and/or Recycle PIA.

There is also provided a use for a recycle pre-ground CE that includes converting a reactant compound or composition in a synthetic process to make polymer and/or articles and applying at least a portion of an allotment to the polymer and/or article to the reactant compound or composition, where the allotment has its origin in gasifying a feedstock containing a solid fossil fuel and recycle pre-ground CE or has its origin in an inventory of allotments where at least one deposit made into the inventory has its origin in gasifying a feedstock containing a solid fossil fuel and recycle pre-ground CE.

In one embodiment, there is provided a polymer and/or article composition that is obtained by any of the methods described above.

The reactant compound or composition, such a reactant compound or composition can be stored in a storage vessel and transferred to a Recycle PIA manufacturing facility by way of truck, pipe, or ship, or as further described below, the reactant compound or composition production facility can be integrated with the Recycle PIA facility. The reactant compound or composition may be shipped or transferred to the operator or facility that makes the polymer and/or article.

In an embodiment, the process for making Recycle PIA can be an integrated process. One such example is a process to make Recycle PIA by:

a. gasifying a feedstock containing a solid fossil fuel and recycle pre-ground CE to make a recycle derived syngas stream; and
b. reacting said recycle derived syngas or a non-recycle content syngas made in the gasifier in a reaction scheme to make a reactant compound or composition;
c. reacting any reactant compound or composition in a synthetic process to make a polymer and/or article;
d. depositing an allotment into an inventory of allotments, said allotment originating from gasifying a feedstock containing a solid fossil fuel and recycle pre-ground CE; and
e. applying any allotment from said inventory to the polymer and/or article to thereby obtain a recycle content polymer and/or article composition.

In one embodiment, one may integrate two or more facilities and make Recycle PIA. The facilities to make Recycle PIA, the reactant compound or composition, or the syngas can be stand-alone facilities or facilities integrated to each other. For example, one may establish a system of producing and consuming a reactant compound or composition, as follows:

a. provide a reactant compound or composition manufacturing facility configured to produce a reactant compound or composition;
b. provide a polymer and/or article manufacturing facility having a reactor configured to accept a reactant compound or composition from the reactant compound or composition manufacturing facility and making a polymer and/or article; and
c. a supply system providing fluid communication between these two facilities and capable of supplying a reactant compound or composition from the reactant compound or composition manufacturing facility to the polymer and/or article manufacturing facility, wherein the reactant compound or composition manufacturing facility generates allotments from gasifying a feedstock containing solid fossil fuel and recycle pre-ground CE, and:

1. said allotments are applied to the reactants compounds or compositions or to the polymer and/or article reactant, or
2. are deposited into an inventory of allotments, and any allotment is withdrawn from the inventory an applied to the reactant compounds or compositions or to the polymer and/or article.

The reactant compound or composition manufacturing facility can make Recycle PIA by accepting any reactant compound or composition from the reactant compound or composition manufacturing facility and applying a recycle content to a polymer and/or article made with the reactant compound or composition by deducting allotments from its inventory and applying them to the Recycle PIA, optionally in amounts using the methods described above. The allotments withdrawn from inventory and applied can be allotments obtained by any source of recycle content, and need not necessarily be allotments associated with gasifying recycle pre-ground CE.

In one embodiment, there is also provided a system for producing Recycle PIA as follows:

a. provide a gasification manufacturing facility configured to produce an output composition comprising a recycle derived syngas stream;
b. provide a reactant compound or composition manufacturing facility configured to accept a recycle derived syngas stream from the gasification manufacturing facility and making, through a reaction scheme one or more downstream products of said syngas to make an output composition comprising a reactant compound or composition;
c. provide a polymer and/or article manufacturing facility having a reactor configured to accept a reactant compound or composition and making an output composition comprising a recycle content Recycle PIA; and
d. a supply system providing fluid communication between at least two of these facilities and capable of supplying the output composition of one manufacturing facility to another one or more of said manufacturing facilities.

The polymer and/or article manufacturing facility can make Recycle PIA. In this system, the gasification manufacturing facility can have its output in fluid communication with the reactant compound or composition manufacturing facility which in turn can have its output in fluid communication with the polymer and/or article manufacturing facility. Alternatively, the manufacturing facilities of a) and b) alone can be in fluid communication, or only b) and c). In the latter case, the polymer and/or article manufacturing facility can make Recycle PIA directly by having the pre-ground CE content syngas produced in the gasification manufacturing facility converted all the way to Recycle PIA, or indirectly by accepting any reactant compound or composition from the reactant compound or composition manufacturing facility and applying a recycle content to Recycle PIA by deducting allotments from its inventory and applying them to the Recycle PIA, optionally in amounts using the methods described above. The allotments obtained and stored in inventory can be obtained by any of the methods described above, The fluid communication can be gaseous or liquid or both. The fluid communication need not be continuous and can be interrupted by storage tanks, valves, or other purification or treatment facilities, so long as the fluid can be transported from the manufacturing facility to the subsequent facility through an interconnecting pipe network and without the use of truck, train, ship, or airplane. Further, the facilities may share the same site, or in other words, one site may contain two or more of the facilities. Additionally, the facilities may also share storage tank sites, or storage tanks for ancillary chemicals, or may also share utilities, steam or other heat sources, etc., yet also be considered as discrete facilities since their unit operations are separate. A facility will typically be bounded by a battery limit.

In one embodiment, the integrated process includes at least two facilities co-located within 5, or within 3, or within 2, or within 1 mile of each other (measured as a straight line). In one embodiment, at least two facilities are owned by the same Family of Entities.

In an embodiment, there is also provided an integrated Recycle PIA generating and consumption system. This system includes:

a. Provide a gasification manufacturing facility configured to produce an output composition comprising a recycle derived syngas stream obtained by gasifying solid fossil fuel and recycled pre-ground CE;
b. provide a reactant compound or composition manufacturing facility configured to accept a recycle derived syngas stream from the gasification manufacturing facility and making, through a reaction scheme, one or more downstream products of said syngas to make an output composition comprising a reactant compound or composition;
c. provide a polymer and/or article manufacturing facility having a reactor configured to accept said reactant compound or composition and making an output composition comprising a polymer and/or article; and
d. a piping system interconnecting at least two of said facilities, optionally with intermediate processing equipment or storage facilities, capable of taking off the output composition from one facility and accept said output at any one or more of the other facilities.

The system does not necessarily require a fluid communication between the two facilities, although fluid communication is desirable. For example, the recycle derived syngas can be delivered to the reactant compound or composition facility through the interconnecting piping network that can be interrupted by other processing equipment, such as treatment, purification, pumps, compression, or equipment adapted to combine streams, or storage facilities, all containing optional metering, valving, or interlock equipment. The equipment can be a fixed to the ground or fixed to structures that are fixed to the ground. The interconnecting piping does not need to connect to the reactant compound or composition reactor or the cracker, but rather to a delivery and receiving point at the respective facilities. The interconnecting pipework need not connect all three facilities to each other, but rather the interconnecting pipework can be between facilities a)-b), or b)-c), or between a)-b)-c).

In embodiments, the Recycle PIA described herein is a Recycle CE as described herein. In embodiments, the feedstock for making recycled CE content syngas (according to any of the processes described herein) comprises recycled materials and/or articles that contain Recycle CE, such that a circular (or at least partial closed-loop) recycle process is created or established. For example, eyeglass frames made from or containing Recycle CE (as described herein), or scrap material from a process for making such frames, is/are recycled and used in the feedstock for making recycled CE content syngas, which syngas is then used again for producing (or associated with producing) Recycle CE containing eyeglass frames. Basically, the circular recycle process (or system) utilizes recycle content for producing the same type of materials or products that were recycled (were the recycle content is established from such recycled materials or products).

In an embodiment, the total amount of carbon in the pre-ground CE and plastics added to the solid fossil fuel is at least 70 wt. %, or at least 75 wt. %, or at least 80 wt. %.

The total amount of hydrogen in the pre-ground CE and plastics is desirably at least 5 wt. %, or at least 8 wt. %, or at least 10 wt. %.

In another embodiment, the ratio of total hydrogen to total carbon in the CE and plastics feed is higher than that of the solid fossil fuel. In one embodiment or in any of the mentioned embodiments, the ratio of total hydrogen to total carbon in the pre-ground CE and plastics used in the feedstock is at least 0.075, or at least 0.08, or at least 0.085, or at least 0.09, or at least 0.095, or at least 0.1, or at least 0.11, or at least 0.12, or at least 0.13.

In another embodiment, the pre-ground CE and plastics used in the feedstock stream have an average fixed carbon content of less than 75 wt. %, or not more than 70 wt. %, or not more than 65 wt. %, or not more than 60 wt. %, or not more than 55 wt. %, or not more than 45 wt. %, or not more than 40 wt. %, or not more than 35 wt. %, or not more than 30 wt. %, or not more than 25 wt. %, or not more than 20 wt. %, or not more than 15 wt. %, or not more than 10 wt. %, or not more than 8 wt. %, or not more than 6 wt. %, or not more than 5 wt. %, or not more than 4 wt. %, or not more than 3 wt. %, or not more than 2 wt. %, or not more than 1 wt. %, based on the weight of the pre-ground CE and plastics. The fixed carbon content is the combustible solids remaining (other than ash) after the coal is heated and volatiles removed. It can be determined by subtracting the percentages of moisture, volatile matter, and ash from a sample. If a solid is employed with a large mismatch in fixed carbon content, variations in syngas composition can be experienced outside of desirable limits. For example, a solid that has a very low fixed carbon content could, in an entrainment flow high temperature gasifier, gasify more readily than coal proceed from making carbon monoxide to generating more carbon dioxide within the residence time experienced by coal, while a co-feed of solids having a much higher fixed carbon content that coal would take longer to gasify and generate more unconverted solids. The degree of syngas compositional variations that can be tolerated will depend on the use of the syngas, and in the case of making chemicals, it is desirably to minimize the factors that could cause wider syngas compositional variations. In the process of the invention, syngas compositional variations attributable to the use of CE and plastics are negligible due by keeping the plastics concentration in the solids low.

In another embodiment, the pre-ground CE and plastics used in the feedstock stream have an average fixed carbon content that is at least 3% less, or at least 5% less, or at least 7% less, or at least 9% less, or at least 10% less, or at least 13% less, or at least 15% less, or at least 17% less, or at least 20% less, or at least 23% less, or at least 25% less, or at least 27% less, or at least 30% less, or at least 32% less, or at least 35% less, or at least 38% less, or at least 40% less, or at least 43% less, or at least 45% less, or at least 47% less, or at least 50% less, or at least 55% less, or at least 60% less, or at least 70% less, or at least 80% less, or at least 90% less, or at least 95% less, than the fixed carbon content of coal, or optionally all solid fossil fuel employed in the feedstock stream, or optionally any solids other than CE and plastics.

The pre-ground CE and plastics can have an average sulfur content that is low or only in trace amounts. The pre-ground CE and plastics have an average sulfur content of up to 5 wt. %, or up to 4 wt. %, or up to 3.5 wt. %, or up to 3 wt. %, or up to 2.5 wt. %, or up to 2 wt. %, or up to 1.5 wt. %, or up to 1 wt. %, or up to 0.5 wt. %, or up to 0.25 wt. %, or up to 0.1 wt. %, or up to 0.05 wt. %, or up to 0.01 wt. %, or up to 0.005 wt. %, based on the weight of the pre-ground CE and plastics.

The pre-ground CE and plastics may have a widely varying ash content depending on the type of plastics in the CE and plastics stream and the purity the CE and plastics stream to the select CE and plastic. The pre-ground CE and plastics may have an average ash content of at least 1 wt. %, or at least 2 wt. %, or at least 3 wt. %, or at least 4 wt. %, or at least 10 wt. %, or at least 15 wt. %, or at least 20 wt.

%, or at least 25 wt. %, or at least 30 wt. %, or at least 35 wt. %, or at least 40 wt. %, or at least 45 wt. % based on the weight of the pre-ground CE and plastics. The pre-ground CE and plastics may have an average ash content of not more than 60 wt. %, or not more than 55 wt. %, or not more than 55 wt. %, or not more than 55 wt. %, or not more than 55 wt. %, or not more than 40 wt. %, or not more than 30 wt. %, or not more than 20 wt. %, or not more than 15 wt. %, or not more than 10 wt. %, desirably not more than 8 wt. %, or not more than 7 wt. %, or not more than 6 wt. %, or not more than 5.5 wt. %, or not more than 5 wt. %, or not more than 4.5 wt. %, or not more than 4 wt. %, or not more than 3 wt. %, or not more than 2.5 wt. %, based on the weight of the pre-ground CE and plastics.

In another embodiment, the average oxygen content in the CE and plastics can be at zero or at least 0.1 wt. %, or at least 0.5 wt. %, or at least 1 wt. %, or at least 2 wt. %, or at least 4 wt. %, or at least 6 wt. %, or at least 8 wt. %, or at least 10 wt. %, or at least 13 wt. %, or at least 15 wt. %, or at least 18 wt. %, or at least 20 wt. %. Desirably, to improve the HHV, the amount of oxygen is kept low, such as not more than 20 wt. %, or not more than 15 wt. %, or not more than 10 wt. %, or not more than 8 wt. %, or not more than 5 wt. %, or not more than 4 wt. %, or not more than 2 wt. %, or not more than 1 wt. %, based on the weight of the pre-ground CE and plastics.

The content of minerals, metals and elements other than carbon, hydrogen, oxygen, nitrogen, and sulfur, in the pre-ground CE and plastics can be at least 0.01 wt. %, or at least 0.1 wt. %, or at least 0.5 wt. %, or at least 1 wt. %, or at least 1.5 wt. %, or at least 1.8 wt. %, or at least 2 wt. %, or at least 2.3 wt. %, or at least 2.5 wt. %, or at least 2.8 wt. %, or at least 3 wt. %, based on the weight of the pre-ground CE and plastics. The upper amount is not particularly limited, and generally would not exceed 8 wt. %, or not exceed 7 wt. %, or not exceed 6 wt. %, or not exceed 5 wt. %, or not exceed 4.5 wt. %, or not exceed 4 wt. %, or not exceed 3.8 wt. %.

The CE and plastics charged to the gasifier have been treated by at least one granulation step to reduce the size of the CE and plastics from either their original form or from their form as shredded/chipped CE and plastics having an average size of ¼ inch or more in their longest dimension. Desirably, the CE and plastics, prior to arrival at a gasification facility, have been treated with a first pass of granulation or shredding from the original form of the CE and plastic. The coarsely granulated CE and plastics are then further finely granulated, and optionally further pulverizing or milled, to the final desired particle size. The gasification facility can receive pre-granulated CE and plastics at their final particle size, or can receive coarsely ground CE and plastics and the operator/owner of the gasification facility can conduct the granulation step(s) necessary to obtain the desired particle size present in the feedstock stream.

The CE and plastics are ground prior to addition to other fossil fuels, meaning they are ground, and optionally but desirably sieved, to the final particle size prior to combining them with the solid fossil fuel ("pre-ground CE and plastics"). As explained below, the CE and plastics in their original size, or as coarsely ground (e.g. average of ¼ inch or more in their largest dimension or even 0.5 inches or more), cannot be processed through an entrained flow coal gasifier. Further, the elasticity of the CE and plastics makes them unsuited for co-granulating with more hard and brittle carbonaceous fuel sources like coal or pet coke.

The CE and plastics are pre-ground to a suitable particle size, optionally sieved, and then combined with one or more fossil fuel components of the feedstock stream at any location prior to introducing the feedstock stream into gasification zone within the gasifier. As noted above, CE and plastics are not easily ground concurrently in the same equipment used to grind coal, particularly in a slurry, since many of the CE and plastics are soft, elastic and non-friable. However, the coal grinding equipment will provide an excellent source of energy for mixing pre-ground CE and plastics with the fossil fuel while reducing the size of the coal particles. Therefore, one of the desirable locations for combining pre-ground CE and plastics having a target size for feeding into the gasifier is into the equipment used for grinding the other carbonaceous fossil fuel sources (e.g. coal, pet-coke). This location is particularly attractive in a slurry fed gasifier because it is desirable to use a feed having the highest stable solids concentration possible, and at higher solids concentration, the viscosity of the slurry is also high. The torque and shear forces employed in fossil fuel grinding equipment is high, and coupled with the shear thinning behavior of a coal slurry, good mixing of the pre-ground CE and plastics with the ground fossil fuel can be obtained in the fossil fuel grinding equipment.

Other locations for combining pre-ground CE and plastics with fossil fuel sources can be onto the fossil fuel loaded on the main fossil fuel belt feeding a grinder, or onto the main fossil fuel belt feeding a grinder before the fossil fuel is loaded onto the belt, or into a fossil fuel slurry storage tank containing a slurry of fossil fuel ground to the final size, particularly if the storage tank is agitated.

Figure 5:
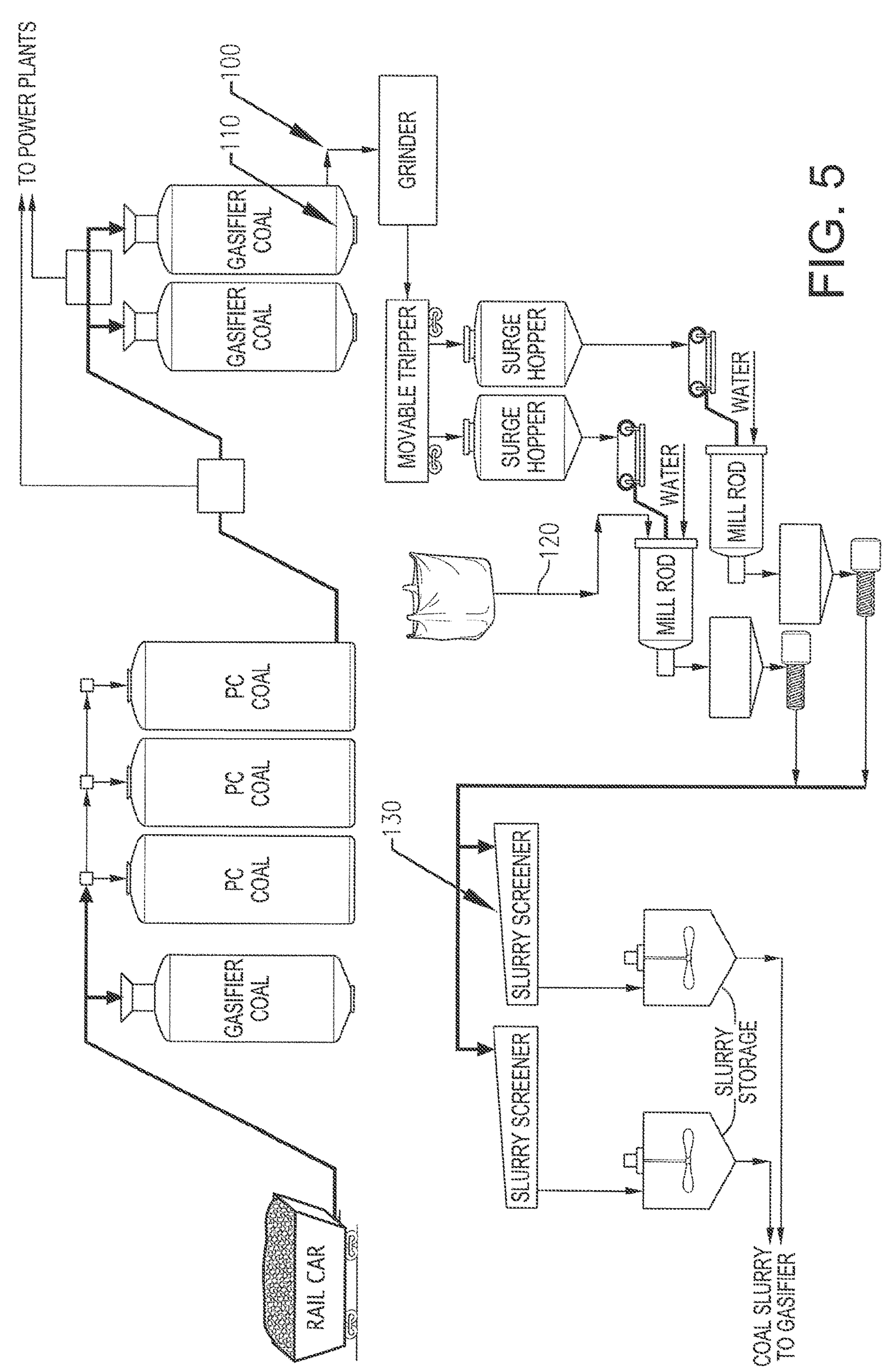
FIG. 5 is a detailed view of the locations for adding recycled CE (and optional other plastics) to a solid fossil fuel.

There are several locations that provide a safe, economic and effective way to introduce pre-ground solid CE/plastic comprising recycled CE to a slurry fed coal gasifier. In additional embodiments of the invention, FIG. 5 shows four locations where recycle CE content can be introduced. All of these points are in the low-pressure section (lower than the pressure within the gasifier or gasification zone) of the process thus reducing the cost of modifications.

In an embodiment of the invention shown in FIG. 5, the recycle CE content can be introduced at location 100, the main coal feed belt. The CE and optional plastics are metered onto the main coal feed belt as it moves past with the coal feed already loaded onto the belt. The CE and optional plastics are added to the belt using a weigh belt feeder, or other similar device, to measure the mass of the material, and the speed of the belt to determine addition rate. Coal is similarly added to the same belt and would be underneath the CE and optional plastics. The combined solid mixture of the coal and CE and optional plastics in the proper ratio are then conveyed to surge hoppers and other storage and conveying equipment until it is ultimately fed to the coal grinding mill. In the coal grinding mill, the coal, CE and optional plastics, water and viscosity modifiers are mixed thoroughly, and the coal is reduced in size to the target grind size distribution and the mixture becomes a viscous slurry. The CE and optional plastics undergoes very little or no size reduction since it is a softer material, but benefits from the extreme mixing in the mill due to its inclusion into the slurry production process. The CE and optional plastics have been pre-ground to the target size (e.g. less than 2 mm) and do not need any further size reduction.

In another embodiment of the invention, recycled CE content can be introduced as shown in FIG. 5 location number 110. This is the same process as described in location number 100 above, except that the CE and optional plastics are added to the main coal belt first, before the coal is added. In this manner, coal is on top. Since the CE and optional plastics will be pre-ground and may inherently be less dense than coal, it may be easier for this material to be blown off of the belt in a strong wind. With the much coarser and more dense coal covering the recycled material, this dusting and loss of material will be greatly reduced.

In another embodiment the invention, the recycled CE content can be added at location number 120, the grinding mill. The existing equipment, coal, water and viscosity modifiers are already added to the grinding mill to reduce the particle size of the coal and produce a viscous slurry high in solids. The CE and optional plastics can be independently conveyed to the entry point of the mill and added directly to the mill in the proper ratio. The mill will then grind the coal, produce the slurry and thoroughly mix in the CE and optional plastics in the process. This avoids wind and weather effects on the coal, recycled material mixture.

In yet another embodiment of the invention the recycled CE content can be introduced at location number 130, the slurry storage tank. Since the CE and optional plastics are pre-ground to the proper particle size for introduction into the gasifier, it can be added to the slurry storage tank directly after the grinding/slurry operation. Alternatively, it can be added to the tank through a separate screen or the screen used by the slurry to ensure no large particles are passed to the tank. This is the last low-pressure addition point before the slurry is pumped at pressure to the gasifier. This will minimize the amount of material in process that is mixed together. The agitation in the slurry tanks will mix in the CE and optional plastics to ensure it is evenly distributed.

The fossil fuel (coal or petcoke) and the CE and plastics are ground or milled for multiple purposes. The CE and plastics must be ground to a small size as does the fossil fuel source to (i) allow for faster reaction once inside the gasifier due to mass transfer limitations, (ii) to create a slurry that is stable, fluid and flowable at high concentrations of solids to water, and (iii) to pass through processing equipment such as high-pressure pumps, valves, and feed injectors that have tight clearances. Typically, this means that the solids in the feedstock, including the CE and plastics, are ground to a particle size of 2 mm or smaller. As used throughout, a stated particle size means that at least 90 wt. % of the particles have a largest dimension in the stated size, or alternatively that 90 wt. % passes through sieve designated for that particle size. Either conditions satisfy the particle size designation. Larger size CE and plastics have the potential for being blown through the gasification zone without completely gasifying, particularly when the gasification conditions are established to gasify solid fossil fuel having a particle dimension of 2 mm or smaller.

The CE and plastics are desirably ground to a particle size that, after optional sieving, is acceptable for gasifying within the design parameters of the gasifier. Desirably, the particle size of the CE and plastics used in the feedstock, or as fed to or combined with a solid fuel, is 2 mm and smaller or constitute those particles passing through a 10 mesh, or 1.7 mm or smaller those particles passing through a 12 mesh), or 1.4 mm or smaller (those particles passing through a 14 mesh), or 1.2 mm or smaller (those particles passing through a 16 mesh), or 1 mm or smaller (those particles passing through a 18 mesh), or 0.85 mm or smaller (those particles passing through a 20 mesh), or 0.7 mm or smaller (those particles passing through a 25 mesh) or 0.6 mm or smaller (those particles passing through a 30 mesh), or 0.5 mm or smaller (those particles passing through a 35 mesh), or 0.4 mm or smaller (those particles passing through a 40 mesh), or 0.35 mm or smaller (those particles passing through a 45 mesh), or 0.3 mm or smaller (those particles passing through a 50 mesh), or 0.25 mm or smaller (those particles passing through a 60 mesh), or 0.15 mm or smaller (those particles passing through a 100 mesh), or 0.1 mm or smaller (those particles passing through a 140 mesh), or 0.07 mm or smaller (those particles passing through a 200 mesh), or 0.044 mm or smaller (those particles passing through a 325 mesh), or 0.037 mm or smaller (those particles passing through a 400 mesh). In another embodiment, the size of the ground CE and plastic particles is at least 0.037 mm (or 90% retained on a 400 mesh). The sample of pre-ground CE and plastics will be considered to be within a stated particle size limit if 90 vol. % of the sample is within the stated limits.

In one embodiment or in any of the mentioned embodiments, the 90% of the particle size of the pre-ground CE and plastics as used in the feedstock composition is 1 mm or smaller in its largest dimension, or 0.5 mm or smaller, or 0.25 mm or smaller, or 0.1 mm or smaller (or those particles passing through a 140 mesh), or 0.07 mm or smaller (those particles passing through a 200 mesh), or 0.044 mm or smaller (those particles passing through a 325 mesh), or 0.037 mm or smaller (those particles passing through a 400 mesh).

In another embodiment, the particle sizes of rubber and the fossil fuels can be sufficiently matched to retain the stability of the slurry and avoid a coal/CE and plastic separation at high solids concentrations prior to entering the gasification zone in the gasifier. A feedstock stream that phase separates, whether between solids/liquid or CE and plastic/fossil fuel, can plug lines, created localized zones of gasified CE and plastic, create inconsistent ratios of fossil fuel/CE and plastic, and can impact the consistency of the syngas composition. Variables to consider for determining the optimal particle size of the ground CE and plastics include the bulk density of the ground coal, the concentration of all solids in the slurry if a slurry is used, the effectiveness of any additives employed such as surfactants/stabilizers/viscosity modifiers, and the velocity and turbulence of the feedstock stream to the gasifier and through the injector nozzles.

In one embodiment or in any of the mentioned embodiments, the bulk density of the ground CE and plastics without compaction (loose) after final grinding is within 150%, or within 110%, or within 100%, or within 75%, or within 60%, or within 55%, or within 50%, or within 45%, or within 40%, or within 35% of the loose bulk density of the ground fossil fuel after its final grinding. For example, if the granulated coal has a loose bulk density of 40 lbs./ft3 and the granulated CE and plastics have a loose bulk density of 33 lbs./ft3, the bulk density of the CE and plastics would be within 21% of the ground coal. For measurement purposes, the bulk density of the pre-ground CE and plastics and the fossil fuel after final grinding is determined dry (without addition of water) even though they are ultimately used as a slurry.

In an alternative embodiment or in addition to any other embodiment described herein, the maximum particle size of the ground CE and plastics is selected to be similar (below or above) to the maximum particle size of the ground coal. The maximum particle size of the ground CE and plastics is desirably within (meaning below or above) 50%, or within 45%, or within 40%, or within 35%, or within 30%, or within 25%, or within 20%, or within 15%, or within 10%, or within 5% of the maximum particle size of the ground coal. The maximum particle size is not determined as the maximum size of the particle distribution but rather by sieving through meshes. The maximum particle size is determined as the first mesh which allows at least 90 volume % of a sample of the ground particles to pass. For example, if less than 90 volume % of a sample passes through a 300 mesh, then a 100 mesh, a 50 mesh, a 30 mesh, a 16 mesh, but succeeds at a 14 mesh, then the maximum particle size of that sample is deemed to correspond to the first mesh size that allowed at least 90 volume % to pass through, and in this case, a 14 mesh corresponding to a maximum particle size of 1.4 mm.

The amount of ground CE and plastics present in the feedstock stream can be up to 25 wt. %, or up to 20 wt. %, or up 15 wt. %, or up to 12 wt. %, or up to 10 wt. %, or up to 7 wt. %, or up to 5 wt. %, or less than 5 wt. % or range from 0.1 wt. % to 25 wt. %, or 0.1 wt. % to 20 wt. %, or from 0.1 wt. % to 15 wt. %, or from 0.1 wt. % to 12 wt. %, or from 0.1 wt. % to 10 wt. %, or from 0.1 wt. % to 7 wt. %, desirably from 0.1 wt. % up to or less than 5 wt. %, based on the weight of all solids. Since CE and plastics have, on average, a much lower fixed carbon content than solid fossil fuels, the amount of carbon dioxide they generate will be more than that of the solid fossil fuels at the same residence time in the gasification zone and on the same weight basis. Desirably, the concentration of the pre-ground CE and plastics is low to obtain the advantage of minimizing an increase of carbon dioxide content over that generated by the solid fossil fuels alone. Desirably the concentration of pre-ground CE and plastics is less than 5 wt. %, or not more than 4.5 wt. %, or not more than 4 wt. %, or not more than 3.5 wt. %, or not more than 3 wt. %, or not more than 2.5 wt. %, or not more than 2 wt. %, and in each case as least 0.1 wt %, or at least 0.5 wt. %, or at least 1 wt. %, each based on the weight of the solids in the feedstock stream. Examples of the content of ground CE and plastic present in the feedstock stream include 0.25 wt. % to less than 5 wt. %, or from 0.25 wt. % to 4 wt. %, or from 0.25 wt. % to 3 wt. %, or from 0.25 wt. % to 2.5 wt. %, or from 0.5 wt. % to 5 wt. %, or from 0.5 wt. % to 4 wt. %, or from 0.5 wt. % to 3 wt. %, or from 0.5 wt. % to 2.5 wt. %, or from 1 wt. % to 5 wt. %, or from 1 wt. % to 4 wt. %, or from 1 wt. % to 3 wt. %, or from 1 wt. % to 2.5 wt. % each based on the weight of the solids in the feedstock stream.

The pre-ground CE and plastics are desirably isolated as a ground CE and plastic feed for ultimate destination to be mixed with one or more components of the feedstock stream. In one embodiment or in any of the mentioned embodiments, at least 80 wt. %, or at least 85 wt. %, or at least 90 wt. %, or at least 95 wt. %, or at least 96 wt. %, or at least 97 wt. %, or at least 98 wt. %, or at least 99 wt. %, or at least 99.5 wt. %, or 100 wt. % of all solid feedstock other than solid fossil fuels in the feedstock stream fed into the gasifier is pre-ground CE and plastics.

The solids in the feedstock stream desirably do not contain sewage sludge, waste paper, or biomass. In one embodiment or in any of the mentioned embodiments, the feedstock stream contains not more than 10 wt. %, or not more than 6 wt. %, or not more than 5 wt. %, or not more than 4 wt. %, or not more than 3 wt. %, or not more than 2 wt. %, or not more than 1 wt. %, or not more than 0.5 wt. %, or not more than 0.25 wt. %, or not more than 0.1 wt. % of any one of sewage sludge, waste paper, biomass, or a combination of two or more, each based on the weight of the solids in the feedstock stream.

The pre-ground CE and plastics will, even after final grinding, contain some level of materials other polymer, such as metals, fillers, and other materials. The quantity of such materials in the pre-ground CE and plastics that feed into the feedstock stream, other than rubber, is desirably less than 8 wt. %, or not more than 6 wt. %, or not more than 5 wt. %, or not more than 4 wt. %, or not more than 3.5 wt. %, or not more than 2 wt. %, or not more than 1.5 wt. %, or not more than 1 wt. %, or not more than 0.75 wt. %, or not more than 0.5 wt. %, based on the weight of the pre-ground CE and plastic particles.

The amount of solid fossil fuel, such as coal, in the feedstock or fed to the gasifier can be at least 10 wt. %, or at least 80 wt. %, or at least 85 wt. %, or at least 90 wt. %, or at least 93 wt. %, or at least 95 wt. %, or at least 97 wt. %, or at least 98 wt. %, or at least 98.5 wt. %, or at least 99 wt. %, and less than 100 wt. %, or less than 99.5 wt. %, based on the weight of solids in the feedstock.

Coal contains a quantity of ash that also contains elements other than carbon, oxygen, and hydrogen. The quantity of elements other than carbon, hydrogen, oxygen, and sulfur in the feedstock stream is desirably not more than 9 wt. %, or not more than 8.5 wt. %, or not more than 8 wt. %, or not more than 7.5 wt. %, or not more than 7 wt. %, or not more than 7.5 wt. %, or not more than 7 wt. %, or not more than 6.5 wt. %, or not more than 6 wt. %, or not more than 5.5 wt. %, or not more than 5 wt. %, or not more than 4.5 wt. %, based on the weight of all dry solids in the feedstock stream, or alternatively based on the weight of the feedstock stream.

Coal contains a quantity of ash that also contains elements other than carbon, oxygen, and hydrogen. The quantity of elements other than carbon, hydrogen, and oxygen in the solids in the feedstock stream is desirably not more than 15 wt. %, or not more than 12 wt. %, or not more than 10 wt. %, or not more than 9 wt. %, or not more than 8.5 wt. %, or not more than 8 wt. %, or not more than 7.5 wt. %, or not more than 7 wt. %, or not more than 7.5 wt. %, or not more than 7 wt. %, or not more than 6.5 wt. %, or not more than 6 wt. %, or not more than 5.5 wt. %, or not more than 5 wt. %, or not more than 4.5 wt. %, based on the weight of all dry solids in the feedstock stream, or alternatively based on the weight of the feedstock stream.

The caloric heat value of CE and plastics is desirably similar to or better than that of coal. For example, the CE and plastics have a heat value of at least 13,000, or at least 13,500, or at least 14,000 BTU/lb., or in the range of 13,000 to 15,000 BTU/lb. (30 MJ/Kg-35 MJ/Kg), while bituminous coal can have a heat value in a range of 12,500 to 13,300 BTU/lb. (29-31 MJ/Kg). Further, any ash or non-organic material will be melted and vitrified into the ash or slag matrix that is produced from the inorganics in the coal. Therefore, the CE and plastics can be viewed as a direct replacement for coal in the feed process.

The concentration of solids (e.g. fossil fuel and CE and plastics) in the feedstock stream should not exceed the stability limits of the slurry, or the ability to pump or feed the feedstock at the target solids concentration to the gasifier. Desirably, the solids content of the slurry should be at least 50 wt. %, or at least 55 wt. %, or at least 60 wt. %, or at least 62 wt. %, or at least 65 wt. %, or at least 68 wt. %, or at least 69 wt. %, or at least 70 wt. %, or at least 75 wt. %, the remainder being a liquid phase that can include water and liquid additives. The upper limit is not particularly limited because it is dependent upon the gasifier design. However, given the practical pumpability limits of a solid fossil fuels feed and maintaining a homogeneous distribution of solids in the slurry, the solids content for a solid fossil slurry fed slagging gasifier desirably should not exceed 75 wt. %, or 73 wt. %, the remainder being a liquid phase that can include water and liquid additives (as noted above, gases are not included in the calculation of weight percentages).

The feedstock stream is desirably stable at 5 minutes, or even 10 minutes, or even 15 minutes, or even 20 minutes, or even ½ hour, or even 1 hour, or even two hours. A feedstock slurry is deemed stable if its initial viscosity is 100,000 cP or less. The initial viscosity can be obtained by the following method. A 500-600 g of a well-mixed sample is allowed to stand still in a 600 mL liter glass beaker at ambient conditions (e.g. 25° C. and about 1 atm). A Brookfield R/S Rheometer equipped with V80-40 vane operating at a shear rate of 1.83/s is submerged into the slurry to the bottom of the beaker after the slurry is well mixed (e.g. a homogeneous distribution of solids was formed). After a designated period of time, a viscosity reading is obtained at the start of rotation, which is the initial viscosity reading. The slurry is considered to be stable if the initial reading on starting a viscosity measurement is not more than 100,000 cP at the designated period of time. Alternatively, the same procedure can be used with a Brookfield viscometer with an LV-2 spindle rotating at a rate of 0.5 rpm. Since different viscosity value will be obtained using the different equipment, the type of equipment used should be reported. However, regardless of the differences, the slurry is considered stable under either method only if its viscosity is not more than 100,000 cP at the reported time.

The quantity of solids in the feedstock stream and their particle size are adjusted to maximize the solids content while maintaining a stable and pumpable slurry. A pumpable slurry is one which has a viscosity under 30,000 cP, or not more than 25,000 cP, or not more than 23,000 cP, and desirably not more than 20,000 cP, or not more than 18,000 cP, or not more than 15,000 cP, or not more than 13,000 cP, in each case at ambient conditions (e.g. 25° C. and 1 atm). At higher viscosities, the slurry becomes too thick to practically pump. The viscosity measurement to determine the pumpability of the slurry is taken by mixing a sample of the slurry until a homogeneous distribution of particles is obtained, thereafter immediately submerging a Brookfield viscometer with an LV-2 spindle rotating at a rate of 0.5 rpm into the well mixed slurry and taking a reading without delay. Alternatively, a Brookfield R/S rheometer with V80-40 vane spindle operating at a shear rate of 1.83/s can be used. The method of measurement is reported since the measured values between the two rheometers at their difference shear rates will generate different values. However, the cP values stated above apply to either of the rheometer devices and procedures.

Conventional CE and plastics granulators can be used to obtain the desired particle size. These can include systems for shredding the CE and plastics using high capacity shredders to chips, followed by granulation and if necessary, a fine/powder granulator can be used in a last step. For the last step, the fine/powder granulators can be in communication with a conveying system to transport the granulated CE and plastics to a storage vessel from which the granulated CE and plastics can be fed to any location for making the feedstock stream, or the granulated particles can be fed continuously from the fine granulator to the desired location for making the feedstock stream. The feed of granulated CE and plastic particles from a storage vessel can be in a batch mode or in a continuous mode.

The carbonaceous materials, e.g. fossil fuel and CE and plastics, are advantageously loose and not densified by mechanical or chemical means after final granulation to make the pre-ground CE and plastics (other than natural compaction that may result from storage under its own weight), or desirably at any time prior to making pre-ground CE and plastics and after their post-industrial manufacture or post-consumer use. For example, coal chunks are granulated in the presence of water and not thereafter compacted, and CE and plastics are fine ground/pulverized without densification operations prior to their addition into water.

The solid fossil fuels, such as coal, must be ground prior to feeding into a gasifier to achieve an acceptable particle size for the reasons noted above. These same considerations apply to the CE and plastic granulates, although as noted above, since the coal grinding equipment is not suitable to grind CE and plastics, the CE and plastics must be pre-ground prior to combining them to the feedstock composition or before adding to the coal grinding equipment.

The coal is typically ground to a size of 2 mm or less, and can be ground to any of the sizes noted above with respect to the granulated CE and plastic particle sizes. The small size of the coal and CE and plastic particles is important to assure a uniform suspension in the liquid vehicle which will not settle out, to allow sufficient motion relative to the gaseous reactants, to assure substantially complete gasification, and to provide pumpable slurries of high solids content with a minimum of grinding.

The quality of the coal employed is not limited. Anthracite, bituminous, sub-bituminous, brown coal, and lignite coal can be sources of coal feedstock. To increase the thermal efficiency of the reactor, the coal employed desirably has a carbon content that exceeds 35 wt. %, or at least 42 wt. %, based on the weight of the coal. Accordingly, bituminous or anthracite coal is desirable due to their higher energy content.

Sulfur is also typically present in solid fossil fuels. Desirably, the content of sulfur is less than 5 wt. %, not more than 4 wt. %, or not more than 3 wt. %, or not more than 2.5 wt. %, and also can contain a measure of sulfur, such as at least 0.25 wt. %, or at least 0.5 wt. %, or at least 0.75 wt. %.

It is also desirable to employ coal with a low inherent moisture content to improve the thermal efficiency of the gasifier. Using coal having moisture contents less than 25 wt. % or less than 20 wt. % or less than 15 wt. % or not more than 10 wt. % or not more than 8 wt. % without the application of external artificially applied heat is desirable.

Desirably, the coal feedstock has a heat value of at least 11,000 BTU/lb., or at least 11,500 BTU/lb., or at least 12,500 BTU/lb., or at least 13,000 BTU/lb., or at least 13,500 BTU/lb., or at least 14,000 BTU/lb., or at least 14,250 BTU/lb., or at least 14,500 BTU/lb.

While it is possible that the feedstock stream may contain minor amounts of liquid hydrocarbon oils leached from CE and plastics or coal, the feedstock stream desirably contains less than 5 wt. %, or not more than 3 wt. %, or not more than 1 wt. %, or not more than 0.1 wt. % liquid (at ambient conditions) non-oxygenated hydrocarbon petroleum oils introduced as such into the feedstock stream. Desirably, the feedstock stream contains less than 2 wt. %, or not more than 1 wt. %, or no added liquid fraction from refining crude oil or reforming any such fraction. Desirably, the quantity of liquids in the feedstock stream is other than the solids content. The content of liquids, or the content of water, present in the feedstock stream is desirably not more than 50 wt. %, or not more than 35 wt. %, or not more than 32 wt. %, or not more than 31 wt. %, or not more than 30 wt. %, based on the weight of the feedstock stream. Desirably, in each case, the content of liquids or water in the feedstock stream is desirably at least 10 wt. %, or at least 15 wt. %, or at least 20 wt. %, or at least 25 wt. %, or at least 27 wt. %, or at least 30 wt. %, based on the weight of the feedstock stream. Desirably, the liquids present in the feedstock stream contain at least 95 wt. % water, or at least 96 wt. % water, or at least 97 wt. % water, or at least 98 wt. % water, or at least 99 wt. % water, based on the weight of all liquids fed to the gasifier. In another embodiment, other than chemical additives that are chemically synthesized and contain oxygen or sulfur or nitrogen atoms, the liquid content of the feedstock stream is at least 96 wt. % water, or at least 97 wt. % water, or at least 98 wt. % water, or at least 99 wt. % water, based on the weight of all liquids fed to the gasifier.

In an embodiment, the water present in the feedstock stream is not waste water, or in other words, the water fed to the solids to make the feedstock stream is not waste water. Desirably, the water employed has not been industrially discharged from any process for synthesizing chemicals, or it not municipal waste water. The water is desirably fresh water, or potable water.

The feedstock stream comprises at least a solid fossil fuel such as ground coal, and ground CE and plastics, which can be size reduced by any method. Desirably, the feedstock stream also comprises water. The amount of water in the feedstock stream can range from 0 wt. % up to 50 wt. %, or from 10 wt. % to 40 wt. %, or from 20 wt. % to 35 wt. %. The feedstock stream is desirably a slurry containing water.

In addition to coal, water, and CE and plastics, other additives can be added to and contained in the feedstock stream, such as viscosity modifiers and pH modifiers. The total quantity of additives can range from 0.01 wt. % to 5 wt. %, or from 0.05 wt. % to 5 wt. %, or from 0.05 to 3 wt. %, or from 0.5 to 2.5 wt. %, based on the weight of the feedstock stream. The quantity of any individual additive can also be within these stated ranges.

The viscosity modifiers (which includes surfactants) can improve the solids concentration in the slurry. Examples of viscosity modifiers include:

(i) alkyl-substituted amine-based surfactant such as alkyl-substituted aminobutyric acid, alkyl-substituted polyethoxylated amide, and alkyl-substituted polyethoxylated quaternary ammonium salt; and (ii) sulfates such as salts of organic sulfonic acids including ammonium, calcium and sodium sulfonates, particularly those with lignin and sulfo-alkylated lignites;

(iii) phosphate salts;

(iv) polyoxyalkylene anionic or nonionic surfactants.

More specific examples of alkyl-substituted aminobutyric acid surfactants include N-coco-beta-aminobutyric acid, N-tallow-beta-aminobutyric acid, N-lauryl-beta-aminobutyric acid, and N-oleyl-beta-aminobutyric acid. N-coco-beta-aminobutyric acid.

More specific examples of alkyl-substituted polyethoxylated amide surfactant include polyoxyethylene oleamide, polyoxyethylene tallowamide, polyoxyethylene laurylamide, and polyoxyethylene cocoamide, with 5-50 polyoxyethylene moieties being present.

More specific examples of the alkyl-substituted polyethoxylated quaternary ammonium salt surfactant include methylbis (2-hydroxyethyl) cocoammonium chloride, methylpolyoxyethylene cocoammonium chloride, methylbis (2-hydroxyethyl) oleylammonium chloride, methylpolyoxyethylene oleylammonium chloride, methylbis (2-hydroxyethyl) octadecylammonium chloride, and methylpolyoxyethylene octadecylammonium chloride.

More specific examples of sulfonates include sulfonated formaldehyde condensates, naphthalene sulfonate formaldehyde condensates, benzene sulfonate-phenol-formaldehyde condensates, and lingosulfonates.

More specific examples of phosphate salts include trisodium phosphate, potassium phosphate, ammonium phosphate, sodium tripolyphosphate or potassium tripolyphosphate.

Examples of polyoxyalkylene anionic or nonionic surfactants have 1 or more repeating units derived from ethylene oxide or propylene oxide, or 1-200 oxyalkylene units.

Desirably, the surfactant is an anionic surfactant, such as salts of an organic sulfonic acid. Examples are calcium, sodium and ammonium salts of organic sulfonic acids such as 2,6-dihydroxy naphthalene sulfonic acid, lignite sulfonic acid, and ammonium lignosulfonate.

Examples of pH modifiers include aqueous alkali metal and alkaline earth hydroxides such as sodium hydroxide, and ammonium compounds such as 20-50 wt. % aqueous ammonium hydroxide solutions. The aqueous ammonium hydroxide solution can be added directly to the feedstock composition prior to entry into the gasifier, such as in the coal grinding equipment or any downstream vessels containing the slurry.

The atomic ratio of total oxygen to carbon entering the gasification zone can be a value in the range of 0.70 to less than 2, or from 0.9 to 1.9, or from 0.9 to 1.8, or from 0.9 to 1.5, or from 0.9 to 1.4, or from 0.9 to 1.2, or from 1 to 1.9, or from 1 to 1.8, or from 1 to 1.5, or from 1 to 1.2, or from 1.05 to 1.9, or from 1.05 to 1.8, or from 1.05 to 1.5, or from 1.05 to 1.2. The atomic ratio of free oxygen to carbon entering the gasification zone can also be within these same values. The weight ratio of both total oxygen and free oxygen to carbon in pounds entering the gasification zone can also each be within these stated values.

The total carbon content in the feedstock stream is at least 40 wt. %, or at least 45 wt. %, or at least 50 wt. %, or at least 55 wt. %, or at least 60 wt. %, or at least 65 wt. %, and desirably at least 70 wt. %, or at least 75 wt. %, or at least 80 wt. %, or at least 85 wt. %, or at least 90 wt. %, each based on the total solids content.

The feedstock stream is desirably injected along with an oxidizer into the refractory-lined combustion chamber of the synthesis gas generating gasifier. The feedstock stream (desirably a slurry) and oxidizer are desirably sprayed through an injector into a gasification zone that is under significant pressure, typically about 500 psig or more, or 600 psig or more, or 800 psig or more, or 1000 psig or more. The velocity or flow rate of the feedstock and oxidizer streams ejected from the injector nozzle into the combustion chamber will exceed the rate of flame propagation to avoid backflash.

In one embodiment or in any of the mentioned embodiments, of the invention, advantageously only one feedstock stream is charged to the gasifier or gasification zone, or in other words, all sources of carbon fuel are fed to the gasifier in only one stream. In another embodiment, only one feedstock stream is necessary or employed to produce a syngas or product stream that is a raw material to synthesize a chemical compound.

In another embodiment, a chemical is made from a first syngas sourced from a first gasifier fed with a first feedstock stream containing coal and the first syngas stream is not combined with a second syngas sourced from any other gasifier fed with second feedstock stream where the coal content between the first and second feedstock streams differs by more than 20%, or more than 10%, or more than 5%. For example, a first syngas stream generated from a first feedstock stream containing 90 wt. % coal would not be combined with a syngas stream generated from a different gasifier fed with a feedstock stream containing 70 wt. % coal or no coal, but could be combined with one containing 72 wt. % coal or more.

Prior to entry into the gasifier, the feedstock stream may be subjected to a variety of other optional processes. For example, the coal-rubber slurry can flow through a thickener in which excess water is eliminated from the slurry to obtain the final desired solids concentration of the slurry entering into the gasifier vessel. Additionally, the feedstock stream may be pre-heated to prior to entry into the gasifier. In this embodiment, the feedstock stream is heated to a temperature below the boiling point of water at the operating pressure existing in reaction zone. The preheater, when employed, reduces the heat load on the gasifier and improves the efficiency of utilization of both fuel and oxygen. In this embodiment, all of the water required for the generation of synthesis gas in reaction zone is supplied in liquid phase. When petroleum coke is employed as fuel for the gas generator, part of the water, e.g., from 1 to about 90 percent by weight based on the weight of water, may be vaporized in the slurry feed preheater or combined with the oxidizing stream as vaporized water.

The oxidizer is desirably an oxidizing gas that can include air, and desirably is a gas enriched in oxygen at quantities greater than that found in air. The reaction of oxygen and solid fossil fuel is exothermic. Desirably, the oxidant gas contains at least 25 mole % oxygen, or at least 35 mole %, or at least 40 mole %, or at least 50 mol %, or at least 70 mole %, or at least 85 mole %, or at least 90 mole %, or at least 95 mole %, or at least 97 mole %, or at least 98 mole % oxygen, or at least 99 mole %, or at least 99.5 mole % based on all moles in the oxidant gas stream injected into the reaction (combustion) zone of the gasifier. In another embodiment, the combined concentration of oxygen in all gases supplied to the gasification zone is also in the above stated amount. The particular amount of oxygen as supplied to the reaction zone is desirably sufficient to obtain near or maximum yields of carbon monoxide and hydrogen obtained from the gasification reaction relative to the components in the feedstock stream, considering the amount relative to the feedstock stream, and the amount of feedstock charged, the process conditions, and the reactor design.

In one embodiment or in any of the mentioned embodiments, steam is not supplied to the gasification zone. The amount of water in a slurry fed system is typically more than sufficient a co-reactant and heat sink to regulate the gasification temperature. The addition of stream in a slurry fed gasifier will generally unduly withdraw heat from the reaction zone and reduce its efficiency.

Other reducible oxygen-containing gases may be supplied to the reaction zone, for example, carbon dioxide, nitrogen, or simply air. In one embodiment or in any of the mentioned embodiments, no gas stream enriched in carbon dioxide or nitrogen (e.g. greater than the molar quantity found in air, or greater than 2 mole %, or greater than 5 mole %, or greater than 10 mole %, or greater than 40 mole %) is charged into the gasifier. Many of these gases serve as carrier gases to propel a dry feed to a gasification zone. Due to the pressure within the gasification zone, these carrier gases are compressed to provide the motive force for introduction into the gasification zone. The expenditure of energy and equipment for compressing carrier gases to the feedstock stream is avoided is a slurry feed. Accordingly, in another embodiment, the feedstock stream containing at least pre-ground CE and plastics and ground solid fossil fuel flowing to the gasifier, or this feedstock stream introduced to a injector or charge pipe, or this feedstock stream introduced into the gasification zone, or a combination of all the above, does not contain gases compressed in equipment for gas compression. Alternatively, or in addition, other than the oxygen rich stream described above, no gas compressed in equipment for gas compression is fed to the gasification zone or even to the gasifier. It is noteworthy that high pressure charge pumps that process the slurry feed for introduction into the gasification zone are not considered gas compressing equipment.

Desirably, no gas stream containing more than 0.03 mole %, or more than 0.02 mole %, or more than 0.01 mole % carbon dioxide is charged to the gasifier or gasification zone. In another embodiment, no gas stream containing more than 77 mole %, or more than 70 mole %, or more than 50 mole %, or more than 30 mole %, or more than 10 mole %, or more than 5 mole %, or more than 3 mole % nitrogen is charged to the gasifier or gasification zone. In another embodiment, steam is not charged into the gasification zone or to the gasifier. In yet another embodiment, a gaseous hydrogen stream (e.g. one containing more than 0.1 mole % hydrogen, or more than 0.5 mole %, or more than 1 mole %, or more than 5 mole %) is not charged to the gasifier or to the gasification zone. In another embodiment, a stream of methane gas (e.g. one containing more than 0.1 mole % methane, or more than 0.5 mole %, or more than 1 mole %, or more than 5 mole % methane) is not charged to the gasifier or to the gasification zone. In another embodiment, the only gaseous stream introduced to the gasification zone is an oxygen rich gas stream as described above.

The gasification process desirably employed is a partial oxidation gasification reaction. To enhance the production of hydrogen and carbon monoxide, the oxidation process involves partial, rather than complete, oxidization of the fossil fuel and CE and plastics and therefore is desirably operated in an oxygen-lean environment, relative to the amount needed to completely oxidize 100% of the carbon and hydrogen bonds. The total oxygen requirements for the gasifier is desirably at least 5%, or at least 10%, or at least 15%, or at least 20%, in excess of the amount theoretically required to convert the carbon content of the solid fuel and CE and plastics to carbon monoxide. In general, satisfactory operation may be obtained with a total oxygen supply of 10 to 80 percent in excess of the theoretical requirements. An example of a suitable amount of oxygen per pound of carbon is in the range of 0.4 to about 3.0 pound free oxygen per pound of carbon, or from 0.6 to 2.5, or from 0.9 to 2.5, or from 1 to 2.5, or from 1.1 to 2.5, or from 1.2 to 2.5 pounds of free oxygen per pound of carbon.

Mixing of the feedstock stream and the oxidant is desirably accomplished entirely within the reaction zone by introducing the separate streams of feedstock and oxidant so that they impinge upon each other within the reaction zone. Desirably, the oxidant stream is introduced into the reaction zone of the gasifier as high velocity to both exceed the rate of flame propagation and to improve mixing with the feedstock stream. The oxidant is desirably injected into the gasification zone in the range of 25 to 500 feet per second, or 50 to 400 ft/s, or 100 to 400 ft/s. These values would be the velocity of the gaseous oxidizing stream at the injector-gasification zone interface, or the injector tip velocity.

Figures 3, 4:
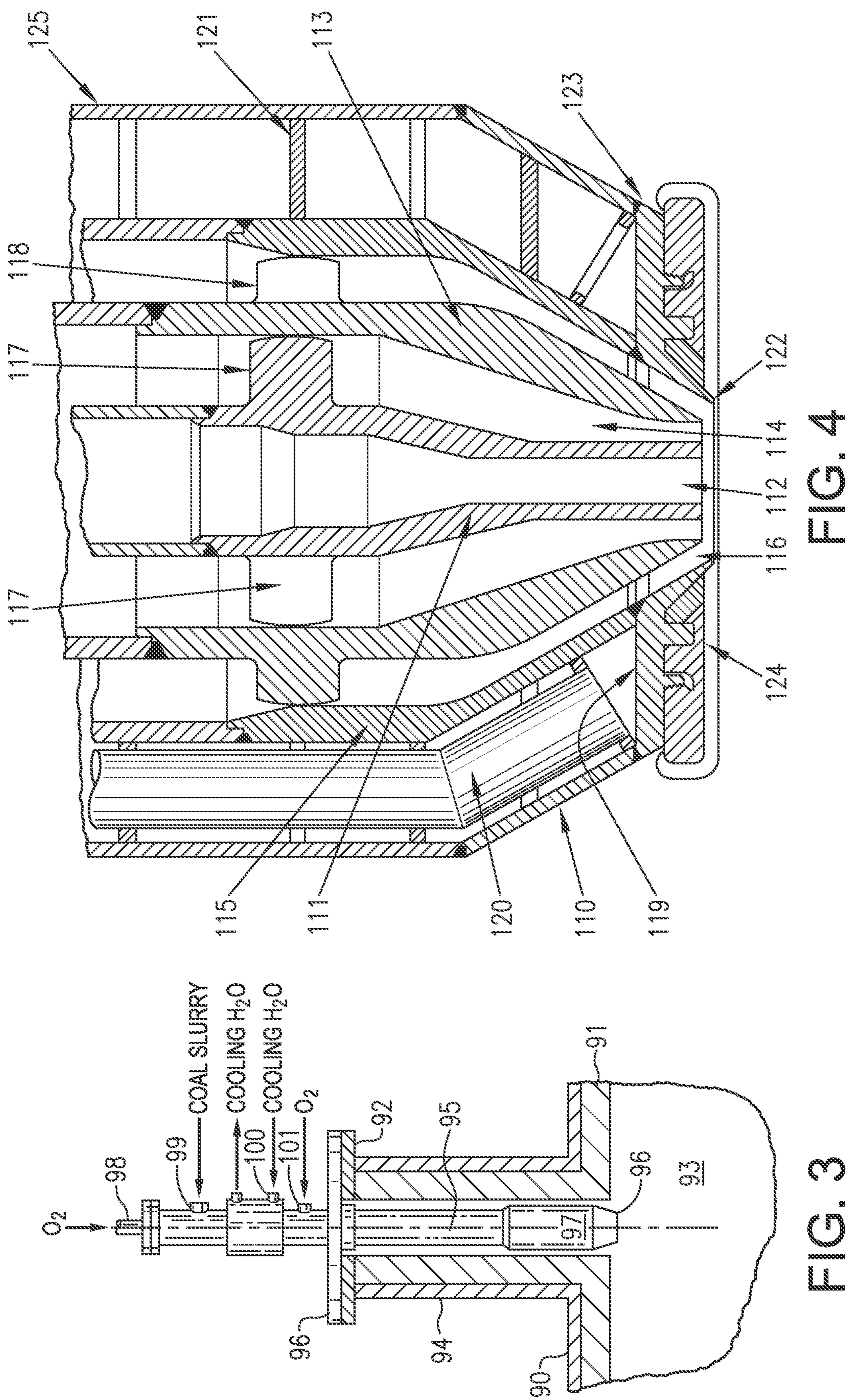
FIG. 3 is a cross section view of a gasifier injector.
FIG. 4 is a more detailed view of the nozzle section of a gasifier injector.

One method for increasing the velocity of the oxidant feed to the gasification zone is by reducing the diameter of the oxidant annulus near the tip of the injector or injector. Near the tip of the injector the annular passage converges inwardly in the shape of a hollow cone as shown in FIGS. 3 and 4. The oxidizing gas is thereby accelerated and discharged from the injector as a high velocity conical stream having an apex angle in the desirably range of about 30° to 45°. The streams from the injector converge at a point located about 0-6 inches beyond the injector face. The high velocity stream of oxidizing gas hits the relatively low velocity feedstock stream, atomizing it and forming a fine mist comprising minute particles of water and particulate solid carboniferous fuel highly dispersed in the oxidizing gas. The particles of solid carboniferous matter impinge against one another and are fragmented further.

The velocity of the feedstock slurry is determined by the desired throughput of syngas generation. Suitable examples of feedstock velocity introduced into gasification zone prior to contact with the oxidizing agent is in the range of 5 to 50 feet per second.

The feedstock stream and the oxidant can optionally be preheated to a temperature above about 200° C., or at least 300° C., or at least 400° C. Advantageously the gasification process employed does not require preheating the feedstock stream to efficiently gasifying the fuel, and a preheat treatment step would result in lowering the energy efficiency of the process. Desirably, the feedstock stream, and optionally the oxidant, are not preheated prior to their introduction into the gasifier. A preheat treatment step would be contacting the feedstock stream or oxidant with equipment that raises the temperature of the feedstock stream sufficiently such that the temperature of the feedstock stream or oxidant stream is above 200° C., or above 190° C., or above 170° C., or above 150° C., or above 130° C., or above 110° C., or above 100° C., or above 98° C., or above 90° C., or above 80° C., or above 70° C., or above 60° C., immediately prior to introduction into a injector on the gasifier. For example, while coal can be dried with hot air above 200° C., this step would not be considered a preheat of the feedstock stream if the feedstock stream is below 200° C. upon its introduction into the injector.

In another embodiment, no thermal energy (other than incidental heat from processing equipment such as mills, grinders or pumps) is applied to the feedstock stream containing both CE and plastics and the solid fossil fuel, or to the oxidant stream, at any point prior to its introduction into the injector, or gasifier, or gasification zone (other than the temperature increase experienced in a injector) that would increase the temperature of the stream by more than 180° C., or more than 170° C., or more than 160° C., or more than 150° C., or more than 140° C., or more than 130° C., or more than 120° C., or more than 110° C., or more than 100° C., or more than 90° C., or more than 80° C., or more than 70° C., or more than 60° C., or more than 50° C., or more than 40° C., or more than 30° C.

The process of the invention employs a gasification process, which is distinct from pyrolysis (which is a thermal process that degrades a fuel source in the absence of air or oxygen) or plasma processes in that gasification does not employ a plasma arc.

Desirably, the type of gasification technology employed is a partial oxidation entrained flow gasifier that generates syngas. This technology is distinct from fixed bed (alternatively called moving bed) gasifiers and from fluidized bed gasifiers. In fixed bed (or moving bed gasifiers), the feedstock stream moves in a countercurrent flow with the oxidant gas, and the oxidant gas typically employed is air. The feedstock stream falls into the gasification chamber, accumulates, and forms a bed of feedstock. Air (or alternatively oxygen) flows from the bottom of the gasifier up through the bed of feedstock material continuously while fresh feedstock continuously falls down from the top by gravity to refresh the bed as it is being combusted. The combustion temperatures are typically below the fusion temperature of the ash and are non-slagging. Whether the fixed bed operated in countercurrent flow or in some instances in co-current flow, the fixed bed reaction process generates high amount of tars, oils, and methane produced by pyrolysis of the feedstock in the bed, thereby both contaminating the syngas produced and the gasifier. The contaminated syngas requires significant effort and cost to remove tarry residues that would condense once the syngas is cooled, and because of this, such syngas streams are generally not used to make chemicals and is instead used in direct heating applications. In a fluidized bed, the feedstock material in the gasification zone is fluidized by action of the oxidant flowing through the bed at a high enough velocity to fluidize the particles in the bed. In a fluidized bed, the homogeneous reaction temperatures and low reaction temperatures in the gasification zone also promotes the production of high amounts of unreacted feedstock material and low carbon conversion, and operating temperatures in the fluidized bed are typically between 800-1000° C. Further, in a fluidized bed it is important to operate below slagging conditions to maintain the fluidization of the feedstock particles which would otherwise stick to the slag and agglomerate. By employing an entrained flow gasification, these deficiencies present with fixed (or moving bed) and fluidized bed gasifiers that are typically used to process waste materials is overcome.

In one embodiment or in any of the mentioned embodiments, the feedstock stream is introduced at the top ⅛ section of the gasifier, desirably at the top 1/12 of the gasifier height defined by the gasifier shell (not including the injector height protruding from the top of the shell or pipes protruding from the bottom of the shell). The feedstock stream is desirably not introduced into a side wall of the gasifier. In another embodiment, the feedstock stream is not a tangential feed injector.

In another embodiment, oxidant is introduced at the top ⅛ section of the gasifier, desirably at the top 1/12 of the gasifier height defined by the gasifier shell. The oxidant is desirably not introduced into the side wall of the gasifier or bottom of the gasifier. In another embodiment, both the feedstock stream and oxidant are introduced at the top ⅛ section of the gasifier, desirably at the top 1/12 of the gasifier height defined by the gasifier shell. Desirably, the oxidant and feedstock stream are fed co-currently to ensure good mixing. In this regard, a co-current feed means that the axis of the feedstock and oxidant streams are substantially parallel (e.g. not more than a 25° deviation, or not more than a 20°, or not more than a 15°, or not more than a 10°, or not more than a 8°, or not more than a 6°, or not more than a 4°, or not more than a 2°, or not more than a 1° deviation from each other) and in the same direction.

The feedstock and oxidant streams are desirably introduced into the gasification zone through one or more injector nozzles. Desirably, the gasifier is equipped with at least one of the injector nozzles in which through that injector nozzle both a feedstock stream and an oxidant stream are introduced into the gasification zone.

While the feedstock stream can be a dry feed or a slurry feed, the feedstock stream is desirably a slurry. The syngas produced in the gasification process is desirably used at least in part for making chemicals. Many synthesis processes for making chemicals are at high pressure, and to avoid energy input into pressurizing the syngas stream, desirably the gasifier is also run at high pressure, particularly when the syngas stream is directly or indirectly in gaseous communication with a vessel in which a chemical is synthesized. Dry feeds to a gasifier operating at high pressure are specially treated to ensure that the feed can be effectively blown and injected into the high-pressure gasification zone. Some techniques include entraining a flow of nitrogen at high pressure and velocity, which tends to dilute the syngas stream and reduce the concentration of desirably components such as carbon monoxide and hydrogen. Other carrier or motive gases include carbon monoxide, but like nitrogen, these gases are compressed before feeding into or compressed with the solid fossil fuels, adding to the energy requirements and capital cost of feed lock hoppers and/or compressing equipment. To deal with these issues, many dry feed gasifiers will operate at lower pressures, which for the mere production of electricity is sufficient, but is undesirable for gasifiers producing a syngas stream for making chemicals. With a slurry feed, a motive gas is not necessary and can readily be fed to a high-pressure gasifier that produces syngas as high pressure, which is desirable for making chemicals. In one embodiment or in any of the mentioned embodiments, the feedstock stream is not processed through a lock hopper prior to entering an injector or entering the gasification zone. In another embodiment, the feedstock composition containing ground CE and plastics and solid fossil fuel is not pressurized in a lock hopper.

Desirably, the gasifier is non-catalytic, meaning that gasifier does not contain a catalyst bed, and desirably the gasification process is non-catalytic, meaning that a catalyst is not introduced into the gasification zone as a discrete unbound catalyst (as opposed to captive metals in the CE and plastics or solid fossil fuel that can incidentally have catalytic activity). The gasification process in the reaction zone is desirably conducted in the absence of added catalysts and contains no catalyst bed. The gasification process is also desirably a slagging gasification process; that is, operated under slagging conditions (well above the fusion temperature of ash) such that a molten slag is formed in the gasification zone and runs along and down the refractory walls.

In another embodiment, the gasifier is not designed to contain a pyrolysis zone. Desirably, the gasifier is not designed to contain a combustion zone. Most preferably, the gasifier is designed to not contain, or does not contain, either a combustion zone or a pyrolysis zone. The pyrolysis zone incompletely consumes the fuel source leading to potentially high amounts of ash, char, and tarry products. A combustion zone, while absent in tars, produces high amounts of CO2 and lower amounts of the more desirably carbon monoxide and hydrogen. Desirably, the gasifier is a single stage reactor, meaning that there is only one zone for conversion of the carbon in the feedstock to gases within the gasifier shell.

The gasification zone is void or empty space defined by walls in which oxidation reactions occur and allow gases to form within the space. Desirably, gasification zone does not have a bath of molten material or molten material that accumulates at the bottom of the gasification zone to form a bath. The gasification zone is desirably not enclosed on the bottom but rather is in gaseous communication with other zones below the gasification zone. Slag, while molten, does not accumulate at the bottom of the gasification zone but rather runs down the sides of the refractory and into a zone below the gasification zone, such as a quench zone to solidify the slag.

The flow of hot raw syngas in the gasifier desirably is vertically downward, or a down-flow reactor. Desirably, the flow of syngas generated in the gasifier is downward from the highest point of injecting the feedstock stream, desirably from the point of all feedstock stream locations. In another embodiment, the location for withdrawing the syngas stream from the gasifier is lower that at least one location for introducing the feedstock stream, desirably lower than all locations for introducing a feedstock stream.

The gasifier desirably contains refractory lining in the gasification zone. While a steam generating membrane or jacket between the gasifier wall and the surfaces facing the gasification zone can be employed, desirably the gasifier does not contain a membrane wall, or a steam generating membrane, or a steam jacket in the gasification zone or between inner surfaces facing the gasification zone and the gasifier shell walls as this removes heat from the gasification zone. Desirably, the gasification zone is lined with refractory, and optionally there is no air or steam or water jacket between the refractory lining the gasification zone (or optionally in any reaction zone such as combustion or pyrolysis) and the outer shell of the gasifier.

The gasification process is desirably a continuous process meaning that the gasifier operates in a continuous mode. The inclusion of pre-granulated CE and plastics into the feedstock stream can be intermittent or continuous provided that a continuous feed of fossil fuel is fed to the gasifier since the gasification process in the gasifier is in a continuous mode. By a continuous mode for gasifier operation is meant that the gasification process is continuous for at least 1 month, or at least 6 months, or at least 1 year. Desirably, the inclusion of granulated CE and plastics in the feedstock stream is continuous for at least 1 day, or at least 3 days, or at least 14 days, or at least 1 month, or at least 6 months, or at least 1 year. A process is deemed continuous despite shut-downs due to maintenance or repair.

The feedstock can be fed into the gasification zone through one or more injectors. In one embodiment or in any of the mentioned embodiments, the gasifier contains only one injector. In another embodiment, the gasifier contains only one location for introducing feedstock. Typically, the injector nozzle serving the gasification chamber is configured to have the feedstock stream concentrically surround the oxidizer gas stream along the axial core of the nozzle. Optionally, the oxidizer gas stream can also surround the feedstock stream annulus as a larger, substantially concentric annulus. Radially surrounding an outer wall of the outer oxidizer gas channel can be an annular cooling water jacket terminated with a substantially flat end-face heat sink aligned in a plane substantially perpendicular to the nozzle discharge axis. Cool water is conducted from outside the combustion chamber into direct contact with the backside of the heat sink end-face for conductive heat extraction.

The reaction between the hydrocarbon and oxygen should take place entirely outside the injector proper to prevent localized concentration of combustible mixtures at or near the surfaces of the injector elements.

The gasification zone, and optionally all reaction zones in the gasifier are operated at a temperature in the range of at least 1000° C., or at least 1100° C., or at least 1200° C., or at least 1250° C., or at least 1300° C., and up to about 2500° C., or up to 2000° C., or up to 1800° C., or up to 1600° C., each of which are well above the fusion temperature of ash and are desirably operated to form a molten slag in the reaction zone. In one embodiment or in any of the mentioned embodiments, the reaction temperature is desirably autogenous. Advantageously, the gasifier operating in steady state mode is at an autogenous temperature and does not require application of external energy sources to heat the gasification zone.

In one embodiment or in any of the mentioned embodiments, the gasifier does not contain a zone within the gasifier shell to dry feedstock such as the coal, pet-coke, or CE and plastics prior to gasification. The increase in temperature within the injector is not considered a zone for drying.

Desirably, the gasification zone is not under negative pressure during operations, but rather is under positive pressure during operation. The gasification zone is desirably not equipped with any aspirator or other device to create a negative pressure under steady state operation.

The gasifier is operated at a pressure within the gasification zone (or combustion chamber) of at least 200 psig (1.38 MPa), or at least 300 psig (2.06 MPa), or at least 350 psig (2.41 MPa), and desirably at least 400 psig (2.76 MPa), or at least 420 psig (2.89 MPa), or at least 450 psig (3.10 MPa), or at least 475 psig (3.27 MPa), or at least 500 psig (3.44 MPa), or at least 550 psig (3.79 MPa), or at least 600 psig (4.13 MPa), or at least 650 psig (4.48 MPa), or at least 700 psig (4.82 MPa), or at least 750 psig (5.17 MPa), or at least 800 psig (5.51 MPa), or at least 900 psig (6.2 MPa), or at least 1000 psig (6.89 MPa), or at least 1100 psig (7.58 MPa), or at least 1200 psig (8.2 MPa). The particular operating pressure on the high end is regulated with a variety of considerations, including operating efficiency, the operating pressures needed in chemical synthesis reactors particularly with integrated plants, and process chemistry. Suitable operating pressures in the gasification zone on the high end need not exceed 1300 psig (8.96 MPa), or need not exceed 1250 psig (8.61 MPa), or need not exceed 1200 psig (8.27 MPa), or need not exceed 1150 psig (7.92 MPa), or need not exceed 1100 psig (7.58 MPa), or need not exceed 1050 psig (7.23 MPa), or need not exceed 1000 psig (6.89 MPa), or need not exceed 900 psig (6.2 MPa), or need not exceed 800 psig (5.51 MPa), or need not exceed 750 psig (5.17 MPa). Examples of suitable desirably ranges include 400 to 1000, or 425 to 900, or 450 to 900, or 475 to 900, or 500 to 900, or 550 to 900, or 600 to 900, or 650 to 900, or 400 to 800, or 425 to 800, or 450 to 800, or 475 to 800, or 500 to 800, or 550 to 800, or 600 to 800, or 650 to 800, or 400 to 750, or 425 to 750, or 450 to 750, or 475 to 750, or 500 to 750, or 550 to 750, each in psig.

Desirably, the average residence time of gases in the gasifier reactor is desirably very short to increase throughput. Since the gasifier is desirably operated at high temperature and pressure, substantially complete conversion of the feedstock to gases can occur in a very short time frame. The average residence time of the gases in the gasifier can be as short as less than 30 seconds, or not more than 25 seconds, or not more than 20 seconds, or not more than 15 seconds, or not more than 10 seconds, or not more than 7 seconds. Desirably, the average residence time of gases in all zones designed for conversion of feedstock material to gases is also quite short, e.g. less than 25 seconds, or not more than 15 seconds, or not more than 10 seconds, or not more than 7 seconds, or not more than 4 seconds. In these time frames, at least 85 wt. %, or at least or more than 90 wt. %, or at least 92 wt. %, or at least 94 wt. % of the solids in the feedstock can be converted to gases (substances which remain as a gas if the gas stream were cooled to 25° C. and 1 atm) and liquid (substances which are in liquid state if the gas stream is cooled to 25° C. and 1 atm such as water), or more than 93 wt. %, or more than 95 wt. %, or more than 96 wt. %, or more than 97 wt. %, or more than 98 wt. %, or more than 99 wt. %, or more than 99.5 wt. %.

A portion of ash and/or char in the gasifier can be entrained in the hot raw syngas stream leaving the gasification reaction zone. Ash particles in the raw syngas stream within the gasifier are particles which have not reached the melting temperature of the mineral matter in the solid fuel. Slag is substantially molten ash or molten ash which has solidified into glassy particles and remains within the gasifier. Slag is molten until quenched and then form beads of fused mineral matter. Char are porous particles that are devolatilized and partially combusted (incompletely converted) fuel particles. The particulate matter gathered in the bottom part of the reactor, or the quench zone, are predominately slag (e.g. above 80 wt. % slag) and the remainder is char and ash. Desirably, only trace amounts of tar or no tar is present in the gasifier, or in the quench zone, or in the gasification zone, or present in the hot raw syngas within the gasifier, or present in the raw syngas discharged from the gasifier (which can be determined by the amount of tar condensing from the syngas stream when cooled to a temperature below 50° C.). Trace amounts are less than 0.1 wt. % (or less than 0.05 wt. % or less than 0.01 wt. %) of solids present in the gasifier, or less than 0.05 volume %, or not more than 0.01 vol %, or not more than 0.005 vol %, or not more than 0.001 volume %, or not more than 0.0005 vol %, or not more than 0.0001 vol % in the raw syngas stream discharged from the gasifier.

In another embodiment, the process does not increase the amount of tar to a substantial extent relative to the same process except replacing the CE and plastics with the same amount and type of solid fossil fuel used in the mixed feedstock composition.

The quantity of tar generated in the process with the mixed feedstock is less than 10% higher, or less than 5% higher, or less than 3% higher, or less than 2% higher, or not higher at all, than the amount of tar generated with the same feedstock replacing the CE and plastics with the same solid fossil fuel under the same conditions.

To avoid fouling downstream equipment from the gasifier (scrubbers, CO/H2 shift reactors, acid gas removal, chemical synthesis), and the piping in-between, the syngas stream should have low or no tar content. The syngas stream as discharged from the gasifier desirably contains no or less than 4 wt. %, or less than 3 wt. %, or not more than 2 wt. %, or not more than 1 wt. %, or not more than 0.5 wt. %, or not more than 0.2 wt. %, or not more than 0.1 wt. %, or not more than 0.08 wt. %, or not more than 0.05 wt. %, or not more than 0.02 wt. %, or not more than 0.01 wt. %, or nor more than 0.005 wt. % tar, based on the weight of all condensable solids in the syngas stream. For purposes of measurement, condensable solids are those compounds and elements that condense at a temperature of 15° C./1 atm.

In another embodiment, the tar present, if at all, in the syngas stream discharged from the gasifier is less than 10 g/m3 of the syngas discharged, or not more than 9 g/m3, or not more than 8 g/m3, or not more than 7 g/m3, or not more than 6 g/m3, or not more than 5 g/m3, or not more than 4 g/m3, or not more than 3 g/m3, or not more than 2 g/m3, and desirably not more than 1 g/m3, or not more than 0.8 g/m3, or not more than 0.75 g/m3, or not more than 0.7 g/m3, or not more than 0.6 g/m3, or not more than 0.55 g/m3, or not more than 0.45 g/m3, or not more than 0.4 g/m3, or not more than 0.3 g/m3, or not more than 0.2 g/m3, or not more than 0.1 g/m3, or not more than 0.05 g/m3, or not more than 0.01 g/m3, or not more than 0.005 g/m3, or not more than 0.001 g/m3, or not more than 0.0005 g/m3, in each case Normal (15° C./1 atm). For purposes of measurement, the tars are those tars that would condense at a temperature of 15° C./1 atm, and includes primary, secondary and tertiary tars, and are aromatic organic compounds and other than ash, char, soot, or dust. Examples of tar products include naphthalenes, cresols, xylenols, anthracenes, phenanthrenes, phenols, benzene, toluene, pyridine, catechols, biphenyls, benzofurans, benzaldehydes, acenaphthylenes, fluorenes, naphthofurans, benzanthracenes, pyrenes, acephenanthrylenes, benzopyrenes, and other high molecular weight aromatic polynuclear compounds. The tar content can be determined by GC-MSD.

In another embodiment, the tar yield of the gasifier (combination of tar in syngas and tar in reactor bottoms and in or on the ash, char, and slag) is not more than 4 wt. %, or not more than 3 wt. %, or not more than 2.5 wt. %, or not more than 2.0 wt. %, or not more than 1.8 wt. %, or not more than 1.5 wt. %, or not more than 1.25 wt. %, or not more than 1 wt. %, or not more than 0.9 wt. %, or not more than 0.8 wt. %, or not more than 0.7 wt. %, or not more than 0.5 wt. %, or not more than 0.3 wt. %, or not more than 0.2 wt. %, or not more than 0.1 wt. %, or not more than 0.05 wt. %, or not more than 0.01 wt. %, or not more than 0.005 wt. %, or not more than 0.001 wt. %, or not more than 0.0005 wt. %, or not more than 0.0001 wt. %, based on the weight of solids in the feedstock stream fed to the gasification zone.

Because of the gasification technique employed along with the very small particle size of the CE and plastics, the amount of char generated by gasifying the CE and plastic-solid fossil fuel feedstock stream can remain within acceptable limits. For example, the amount of char (or incompletely converted carbon in the feedstock) generated by conversion of the carbon sources in the feedstock stream is not more than 15 wt. %, or not more than 12 wt. %, or not more than 10 wt. %, or not more than 8 wt. %, or not more than 5 wt. %, or not more than 4.5 wt. %, or not more than 4 wt. %, or not more than 3.5 wt. %, or not more than 3 wt. %, or not more than 2.8 wt. %, or not more than 2.5 wt. %, or not more than 2.3 wt. %, or not more than 4.5 wt. %, or not more than 4.5 wt. %, or not more than 4.5 wt. %.

In the process, char can be recycled back to the feedstock stream. In another embodiment, the efficiencies and features of the invention can be obtained without recycling char back to the gasification zone.

The total amount of char (or incompletely converted carbon in the feedstock) and slag generated in the gasifier or by the process is desirably not more than 20 wt. %, or not more than 17 wt. %, or not more than 15 wt. %, or not more than 13 wt. %, or not more than 10 wt. %, or not more than 9 wt. %, or not more than 8.9 wt. %, or not more than 8.5 wt. %, or not more than 8.3 wt. %, or not more than 8 wt. %, or not more than 7.9 wt. %, or not more than 7.5 wt. %, or not more than 7.3 wt. %, or not more than 7 wt. %, or not more than 6.9 wt. %, or not more than 6.5 wt. %, or not more than 6.3 wt. %, or not more than 6 wt. %, or not more than 5.9 wt. %, or not more than 5.5 wt. %, in each case based on the weight of the solids in the feedstock stream. In another embodiment, the same values apply with respect to the total amount of ash, slag, and char generated in the gasifier or by the process, based on the weight of the solids in the feedstock stream. In another embodiment, the same values apply with respect to the total amount of ash, slag, char and tar generated in the gasifier or by the process, based on the weight of the solids in the feedstock stream.

The raw syngas stream flows from the gasification zone to a quench zone at the bottom of the gasifier where the slag and raw syngas stream are cooled, generally to a temperature below 550° C., or below 500° C., or below 450° C. The quench zone contains water in a liquid state. The hot syngas from the gasification zone may be cooled by directly contacting the syngas stream with liquid water. The syngas stream can be bubbled through the pool of liquid water, or merely contact the surface of the water pool. In addition, the hot syngas stream may be cooled in a water jacketed chamber having a height that above the top surface of the water pool to allow the hot syngas to both contact the water pool and be cooled in the water jacketed chamber. Molten slag is solidified by the quench water and most of the ash, slag and char are transferred to the water in the quench tank. The partially cooled gas stream, having passed through the water in the quench zone, may be then discharged from the gasifier as a raw syngas stream and passed through a water scrubbing operation to remove any remaining entrained particulate matter.

The pressure in the quench zone is substantially the same as the pressure in the gasification zone located above the water level in the gasifier, and a portion of the quench water and solids at the bottom of the quench tank is removed by way of a lock hopper system. A stream of quench water carrying fine particles exits the gasifier quench zone in response to a liquid level controller and can be directed to a settler. The solids and water from the lock hopper may then flow into a water sump or settler where optionally the coarse particulate solids may be removed by screens or filter thereby producing a dispersion of fine particulate solids.

The raw gas stream discharged from the gasification vessel includes such gasses as hydrogen, carbon monoxide, carbon dioxide and can include other gases such as methane, hydrogen sulfide and nitrogen depending on the fuel source and reaction conditions. Carbon dioxide in the raw syngas stream discharged from the gasification vessel is desirably present in an amount of less than 20 mole %, or less than 18 mole %, or less than 15 mole %, or less than 13 mole %, or not more than 11 mole %, based on all moles of gases in the stream. Some nitrogen and argon can be present in the raw syngas stream depending upon the purity of the fuel and oxygen supplied to the process.

In one embodiment or in any of the mentioned embodiments, the raw syngas stream (the stream discharged from the gasifier and before any further treatment by way of scrubbing, shift, or acid gas removal) can have the following composition in mole % on a dry basis and based on the moles of all gases (elements or compounds in gaseous state at 25° C. and 1 atm) in the raw syngas stream:

a. H2: 15 to 60, or 18 to 50, or 18 to 45, or 18 to 40, or 23 to 40, or 25 to 40, or 23 to 38, or 29 to 40, or 31 to 40
b. CO: 20 to 75, or 20 to 65, or 30 to 70, or 35 to 68, or 40 to 68, or 40 to 60, or 35 to 55, or 40 to 52
c. CO2:1.0 to 30, or 2 to 25, or 2 to 21, or 10 to 25, or 10 to 20
d. H2O: 2.0 to 40.0, or 5 to 35, or 5 to 30, or 10 to 30
e. CH4: 0.0 to 30, or 0.01 to 15, or 0.01 to 10, or 0.01 to 8, or 0.01 to 7, or 0.01 to 5, or 0.01 to 3, or 0.1 to 1.5, or 0.1 to 1
f. H2S: 0.01 to 2.0, or 0.05 to 1.5, or 0.1 to 1, or 0.1 to 0.5
g. COS: 0.05 to 1.0, or 0.05 to 0.7, or 0.05 to 0.3
h. Total sulfur: 0.015 to 3.0, or 0.02 to 2, or 0.05 to 1.5, or 0.1 to 1
i. N2: 0.0 to 5, or 0.005 to 3, or 0.01 to 2, or 0.005 to 1, or 0.005 to 0.5, or 0.005 to 0.3

The gas components can be determined by FID-GC and TCD-GC or any other method recognized for analyzing the components of a gas stream.

The molar hydrogen/carbon monoxide ratio is desirably at least 0.65, or at least 0.68, or at least 0.7, or at least 0.73, or at least 0.75, or at least 0.78, or at least 0.8, or at least 0.85, or at least 0.88, or at least 0.9, or at least 0.93, or at least 0.95, or at least 0.98, or at least 1.

The total amount of hydrogen and carbon monoxide relative to the total amount of syngas discharged from the gasifier on a dry basis is high, on the order of greater than 70 mole %, or at least 73 mole %, or at least 75 mole %, or at least 77 mole %, or at least 79 mole %, or at least 80 mole %, based on the syngas discharged.

In another embodiment, the dry syngas production expressed as gas volume discharged from the gasifier per kg of solid fuel (e.g. CE and plastics and coal) charged to all locations on the gasifier is at least 1.7, or at least 1.75, or at least 1.8, or at least 1.85, or at least 1.87, or at least 1.9, or at least 1.95, or at least 1.97, or at least 2.0, in each case as N m3 gas/kg solids fed The carbon conversion efficiency in one pass is good and can be calculated according to the following formula:

$$= \frac{\text{total carbon in feed} - \text{total carbon in char and tar}}{\text{total carbon in feed}} \times 100$$

The carbon conversion efficiency in the process in one pass can be at least 70%, or at least 73%, or at least 75%, or at least 77%, or at least 80%, or at least 82%, or at least 85%, or at least 88%, or at least 90%, or at least 93%.

In another embodiment, the raw syngas stream contains particulate solids in an amount of greater than 0 wt. % up to 30 wt. %, or greater than 0 wt. % up to 10 wt. %, or greater than 0 wt. % up to 5 wt. %, or greater than 0 wt. % up to 1 wt. %, or greater than 0 wt. % up to 0.5 wt. %, or greater than 0 wt. % up to 0.3 wt. %, or greater than 0 wt. % up to 0.2 wt. %, or greater than 0 wt. % up to 0.1 wt. %, or greater than 0 wt. % up to 0.05 wt. %, each based on the weight of solids in the feedstock stream. The amount of particulate solids in this case is determined by cooling the syngas stream to a temperature of below 200° C., such as would occur in a scrubbing operation.

The cold gas efficiency of the process using the mixed CE and plastic/solid fossil fuel as a percent can be calculated as:

$$= \frac{\text{Produced gas (mole)} \times HHV(MJ \text{ per mole})}{\text{Feedstock (kg)} \times HHV(MJ \text{ per kg})} \times 100$$

The cold gas efficiency is at least 60%, or at least 65%, or at least 66%, or at least 67%, or at least 68%, or at least 69%, or desirably at least 70%, or at least 71%, or at least 72%, or at least 73%, or at least 74%, or at least 75%, or at least 76%, or at least 77%, or at least 78%, or at least 79%.

In one embodiment or in any of the mentioned embodiments, hydrogen and carbon monoxide from the raw syngas stream discharged from the gasifier or from a scrubbed or purified syngas stream are not recycled or recirculated back to a gasification zone in a gasifier. Desirably, carbon dioxide from the raw syngas stream discharged from the gasifier or from a scrubbed or purified syngas stream is not recycled or recirculated back to a gasification zone in a gasifier. Desirably, no portion of the syngas stream discharged from the gasifier or from a scrubbed or purified syngas stream is recycled or recirculated back to a gasification zone in a gasifier. In another embodiment, no portion of the syngas discharged from the gasifier is used to heat the gasifier. Desirably, no portion of the syngas made in the gasifier is burned to dry the solid fossil fuel.

The feedstock stream is gasified with the oxidizer such as oxygen desirably in an entrained flow reaction zone under conditions sufficient to generate a molten slag and ash. The molten slag and ash are separated from the syngas and quench cooled and solidified. In a partial oxidation reactor, the coal/CE and plastic/water mixture is injected with oxygen and the coal/rubber will react with oxygen to generate a variety of gases, including carbon monoxide and hydrogen (syngas). The molten slag and unreacted carbon/CE and plastics accumulate into a pool of water in the quench zone at the bottom part of the reactor to cool and solidify these residues.

In one embodiment or in any of the mentioned embodiments, the slag discharged from the gasifier as a solid. Slag is cooled and solidified within the gasifier in a quench zone within the shell of the gasifier, and is discharged from the gasifier shell as a solid. The same applies to ash and char. These solids discharged from the gasifier are accumulated into a lock hopper which can then be emptied. The lock hopper is generally isolated from the gasifier and the quench zone within the gasifier.

The process can be practiced on an industrial scale and on a scale sufficient to provide syngas as a raw material to make chemicals on an industrial scale. At least 300 tons/day, or at least 500 t/d, or at least 750 t/d, or at least 850 t/d, or at least 1000 t/d, or at least 1250 t/d, and desirably at least 1500 t/d, or at least 1750 t/d, or even at least 2000 t/d of solids can be fed to the gasifier. The gasifier is desirably not designed to be mobile and is fixed to the ground, and desirably stationary during operations.

The syngas compositional variability produced by gasifying the feedstock containing the solid fossil fuel and CE and plastics is quite low over time. In one embodiment or in any of the mentioned embodiments, the compositional variability of the syngas stream is low during a time period when the feedstock stream contains the solid fossil fuel and the pre-ground CE and plastics. The compositional variability of the syngas stream can be determined by taking at least 6 measurements of the concentration of the relevant gaseous compound in moles in equal time sub-periods across the entire time that the feedstock solids content are consistent and contain CE and plastics, such entire time not to exceed 12 days. The mean concentration of the gaseous compound is determined over the 6 measurements. The absolute value of the difference between the number farthest away from the mean and the mean number is determined and divided into the mean number×100 to obtain a percent compositional variability.

The compositional variability of any one of:

a. CO amount, or
b. H2 amount, or
c. CO2 amount, or
d. CH4 amount, or
e. H2S amount, or
f. COS amount, or
g. H2+CO amount, or its molar ratio in sequence (e.g. H2:CO ratio), or
h. H2+CO+CO2 amount, or its molar ratio in sequence, or
i. H2+CO+CH4 amount, or its molar ratio in sequence, or
j. H2+CO+CO2+CH4 amount, or its molar ratio in sequence, or
k. H2S+COS amount, or its molar ratio in sequence, or
l. $H_2+CO+CO_2+CH_4+H_2S+COS$, can be not more than 5%, or not more than 4%, or not more than 3%, or not more than 2%, or not more than 1%, or not more than 0.5%, or not more than 0.25% during the shorter of a 12-day period or the time that CE and plastics are present in the feedstock composition.

In another embodiment, variability of the syngas stream generated by the mixed feedstock containing CE and plastics ("mixed case") is compared to the benchmark variability of the syngas stream generated from the same feedstock without the CE and plastics and its amount replaced by a corresponding amount of the same fossil fuel ("solid fossil fuel only case") and processed under the same conditions to obtain a % switching variability, or in other words, the syngas variability generated by switching between the two feedstock compositions. The variation of the mixed case can be less than, or no different than, or if higher can be similar to the variation of the solid fossil fuel only case. The time periods to determine variations is set by the shorter of a 12-day period or the time that CE and plastics are present in the feedstock composition, and that time period is the same time period used for taking measurements in the solid fossil fuels only case. The measurements for the solid fossil fuels only case are taken within 1 month before feeding a feedstock containing CE and plastics to the gasifier or after the expiration of feeding a feedstock containing CE and plastics to the gasifier. The variations in syngas composition made by each of the streams is measured according to the procedures stated above. The syngas mixed case variability is less than, or the same as, or not more than 15%, or not more than 10%, or not more than 5%, or not more than 4%, or not more than 3%, or not more than 2%, or not more than 1%, or not more than 0.5%, or not more than 0.25% of the syngas solid fossil fuel only case. This can be calculated as:

$$\% \ SV = \frac{V_m - V_{ff}}{V_{ff}} \times 100$$

where % SW is percent syngas switching variability on one or more measured ingredients in the syngas composition; and $V_m$ is the syngas compositional variability using the mixed stream containing CE and plastics and the fossil fuel; and $V_{ff}$ is the syngas compositional variability using the fossil fuel only stream, where the solids concentration is the same in both cases, the fossil fuel is the same in both cases, and the feedstocks are gasified under the same conditions, other than temperature fluctuations which may autogeneously differ as a result of having CE and plastics in the feedstock, and the variabilities are with respect to any one or more of the syngas compounds identified above. In the event that the % SV is negative, then the syngas mixed case variability is less than the syngas solid fossil fuel only case.

In another embodiment, the ratio of carbon monoxide/hydrogen generated from a stream of CE and plastics and solid fossil fuel (mixed stream) is similar to the carbon monoxide/hydrogen ratio generated from the same stream replacing the CE and plastics content with the same solid fossil fuel (ff only stream). The carbon monoxide/hydrogen ratio between the mixed stream and ff only stream can be within 10%, or within 8%, or within 6%, or within 5%, or within 4%, or within 3%, or within 2%, or within 1.5%, or within 1%, or within 0.5% of each other. The percentage similarity can be calculated by taking the absolute value of the differences in CO/H2 ratios between the mixed and ff only streams and dividing that number into the CO/H2 ratio of the ff only stream ×100.

In another embodiment, the amount of CO2 generated from a stream of CE and plastics and solid fossil fuel (mixed stream) is similar to the amount of carbon dioxide generated from a ff only stream. The process of the invention can be conducted such that the amount of CO2 generated from a stream of CE and plastics and solid fossil fuel (mixed stream) is no more than 25%, or no more than 20%, or no more than 15%, or no more than 13%, or no more than 10%, or no more than 8%, or no more than 7%, or no more than 6%, or no more than 5%, or no more than 4%, or no more than 3%, or no more than 2%, or no more than 1%, or no more than 0.75%, or no more than 0.5%, or nor more than 0.25%, or no more than 0.15%, or no more than 0.1% of the amount of carbon dioxide generated from a ff only stream (e.g. coal). The percentage similarity can be calculated by subtracting the amount of CO2 generated in a syngas stream using the mixed stream from the amount of CO2 generated in a syngas stream using the ff only stream, and dividing that number by the CO2 generated in a syngas stream using the ff only stream ×100.

In another embodiment, there is provided a continuous process for feeding a gasifier with a continuous feedstock composition containing solid fossil fuel and intermittently feeding a feedstock composition containing CE and plastics and solid fossil fuel, while maintaining a negative, zero, or minimal syngas compositional switching variability over time frames that includes feedstocks with and without the CE and plastics using syngas produced using feedstocks without the CE and plastics as the benchmark. For example, switching frequency between feedstocks without the CE and plastics (FF only) and the identical feedstocks except replacing a portion of the solids with the CE and plastics (Mixed) can be at least 52×/yr, or at least 48×/yr, or at least 36×/yr, or at least 24×/yr, or at least 12×/yr, or at least 6×/yr, or at least 4×/yr, or at least 2×/yr, or at least 1×/yr, or at least 1×/2 yr, and up to 3×/2 yr, without incurring a syngas switching variability beyond the percentages express above. One switch is counted as the number of times in a period that the Mixed feedstock is used.

To illustrate an example of the overall process, reference made to FIG. 1. Coal is fed through line 1 into a coal grinding zone 2 wherein it is mixed with a water from stream 3 and ground to the desired particle size. A suitable coal grinding process includes a shearing process. Examples of a suitable apparatus include ball mill, a rod mill, hammer mill, a raymond mill, or an ultrasonic mill; desirably a rod mill. The rod mill is desirably the wet grind type to prepare a slurry. A rod mill contains a number of rods within a cylinder where the rods rotate about a horizontal or near horizontal axis. The coal is ground when it is caught between the rods and cylinder wall by the rolling/rotating action of the rods. The rod mill can be the overflow type, end peripheral discharge, and center peripheral discharge, desirably the overflow type.

The grinder can also be equipped with a classifier to remove particles above the target maximum particle size. An example of a classifier is a vibrating sieve or a weir spiral classifier.

The coal grinder zone (which includes at least the grinding equipment, feed mechanisms to the grinder, and any classifiers) is a convenient location for combining preground CE and plastic particles through line 4 to the coal. The desired amount of coal and CE and plastics can be combined onto a weigh belt or separately fed though their dedicated weigh belts that feed the grinding apparatus. The water slurry of ground coal and CE and plastics is discharged through line 5 and pumped into a storage/charge tank 6 that is desirably agitated to retain a uniform slurry suspension. Alternatively, or in addition to the grinder 2 location, pre-ground CE and plastics can be added into the charge/storage tank 6 through line 7, particularly when this tank is agitated.

The feedstock stream is discharged from tank 6 directly or indirectly to the gasifier 9 through line 8 into the injector 10 in which the coal/rubber/water slurry is co-injected with an oxygen-rich gas from line 11 into the gasification reaction zone 12 where combustion takes place. The injector 10 may optionally be cooled with a water line 13 feeding a jacket on the injector and discharged through line 14. After start-up and in a steady state, the reaction in the reaction zone 12 takes place spontaneously at an autogenous temperature in the ranges noted above, e.g. 1200° C. to 1600° C. and at a pressure in the ranges note above, e.g. 10-100 atmospheres. The gaseous reaction products of the partial oxidation reaction include carbon monoxide, hydrogen, with lesser amounts of carbon dioxide and hydrogen sulfide. Molten ash, unconverted coal or rubber, and slag may also be present in the reaction zone 12.

Figure 2:
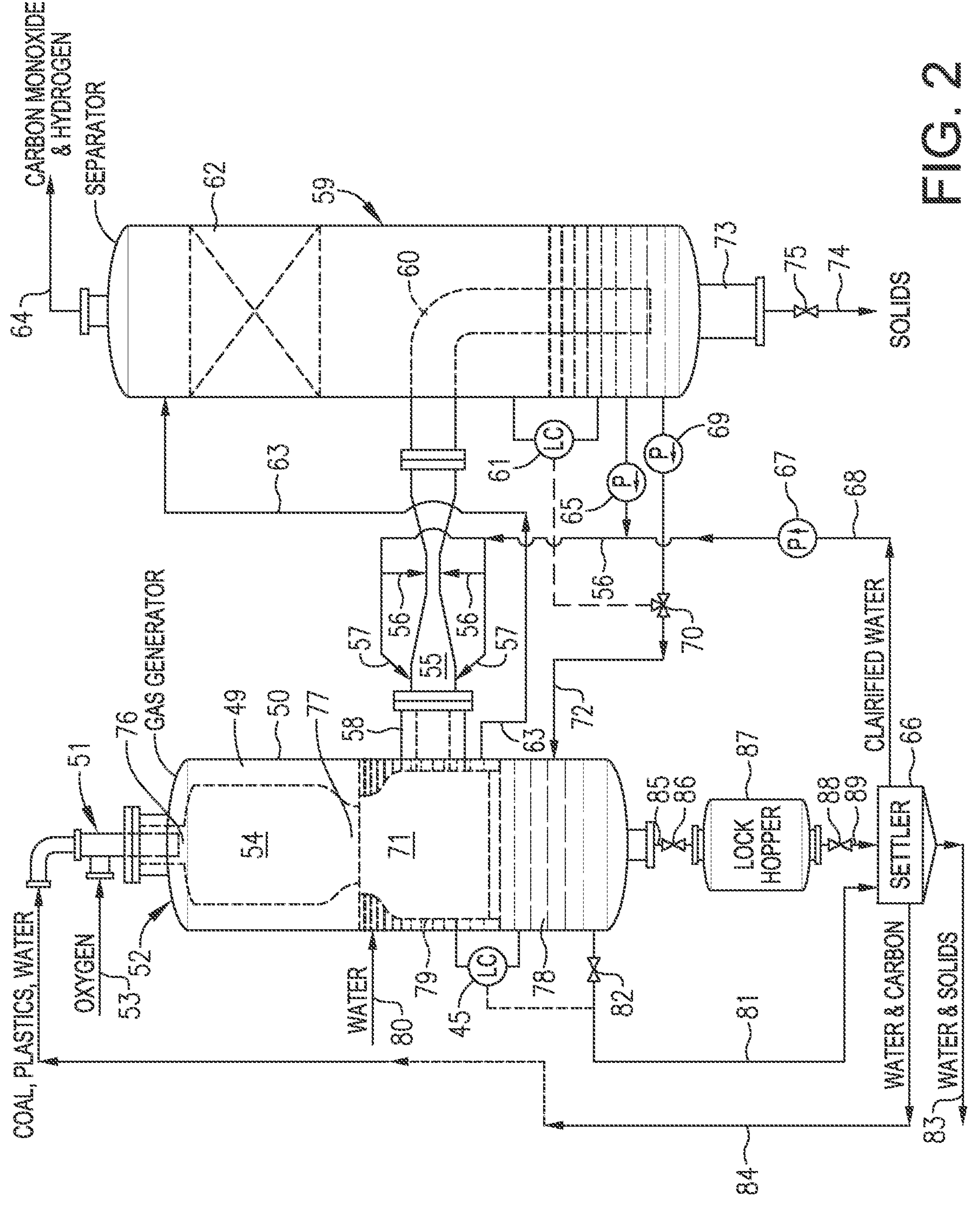
FIG. 2 is another example of a plant design for gasifying a feedstock of CE/plastics and solid fossil fuel to produce a syngas stream that is scrubbed.

The gasifier 9 is illustrated in more detail in FIG. 2, also as shown in U.S. Pat. No. 3,544,291, the entire disclosure of which is incorporated herein by reference. The gasifier comprises a cylindrical pressure vessel 50 with a refractory lining 75 defining a cylindrical, compact, unpacked reaction zone 54. The mixture of coal, CE and plastics, water and oxygen is injected through an injector axially into the upper end of reaction zone 54 through inlet passageway 76. Products of reaction are discharged axially from the lower end of reaction zone 54 through an outlet passageway 77 into a slag quench chamber 71. The quench chamber 71 and the reaction zone 54 are within the outer shell 50 of the gasifier and are in continuous gaseous and fluid communication with each other during the combustion and reaction in reaction zone 54. A pool of water 78 is maintained in the lower portion of quench chamber 71 and a water jacket 79 is provided in the upper portion of the quench chamber 71 to protect the pressure vessel shell from becoming overheated by hot gases from the gasification zone 54. Unconverted solid fuel and molten slag and ash from the solid fuel is discharged with the product gas stream through outlet 77 into the quench chamber 71 where the larger particles of solid and any molten ash or slag drops into the pool of water. The partially cooled gas is discharged from the quench chamber 71 through line 58, which optionally is also provided with a refractory lining 75.

Turning back to FIG. 1, the hot reaction product gas from reaction zone 12 along with the slag formed on the surfaces of refractory facing the reaction zone 12 are discharged into the quench chamber 15 where they are quickly cooled and solidified below the reaction temperature in zone 12 to form solid slag, ash, and unconverted coal which separates from the hot raw syngas to form a raw syngas stream which is discharged from the gasifier vessel. The process effectuates a separation of ash, slag, and unconverted products from the reaction product gases, and has the advantage over a fixed or moving bed waste gasifier in that within the gasifier vessel, a first step of purification of the gaseous reaction products from the reaction zone 12 has occurred prior to discharging the raw syngas stream from the gasification vessel. At the same time that the slag and vaporized unconverted fossil fuel elements are solidified in the quench water in quench zone 15, and part of the quench water is vaporized producing steam which is useful in subsequent operations, for example, for the water-gas shift reaction of the scrubbed raw syngas stream in which hydrogen is produced by reaction of carbon monoxide with water vapor in the presence of a suitable catalyst such as an iron oxide-chromic oxide catalyst.

The temperature of the raw syngas stream exiting the gasification vessel through line 16 can be within a range of 150° C. to 700° C., or from 175° C. to 500° C. Desirably, the temperature of the raw syngas discharged from the gasifier is not more than 500° C., or less than 400° C., or not more than 390° C., or not more than 375° C., or not more than 350° C., or not more than 325° C., or not more than 310° C., or not more than 300° C., or not more than 295° C., or not more than 280° C., or not more than 270° C. The temperature of the raw syngas exiting the gasification vessel is substantially reduced from the temperature of the reaction product gases within the reaction zone. The temperature reduction between the gasification zone gas temperature (or alternatively all reaction zones if more than one stage is used) and the raw syngas temperature discharged from the gasifier vessel can be at least 300° C., or at least 400° C., or at least 450° C., or at least 500° C., or at least 550° C., or at least 600° C., or at least 650° C., or at least 700° C., or at least 800° C., or at least 900° C., or at least 1000° C., or at least 1050° C., or at least 1100° C.

As shown in FIG. 1, the raw syngas is discharged from the gasifier through line 16 to a suitable scrubber 17 where it is contacted with water from line 18 for the removal of remaining solid particles from the raw syngas stream. Gas scrubber 17 may comprise a venturi scrubber, a plate type scrubber or a packed column, or a combination thereof, in which raw syngas stream is intimately contacted with water to effect the removal of solid particles from the raw syngas stream. The scrubbed raw syngas stream is discharged through line 19 for further use in other processes, such as acid gas (e.g. sulfur compounds) removal processes to make the resulting purified syngas stream suitable for manufacture of chemicals. Suitable process for acid gas removal include the Rectisol™ and Selexol™ acid gas removal processes. Once the sulfur species are removed from the syngas stream, elemental sulfur can be recovered and converted to sulfuric acid and other sulfur products that can be commercialized through processes such as the Claus™ process.

As shown in FIG. 1, the solids-water mixture from gas scrubber 17 is discharged from the scrubber passed through line 20 optionally to line 21 where it is mixed with quench water containing solids drawn from quench zone 15 via line 22 and the mixture passed through pressure reducing valve 23 into settling tank 24. A heat exchanger 25 serves to heat by heat exchange with hot quench water from line 22 the relatively cool make-up and recycle water supplied through line 26 from a suitable source and pumped to lines for quenching and/or scrubbing the product gas from the gas generator.

Solids, including unconverted particulate coal, settle by gravity from the water in settling tank 24 and are drawn off through line 27 as a concentrated slurry of ash, unconverted coal and soot in water. This slurry may be optionally be recycled to grinding zone 2 via line 28. If desired, a portion of the slurry from line 27 may be diverted through line 29 into mix tank 6 to adjust the concentration of solids in the water-coal-rubber slurry feedstream charged to the gasifier. Also, as shown in FIG. 2, water and solids from settler tank 66 may be drawn off in line 83 for processing, while water and ash, unconverted coal and soot may be drawn off the settle tank 66 through line 84 and combined with the feedstock of coal, CE and plastics and water.

As shown in FIG. 1, gases released in settler 24 may be discharged through line 30 and recovered as potential fuel gases. Clarified water from settler 24 is withdrawn through line 31 and recirculated to the quench water system through line 32. A portion of the water from line 32, after passing through heat exchanger 25, is supplied to the quench zone 15 through line 33 and a further portion of the water is passed through line 18 to gas scrubber 17. Further, water from the quench zone can be withdrawn through line 22 to settler 24 through a control valve 23. The water level can be controlled through a liquid level controller on the gasifier to maintain a substantially constant water level in quench zone.

Alternatively, or in addition, the quench water through line 33 feeding the quench water zone can supplied from a syngas scrubber downstream from the gasifier as shown in FIG. 2. The quench water stream optionally also fed to the quench zone may be clarified or may contain from about 0.1 weight % soot to about 1.5 weight % soot based on the weight of the quench water stream feeding the gasifier.

If desired, high temperature surfactants can be added to the quench water directly into the quench zone/chamber. Examples of such surfactants include any one of the surfactants mentioned above to stabilize the feedstock stream, such as ammonium lignosulfonate or an equivalent surfactant which is thermally stable at temperatures of about 300° F. to about 600° F. Other surfactants include organic phosphates, sulfonates and amine surfactants. The surfactants are used to establish a stable suspension of soot in the water at the bottom of the quench chamber, where the soot concentration can be at least 1 wt. %, or in the range of about 3.0 weight % to about 15.0 weight %, each based on the weight of the water in the quench chamber. The concentration of active surfactants in the bottom of the quench zone can vary from about 0.01 weight % to about 0.30 weight %.

Also, as illustrated in FIG. 2, an internal water jacket 79 is provided within the pressure vessel shell 50 at the upper portion of the quench zone 71. Water jacket 79 prevents overheating of the pressure vessel shell below the level of refractory 75 surrounding reaction zone 54. Water is introduced into water jacket 79 from line 80 and discharged therefrom through line 81 through valve 82 and can be fed directly or indirectly (through a settler tank 66) to a scrubber 59.

As shown in FIG. 1, periodically slag and other heavy incombustible solids settling to the bottom of quench zone 15 are withdrawn as a water-solids slurry through line 34 and valve 35 into lock hopper 36. Accumulated solid material from lock hopper 36 is discharged through line 37 as controlled by valve 38. In the operation of the lock hopper, valve 35 is opened and valve 38 closed during the filling period in which solid material from quench chamber 15 is transferred to lock hopper 36. Valve 35 is then closed and the lock hopper 36 emptied through line 37 by opening valve 38. From lock hopper 36, solid residue and water are discharged through line 37. The equivalent equipment and lines are shown in FIG. 2 as outlet 85, valves 86 and 88, line 89, and lock hopper 87.

In an alternative embodiment as shown in FIG. 1, fresh water can be charged to the lock hopper 36 to displace the sour water in the lock hopper 36. Cold clean water from line 39 is introduced through valve 40 into the lower part of lock hopper 36. Valve 41 in line 42 is opened to establish communication between line 33 and lock hopper 36. As the cold clean water enters the lower part of lock hopper 36, hot sour water is displaced from the lock hopper and flows through line 42 and line 33 into the quench zone 15 as part of the make-up water for the quench system. After the sour water has been displaced from lock hopper 36 valves 40 and 41 are closed and valve 38 opened to permit discharge of slag and clean water from the lock hopper through line 37.

In an alternate embodiment, as shown in FIG. 1, stripping gas such as carbon dioxide, or gases produced by the gasifier from which acid gases have been removed by chemical treatment, can be introduced into the lower portion of lock hopper 36 through line 43 after the lock hopper has been charged with slag and sour water from the quench zone 15 and valve 35 closed. Stripping gas under pressure is introduced into the lower portion of lock hopper 36 by opening valve 44 in line 43. At the same time, valve 41 in line 42 is opened allowing gas to pass through lines 42 and 33 into the quench zone 15. The stripping gas from line 43 desorbs sour gases, i.e. sulfides, cyanides, and other noxious gases, from the water in lock hopper 36. When the desorbed gases are introduced back into the gasifier, they mix with hot product gases and, after passing through the quench zone are discharged through line 16 to gas scrubber 17 as a part of the product gas stream for further purification and utilization.

To illustrate one embodiment of an injector, reference is made to FIG. 3, showing a partial cut-away view of a synthesis gas gasifier at the injector location. The gasifier vessel includes a structural shell 90 and an internal refractory liner 91 (or multiple liners) around an enclosed gasification zone 93. Projecting outwardly from the shell wall is an injector mounting neck 94 for supporting an elongated fuel injection injector assembly 95 within the gasifier vessel. The injector assembly 95 is aligned and positioned so that the face 96 of the injector nozzle 97 is substantially flush with the inner surface of the refractory liner 91. An injector mounting flange 96 secures the injector assembly 95 to a mounting neck flange 97 of the gasifier vessel to prevent the injector assembly 95 from becoming ejected during operation. A feed of oxygen flows into a central inner nozzle through conduit 98. The feedstock stream is fed to the injector assembly through line 99 into an annular space around the central oxidant nozzle. A cooling jacket surrounding the injector assembly 95 above the injector mounting flange 96 is fed with cooling water 100 to prevent the injector assembly from overheating. An optional second feed of oxidant flows through line 101 into an annular space around at least a portion of the outer surface of the shell defining the feedstock annulus.

A more detailed view of the injector is shown in FIG. 4. A sectional view of a portion of the injector assembly 80 toward the injector nozzle tip is illustrated. The injector assembly 80 includes an injector nozzle assembly 125 comprising three concentric nozzle shells and an outer cooling water jacket 110. The inner nozzle shell 111 discharges from an axial bore opening 112 the oxidizer gas that is delivered along upper assembly axis conduit 98 in FIG. 3. Intermediate nozzle shell 113 guides the feedstock stream into the gasification zone 93. As a fluidized solid, this coal slurry is extruded from the annular space 114 defined by the inner shell wall 111 and the intermediate shell wall 113. The outer, oxidizer gas nozzle shell 115 surrounds the outer nozzle discharge annulus 116. The upper assembly port 101, as shown in FIG. 3, supplies the outer nozzle discharge annulus with an additional stream of oxidizing gas. Centralizing fins 117 and 118 extend laterally from the outer surface of the inner and intermediate nozzle shell walls 111 and 113, respectively to keep their respective shells coaxially centered relative to the longitudinal axis of the injector assembly. It will be understood that the structure of the fins 117 and 118 form discontinuous bands about the inner and intermediate shells and offer small resistance to fluid flow within the respective annular spaces.

The internal nozzle shell 111 and intermediate nozzle shell 113 can both be axially adjustable relative to the outer nozzle shell 115 for the purpose flow capacity variation. As intermediate nozzle 113 is axially displaced from the conically tapered internal surface of outer nozzle 115, the outer discharge annulus 116 is enlarged to permit a greater oxygen gas flow. Similarly, as the outer tapered surface of the internal nozzle 111 is axially drawn toward the internally conical surface of the intermediate nozzle 113, the feedstock slurry discharge area 114 is reduced.

Surrounding the outer nozzle shell 115 is a coolant fluid jacket 110 having an annular end closure 119. A coolant fluid conduit 120 delivers a coolant, such as water, from the upper assembly supply port 100 in FIG. 3 directly to the inside surface of the end closure plate 119. Flow channeling baffles 121 control the path of coolant flow around the outer nozzle shell to assure a substantially uniform heat extraction and to prevent the coolant from channeling and producing localized hot spots. The end closure 119 includes a nozzle lip 122 that defines an exit orifice or discharge opening for the feeding of reaction materials into the injection injector assembly.

The planar end of the cooling jacket 119 includes an annular surface 123 which is disposed facing the combustion chamber. Typically, the annular surface 123 of cooling jacket is composed of cobalt base metal alloy materials. Although cobalt is the preferred material of construction for the nozzle assembly 125, other high temperature melting point alloys, such as molybdenum or tantalum may also be used. The heat shield 124 is formed from a high temperature melting point material such as silicon nitride, silicon carbide, zirconia, molybdenum, tungsten or tantalum.

While this discussion was based on a injector and feed stream arrangement as previously described, it is understood that the injector may consist of only two passages for introducing and injecting the oxidant and feedstock stream, and they may be in any order with the feedstock stream passing through the central axial bore opening while the feedstock is fed through an annulus surrounding at least a portion of the central oxidant conduit, or the order may be reversed as described above.

An example of the operation of the gasifier and scrubber is illustrated in FIG. 2. The coal/CE and plastics feedstock slurry is fed to the gas generator 50 through injector 51 mounted at the top 52 of the gasifier and is fed with oxygen through line 53 and injected into the gasification zone 54 to generate a raw syngas. The raw syngas gases discharged from the gasifier is fed to a contactor 55. Water is injected into contactor 55 from line 56 through injectors 56 and 57. Intimate contact between the raw syngas from line 58 and water from line 56 is effected desirably by way of a venturi, nozzle, or plate orifice. In contactor 55, the syngas stream is accelerated, and water is injected into the accelerated gas stream at the throat of the nozzle, venturi or orifice, from a plurality of injectors 56 and 57.

The resulting mixture of gas and water formed in contactor 55 is directed into scrubber 59 through a dip leg 60 which extends downwardly into the lower portion of scrubber 59. The gas stream from contactor 55 also carries entrained solid particles of unconsumed fuel or ash. A body of water is maintained in the scrubber 59, the level of which may be controlled in any suitable manner, for example by means of a liquid level controller 61, shown diagrammatically. The dip leg 60 discharges the mixture of water and gas below the level of water contained in the scrubber 59. By discharging the mixture of gas and water through the open end of dip leg 60 into intimate contact with water, solid particles from the gas stream are trapped in the water.

Scrubber 59 is suitably in the form of a tower having an optionally packed section 62 above the point of entry of the gas stream from contactor 55. Water from line 63 is introduced into scrubber 59 above the level of the packing material 62. In packed section 62, the gas stream is intimately contacted with water in the presence of suitable packing material, such as ceramic shapes, effecting substantially complete removal of solid particles from the gas stream. Product gas, comprising carbon monoxide and hydrogen and containing water vapor, atmospheric gases, and carbon dioxide, is discharged from the upper end of scrubber 59 through line 64 at a temperature corresponding to the equilibrium vaporization temperature of water at the pressure existing in scrubber 59. Clean syngas from line 64 may be further processed, for example, for the production of higher concentrations of hydrogen by water-gas shift reaction and suitable downstream purification to remove sulfur.

Water from the lower portion of scrubber 59 is passed by pump 65 through line 56 to injectors 56 and 57. Clarified water from settler 66 also may be supplied to line 56 by pump 67 through line 68. Water is withdrawn from scrubber 59 by pump 69 and passed through valve 70 responsive to liquid level control 61 on the scrubber and passed into quench zone 71 via line 72 to control the liquid level in scrubber 59.

Any heavy solid particles removed from the gas stream in the dip leg 60 settling into water slurry are collected the water bath at the bottom of the scrubber 59 and discharged at the bottom leg 73 at periodic intervals through line 74 as controlled by valve 75.

Any suitable scrubber design can be used in the process. Other scrubber designs include a tray type contacting tower wherein the gases are counter currently contacted with water. Water is introduced into the scrubber at a point near the top of the tower.

EXAMPLES

Example 1

Plastics are milled to a nominal particle size between 1 mm and 0.5 mm. Coal is dried and crushed in a Retsch jaw crusher to a nominal size of <2 mm. A predetermined amount of water is added to a 4.5 L metal bucket. Ammonium lignosulfonate is added to the water in the metal bucket and mixed with a spatula until it is distributed evenly. Ground plastics and coal are added to the water and ALS mixture in the metal bucket and then the blend is mixed by an overhead mixer. Aqueous ammonia is added to the slurry to adjust the pH to 8±0.2. After being well mixed, the sample is placed in the laboratory rod mill equipped with 5 stainless steel rods at ½"×9", 8 rods at ⅝"×9", 8 rods at ¾"×9", 2 rods at 1"×9", and 1 rod at 1¼"×9". The slurry is milled for 1 hour at approximately 28 rpm (mill outside diameter=11.75 inches). The aqueous ammonia is again used to adjust the pH to 8±0.2 while the slurry is mixed by the overhead mixer. Each batch of slurry is made to be a total of approximately 3000 grams with approximately 69% solids with varying amounts of recycled materials as reported in Table 1 below. Viscosity and stability tests are conducted with the results listed in Table 1.

500-550 g samples of coal slurry are transferred to a 600 mL glass beaker to measure the viscosity and stability. The stability of each sample can be judged by visual observation. The slurry is well mixed to generate a homogeneous distribution of particles throughout the sample and letting the slurry sit undisturbed for a period of time. The slurry is then remixed. If a layer of particles separated out at the bottom of the beaker, the slurry will be difficult to remix, and it is then considered to have settled. Over a period of time, the slurries will have settling. However, the longer the amount of time required to settle determines whether the stability of the slurry is considered good, moderate, or poor. If the slurry settles before 5 minutes, it is considered poor.

In an alternative method, the stability of the slurry can be determined quantitively. The viscosities of the slurry samples are measured at room temperature using either a Brookfield viscometer with an LV-2 spindle rotating at a rate of 0.5 rpm (method A) or a Brookfield R/S rheometer with V80-40 vane spindle operating at a shear rate of 1.83/s (method B). An average of 3 viscosity measurements is reported.

The stability is measured, by either Method A or Method B, by submerging the spindle of the rheometer into the slurry at the bottom of the beaker after the slurry is well mixed to form a homogeneous distribution of solids. After a designated period of time, the viscosity is measured with the spindle at the bottom of the beaker. The viscosity increases with settling and the slurry is considered to have settled if the initial reading on starting a viscosity measurement is 100,000 cP. Thus, slurries are considered stable if the initial viscosity is 100,000 cP or less after standing still for 5 minutes.

The pumpability of a slurry is measured by Method A or Method B. The slurry is considered pumpable if the viscosity reading is 30,000 cP or less (desirably 25,000 or less or better is 20,000 or less) when taking a reading immediately after well mixing the slurry to form a homogeneous distribution of solids.

The results of stability are determined by visual observation, and the results of pumpability are reported in Table 1 in the viscosity column using Method A. The ground plastic is virgin PET pellets milled to a 1 mm nominal size or smaller. Stability is determined at the 5-minute mark.

TABLE 1

Effect of increasing ground plastic loadings on coal-water slurry properties.

| Substrate ID | Substrate % of solids | Substrate % of total | ALS % | Target Solids % | Measured Solids % | Viscosity[a] | Stability | Overall |
|---|---|---|---|---|---|---|---|---|
| Control | 0% | 0% | 0.40% | 69% | 69.5% | 4040 cP | Moderate | Good |
| PET | 1.5% | 1.0% | 0.20% | 69% | 68.9% | 12590 cP | Good | Good |
| PET | 3.0% | 2.0% | 0.40% | 69% | 70.1% | 11230 cP | Good | Good |
| PET | 17.1% | 10.0% | 0.40% | 69% | 69.4% | 11093 cP | Good | Good |
| PET | 41.2% | 20.0% | 0.40% | 69% | 70.3% | 16000 cP | Good | Good |
| PET | 61.7% | 26.2% | 0.35% | 69% | 68.5% | 13440 cP | Good | Good |

[a]Measured by method A.

All of the mixtures tested up to 61.7% of the solids (26.2% of the total slurry) demonstrate good slurry properties and would be usable in the gasifier. At low loadings the stability of the slurry is good.

Example 2

Batches of a coal/plastic slurry are prepared as stated in Example 1 and in the amounts reported in Table 2 using low density polyethylene as the plastic. The results of stability and pumpability are reported below in Table 2 using Method B in each case. A report of "stable" in the stability column indicates a viscosity reading of less than 100,000 cP at the time period stated.

TABLE 2

Effect of increasing ground LDPE loadings(20) on coal-water slurry properties.

| Substrate ID | Substrate % of solids | Substrate % of total | ALS % | Target Solids % | Measured Solids % | Viscosity | Stability 5 min | Stability 10 min | Stability 20 min | Overall |
|---|---|---|---|---|---|---|---|---|---|---|
| Control | 0% | 0% | 0.20% | 69% | 69.4% | 4554 cP | Stable | Stable | Stable | Good |
| LDPE | 2% | 1.4% | 0.20% | 69% | 70.0% | 5357 cP | Stable | Stable | Stable | Good |
| LDPE | 5% | 3.4% | 0.20% | 69% | 69.8% | 9293 cP | Stable | Stable | Stable | Good |
| LDPE | 10% | 6.9% | 0.40% | 69% | 68.6% | 50622 cP | Stable | NA | NA | Too Viscous |

All samples remained stable at 5 minutes. However, at a 10% of solids loading, the LDPE sample would be considered too viscous to be effectively pumpable.

Example 3

All recycled CE and other plastics are size reduced and ground such that they pass through a 1.5 mm screen. Batches of a coal/recycle plastic slurry are prepared as stated in Example 1 and in the amounts reported in Table 2 using a variety of different types of plastics according to the legend below. The results of stability and pumpability are reported below in Table 2 using Method B in each case.

The following legend describes the plastics employed:

PEX: crosslinked polyethylene
LDPE: Low-density polyethylene
PET: Polyethylene terephthalate
CDA: Cellulose diacetate
DEP: Diethyl phthalate
HDPE: High-density polyethylene
Acetate Tow: Cellulose acetate tow

| Substrate ID | Substrate % of solids | Substrate % of total | ALS % | Target Solids % | Viscosity | Stability | Overall |
|---|---|---|---|---|---|---|---|
| Control | 0% | 0% | 0.40% | 69% | 5222 | >20 min | Good |
| PEX | 2.00% | 1.38% | 0.20% | 69% | 14247 | >20 min | Good |
| PEX | 5.00% | 3.45% | 0.20% | 69% | 4492 | >20 min | Good |
| PEX | 10.00% | 6.90% | 0.20% | 69% | 8858 | >20 min | Good |
| PEX | 12.00% | 8.28% | 0.20% | 69% | 12083 | >20 min | Good |
| PEX | 15.00% | 10.35% | 0.20% | 69% | 20971 | >20 min | Good |
| PEX | 17.00% | 11.73% | 0.20% | 69% | 37963.508 | 20 min | Too Thick |
| PEX | 20.00% | 13.80% | 0.20% | 69% | 34401.154 | 10 min | Too Thick |
| Control | 0% | 0% | 0.20% | 69.4% | 5945 | >20 min | Good |
| LDPE film | 2.00% | 1.38% | 0.20% | 70.0% | 5357 | >20 min | Good |
| LDPE film | 5.00% | 3.45% | 0.20% | 69.8% | 9293 | >20 min | Good |
| LDPE Film | 10.00% | 6.90% | 0.40% | 68.6% | 50622 | >20 min | Too Thick |
| Control | 0% | 0% | 0.20% | 69.4% | 4554 | >20 min | Good |
| PET (DCF) | 2% | 1.38% | 0.20% | 69.4% | 2769 | 15 min | Good |
| PET (DCF) | 5% | 3.45% | 0.20% | 69.5% | 3536 | 15 min | Good |
| PET (DCF) | 10% | 6.90% | 0.20% | 68.8% | 7731 | 15 min | Good |
| PET (ECF) | 2% | 1.38% | 0.20% | 69.8% | 2699 | >20 min | Good |
| PET (ECF) | 5% | 3.45% | 0.20% | 69.2% | 2571 | 15 min | Good |
| PET (ECF) | 10% | 6.90% | 0.20% | 68.9% | 2990 | 15 min | Good |
| PET (ECF) | 15% | 10.35% | 0.40% | 69.8% | 3896 | >20 min | Good |

| Substrate | Percent of Solids | Average Viscosity (cP) | Stable? | Viscosity after 5 minutes settling | Slurry Acceptable? |
|---|---|---|---|---|---|
| Control 1 | 0 | 2953 | yes | 5278 | yes |
| CDA w 25% DEP | 2 | 5314 | yes | 12462 | yes |
| HDPE | 2 | 5934 | yes | 4265 | yes |
| PEX | 2 | 5934 | yes | 15475 | yes |
| Acetate tow | 0.5 | 21510 | yes | 25980 | no |
| Acetate tow | 2 | could not create slurry - tow absorbed too much water | | | no |

What we claim is:

1. A process for preparing a recycle cellulose ester (Recycle CE) comprising: (1) preparing a recycled CE content syngas in a synthesis gas operation by gasifying a feedstock containing a solid fossil fuel source, at least some content of recycled CE, and optional recycled plastics, wherein the feedstock comprises the solid fossil fuel source in an amount of at least 80 wt %, based on the weight of solids in the feedstock, and comprises not more than 0.5 wt. % of any one of sewage sludge, waste paper, biomass, or a combination of two or more, each based on the weight of solids in the feedstock; (2) using the recycled CE content syngas as a feedstock in a reaction scheme to produce at least one cellulose reactant for preparing a Recycle CE; and (3) reacting said at least one cellulose reactant to prepare at least one Recycle CE, wherein the process comprises a closed loop process.

2. The process according to claim 1, wherein the at least one cellulose reactant is chosen from acetic acid, acetic anhydride, propionic acid, butyric acid, and combinations thereof.

3. The process according to claim 1, wherein the at least one Recycle CE is a type of cellulose ester chosen from cellulose acetate (CA), cellulose diacetate (CDA), cellulose triacetate (CTA), cellulose butyrate (CB), cellulose propionate (CP), cellulose acetate butyrate (CAB), cellulose acetate propionate (CAP), or combinations thereof; and wherein said recycled CE comprises a type of cellulose ester that is the same as the Recycle CE.

4. The process according to claim 1, wherein the reaction scheme to produce at least one cellulose reactant comprises one or more of the following reactions: (1) converting said recycled CE content syngas to methanol; (2) reacting said methanol to produce acetic acid; (3) reacting said methanol and/or said acetic acid to produce methyl acetate; and (4) reacting said methyl acetate and/or said methanol to produce acetic anhydride.

5. The process according to claim 4, wherein the reaction scheme to produce at least one cellulose reactant comprises all of reactions (1) through (4).

6. An integrated process for preparing a Recycle CE which comprises the processing steps of: (1) preparing a recycled CE content syngas in a synthesis gas operation utilizing a feedstock that contains a solid fossil fuel source and at least some content of recycled CE, wherein the feedstock comprises the solid fossil fuel source in an amount of at least 80 wt %, based on the weight of solids in the feedstock, and comprises not more than 0.5 wt. % of any one of sewage sludge, waste paper, biomass, or a combination of two or more, each based on the weight of solids in the feedstock; (2) preparing at least one chemical intermediate from said syngas; (3) reacting said chemical intermediate in a reaction scheme to prepare at least one cellulose reactant for preparing a Recycle CE, and/or selecting said chemical intermediate to be at least one cellulose reactant for preparing a Recycle CE; and (4) reacting said at least one cellulose reactant to prepare said Recycle CE; wherein said Recycle CE comprises at least one substituent on an anhydroglucose unit (AGU) derived from recycled CE content syngas, wherein the process comprises a closed loop process.

7. The process according to claim 1, wherein the recycle CE content syngas is prepared by a process comprising:

a. charging an oxidant and a feedstock slurry composition to a gasification zone within a gasifier, said feedstock slurry composition comprising CE, a solid fossil fuel, and water, wherein either (i) the amount of CE and optional plastics is less than 5 wt. % based on the weight of the solids in the feedstock slurry or (ii) 90 wt. % of the CE and optional plastics have a particle size in the largest dimension of not more than 2 mm;

b. gasifying the feedstock composition together with the oxidant in a gasification zone to produce a syngas composition; and c. discharging at least a portion of the syngas composition from the gasifier, wherein at least one of the following conditions is present:

(i) gasification within the gasification zone is conducted at a temperature of at least 1000° C., or (ii) the pressure within the gasification zone greater than 2.7 MPa, or (iii) the feedstock composition is a slurry, or (iv) no steam is introduced to the gasifier that flows into the gasification zone, or (v) the CE and plastics are pre-ground such that at least 90% of the particles have a particle size of less than 2 mm, or (vi) the tar yield is less than 4 wt. %, or (vii) the gasifier contains no membrane wall in the gasification zone, or (viii) a combination of two or more of the above conditions.

8. The process according to claim 1, wherein the feedstock is in the form of a feedstock slurry composition comprising CE, a solid fossil fuel, and water, wherein the CE and optional plastics have a particle size of not more than 2 mm, and the solid fossil fuel in the feedstock composition has a particle size of less than 2 mm, the solids content in the slurry is at least 62 wt. %, the amount of CE and plastics present in the feedstock stream slurry composition is 0.1 wt. % to less than 5 wt. % based on the weight of all solids, and the water is at least 20 wt. % based on the weight of the feedstock slurry composition, and wherein either:

a. the slurry is stable as determined by having an initial viscosity of 100,000 cP or less at 30 minutes using a Brookfield R/S Rheometer equipped with V80-40 vane operating at a shear rate of 1.83/s, measured at ambient conditions; or b. the slurry is pumpable as determined by having a viscosity of less than 30,000 cP, or 25,000 cP or less, or not more than 23,000 cP after mixing to obtain a homogeneous distribution of solids throughout the slurry and using a Brookfield R/S Rheometer equipped with V80-40 vane operating at a shear rate of 1.83/s, measured at ambient conditions, or c. both.

9. The process according to claim 1, wherein the recycled CE is obtained from tool handles, ophthalmic products, sheet, film, or coating, optical films, photographic film, coatings, buttons, or toys, or combinations thereof.

10. The process according to claim 1, wherein the feedstock comprises recycled CE at least a portion of which is obtained from eyeglass frames.

11. The process according to claim 1, wherein the Recycle CE is biodegradable.

12. A process for preparing a recycle cellulose acetate composition (Recycle CA) comprising: (1) preparing a recycled CE content syngas in a synthesis gas operation by gasifying a feedstock containing a solid fossil fuel source and at least some content of cellulose acetate scrap, wherein the feedstock comprises the solid fossil fuel source in an amount of at least 80 wt %, based on the weight of solids in the feedstock, and comprises not more than 0.5 wt. % of any one of sewage sludge, waste paper, biomass, or a combination of two or more, each based on the weight of solids in the feedstock; (2) determining a recycled content value of the feedstock; (3) providing a cellulose acetate composition and determining a recycled content value for the composition to provide a recycle cellulose acetate composition (Recycle CA), wherein at least a portion of the composition recycled content value is associated with the feedstock recycled content value, and wherein the cellulose acetate scrap comprises cellulose acetate and/or cellulose diacetate.

13. The process according to claim 12, where the cellulose acetate composition is provided by using the recycled CE content syngas as a feedstock in a reaction scheme to produce at least one cellulose reactant for preparing the Recycle CA; and reacting said at least one cellulose reactant to prepare the Recycle CA.

14. The process according to claim 12, wherein the cellulose acetate scrap comprises cellulose acetate scrap obtained from ophthalmic article manufacturing and wherein the Recycle CA is used in an ophthalmic article manufacturing process.

15. The process according to claim 12, wherein the composition recycled content value is obtained by mass balance allocation.

16. The process according to claim 1, wherein the feedstock does not contain sewage sludge, waste paper, or biomass.

17. The process according to claim 14, wherein the feedstock does not contain sewage sludge, waste paper, or biomass.

* * * * *